United States Patent [19]

Nicholson et al.

[11] Patent Number: 4,704,159

[45] Date of Patent: Nov. 3, 1987

[54] HERBICIDAL FLUOROETHOXY PYRIMIDINES

[75] Inventors: Michael D. Nicholson; Gerald A. Roy, Jr., both of Wilmington, Del.

[73] Assignee: E. I. Du Pont de Nemours and Company, Wilmington, Del.

[21] Appl. No.: 861,258

[22] Filed: May 9, 1986

Related U.S. Application Data

[60] Division of Ser. No. 699,174, Feb. 12, 1985, Pat. No. 4,609,398, which is a continuation-in-part of Ser. No. 625,911, Jun. 29, 1984, abandoned, which is a continuation-in-part of Ser. No. 587,063, Mar. 7, 1984, abandoned.

[51] Int. Cl.$^4$ .................. A01N 43/54; C07D 239/69
[52] U.S. Cl. .......................................... 71/92; 71/93; 544/211; 544/321
[58] Field of Search ............................. 71/92; 544/321

[56] References Cited

U.S. PATENT DOCUMENTS 4,518,776  5/1985  Meyer et al. .................. 544/321

*Primary Examiner*—John M. Ford

[57] ABSTRACT

Specific fluoroethoxy pyrimidines and triazines are useful as general or selective preemergent and postemergent herbicides. Ortho-ethoxy and ortho-propoxy substituted benzenesulfonamides, such as 2-ethoxy-N-[[4-methoxy-6-(2,2,2-trifluoroethoxy)1,3,5-triazin-2-yl]aminocarboxyl]benzenesulfonamide and N-[[4-methoxy-6-(2,2,2-trifluoroethoxy)-1,3,5-triazin-2-yl]aminocarbonyl]-2-propoxybenzenesulfonamide, and their agriculturally suitable salts show pre-emergent and postemergent herbicidal utility in corn.

6 Claims, No Drawings

HERBICIDAL FLUOROETHOXY PYRIMIDINES

RELATED APPLICATION

This application is a division of U.S. Ser. No. 699,174, filed Feb. 12, 1985, now U.S. Pat. No. 4,609,348, which is a continuation-in-part of application U.S. Ser. No. 625,911, filed June 29, 1984, now abandoned, which is a continuation-in-part of application U.S. Ser. No. 587,063, filed Mar. 7, 1984, now abandoned.

BACKGROUND OF THE INVENTION

The present invention relates to novel 2-fluoro-2,2-difluoro- and 2,2,2-trifluoroethoxy pyrimidine- and triazine-containing sulfonylureas which are useful as preemergent and postemergent herbicides.

Herbicidal benzenesulfonylureas of the formula

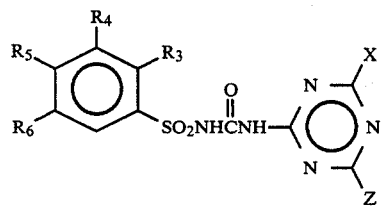

wherein among the substituents disclosed $R_{4-6}$ can each be hydrogen, $R_3$ can be alkoxy of 1-4 carbon atoms, X can be alkoxy of 1-3 carbon atoms and Z is methyl or methoxy are disclosed in U.S. Pat. No. 4,127,405, issued Nov. 28, 1978 to Levitt.

European Patent Application (EP-A) No. 9419, published Apr. 2, 1980, discloses herbicidal benzene and thiophene sulfonylureas such as

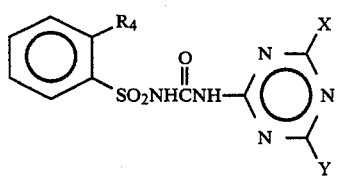

wherein among the substituents disclosed $R_4$ can be $OCH_3$, X can be $OCH_3$, and Y can be $OCH_2CF_3$.

South African Application No. 825671 (Swiss priority Aug. 6, 1981; EP-A-72,347, published Feb. 16, 1983) claims ortho-substituted alkoxy benzenesulfonylureas such as

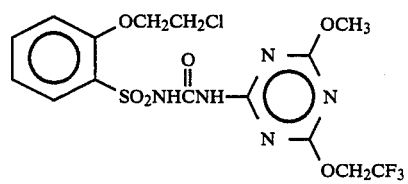

South African Patent Application 835165 filed by Ciba-Geigy (Swiss Priority 7/16/82) discloses herbicidal sulfonylureas of the general structure shown below:

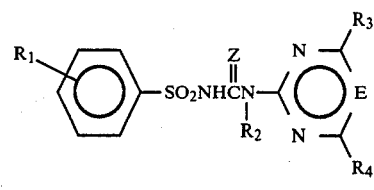

wherein

A is an unsubstituted or substituted bridge of 3 or 4 atoms which contains 1 or 2 oxygen, sulfur or nitrogen atoms and, together with the linking carbon atom, forms a non-aromatic 5- or 6-membered heterocyclic ring system, with the proviso that two oxygen atoms are separated by at least one carbon atom and that oxygen and sulfur atoms are only linked to each other if the sulfur atom takes the form of the —SO— or $SO_2$— group; and $R_3$ and $R_4$ may be, among other values, a $C_1$-$C_4$ haloalkoxy group.

SUMMARY OF THE INVENTION

This invention relates to novel compounds of Formula I, agriculturally suitable compositions containing them, and their method-of-use as general or selective preemergent and postemergent herbicides.

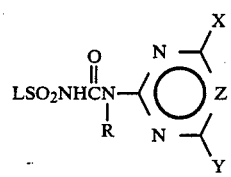

wherein
R is H or $CH_3$;
X is $CH_3$ or $OCH_3$;
Y is $OCH_2CH_2F$, $OCH_2CHF_2$ or $OCH_2CF_3$;
Z is CH or N;

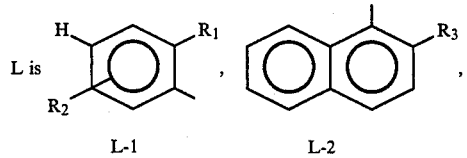

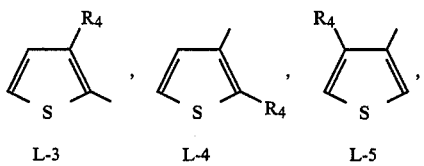

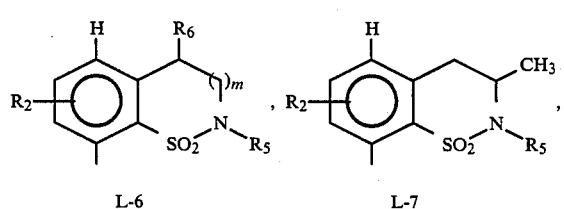

L-8 (structure with R2, R7, SO2NR5)

L-9 (structure with R2, R7, O)

L-10 (structure with R2, R7, O)

$R_1$ is $C_2$-$C_4$ alkyl, $C_2$-$C_4$ alkoxy, $SO_2NR_8R_9$, $SO_2N$-$(OCH_3)CH_3$, or 2-tetrahydrofuranyl;

$R_2$ is H, F, Cl, Br, $CF_3$, $CH_3$, $OCH_3$ or $SCH_3$;

$R_3$ is H, $CH_3$, $OCH_3$, F, Cl, Br, $SO_2N(CH_3)_2$, $OSO_2CH_3$ or $S(O)_nCH_3$;

$R_4$ is $C_1$-$C_3$ alkyl, F, Cl, Br, $NO_2$, $SO_2NR_8R_9$, $SO_2N$-$(OCH_3)CH_3$ or $S(O)_nR_{10}$;

$R_5$ is H, $C_1$-$C_5$ alkyl, $CH_3OCH_2CH_2$, $C_2H_5OCH_2CH_2$ or $C_1$-$C_4$ alkyl substituted with 1-3 atoms of F or Cl or 1 Br;

$R_6$ is H or $CH_3$;

$R_7$ is H or $CH_3$;

$R_8$ is $C_1$-$C_3$ alkyl;

$R_9$ is $C_1$-$C_3$ alkyl;

$R_{10}$ is $C_1$-$C_3$ alkyl or $CH_2CH=CH_2$;

m is 0 or 1; and n is 0, 1 or 2;

and their agriculturally suitable salts; provided that (1) the total number of carbon atoms of $R_8$ and $R_9$ is less than or equal to four;

(2) when m is 1, $R_6$ is H;

(3) when L is L-1 and $R_1$ is $SO_2NR_8R_9$, $SO_2N$-$(OCH_3)CH_3$ or 2-tetrahydrofuranyl, then Y is $OCH_2CH_2F$ or $OCH_2CHF_2$; and (4) when L is L-6, L-7, L-8, L-9 or L-10, then Y is $OCH_2CH_2F$ or $OCH_2CHF_2$.

Preferred for reasons of their greater herbicidal activity, greater plant growth regulant activity and/or more favorable ease of synthesis are:

(1) Compounds of Formula I where L is L-1.
(2) Compounds of Formula I where L is L-2.
(3) Compounds of Formula I where L is L-3.
(4) Compounds of Formula I where L is L-4.
(5) Compounds of Formula I where L is L-5.
(6) Compounds of Formula I where L is L-6 or L-7.
(7) Compounds of Formula I where L is L-8 or L-9.
(8) Compounds of Formula I where L is L-10.
(9) Compounds of Preferred 1 where R is H; $R_1$ is $C_2$-$C_3$ alkoxy; $R_2$ is H; and Z is N.
(10) Compounds of Preferred 2 where R is H; $R_3$ is $CH_3$, $OCH_3$, Cl, $SCH_3$ or Br; and Z is N.
(11) Compounds of Preferred 3 where R is H; $R_4$ is $CH_3$, $S(O)_nCH_3$, $S(O)_nCH_2CH_3$ or $SO_2N(CH_3)_2$; and Z is N.
(12) Compounds of Preferred 4 where R is H; $R_4$ is $CH_3$, $S(O)_nCH_3$, $S(O)_nCH_2CH_3$ or $SO_2N(CH_3)_2$; and Z is N.
(13) Compounds of Preferred 5 where R is H; $R_4$ is $CH_3$, $S(O)_nCH_3$, $S(O)_nCH_2CH_3$ or $SO_2N(CH_3)_2$; and Z is N.

(14) Compounds of Preferred 6 where R is H; $R_2$ is H; $R_5$ is H, $C_1$-$C_4$ alkyl, $CH_2CH_2OCH_3$, $CH_2CH_2OC_2H_5$ or $C_1$-$C_4$ alkyl substituted with 1-3 atoms of F or Cl or 1 Br; $R_6$ is H; and Z is N.

(15) Compounds of Preferred 7 where R is H; $R_2$ is H; $R_5$ is H, $C_1$-$C_4$ alkyl, $CH_2CH_2OCH_3$, $CH_2CH_2OC_2H_5$ or $C_1$-$C_4$ alkyl substituted with 1-3 atoms of F or Cl or 1 Br; and Z is N.

(16) Compounds of Preferred 8 where R is H; $R_2$ is H; and Z is N.

Specifically Preferred for their greatest herbicidal activity, greatest plant growth regulant activity and/or most favorable ease of synthesis are:

2-ethoxy-N-[[4-methoxy-6-(2,2,2-trifluoroethoxy)-1,3,5-triazin-2-yl]aminocarbonyl]benzenesulfonamide, m.p. 180°-181° (d); and N-[[4-methoxy-6-(2,2,2-trifluoroethoxy)-1,3,5-triazin-2-yl]aminocarbonyl]-2-propoxybenzenesulfonamide, m.p. 161°-163° (d).

These compounds are excellent preemergent and postemergent herbicides for use in corn.

DETAILED DESCRIPTION OF THE INVENTION

Compounds of Formula I are prepared by the procedure of Equation 1 wherein L, R, X, Y and Z are as previously defined. This procedure is well known in the art.

Equation 1

$$L-SO_2NCO + HN\underset{R}{-}\text{(triazine)} \longrightarrow I$$

II          III

The reaction is best carried out in inert aprotic organic solvents such as methylene chloride, tetrahydrofuran or acetonitrile, at ambient pressure and temperature. The mode of addition is not critical; however, it is often convenient to add the sulfonyl isocyanate to a stirred suspension of the aminotriazine. Since such isocyanates usually are liquids, their addition is more easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane, ethyl ether, or pentane, and filtration.

The intermediate sulfonyl isocyanates of Formula II can be prepared by reacting corresponding sulfonamides with phosgene in the presence of n-butyl isocyanate at reflux in a solvent such as chlorobenzene, according to the procedure of H. Ulrich and A. A. Y. Sayigh, *Newer Methods of Preparative Organic Chemistry*, Vol. VI, pages 223-241, Academic Press, New York and London, W. Foerst Ed. In cases where formation of the desired sulfonyl isocyanate is difficult by the above procedure the sulfonylurea formed by reaction of butyl isocyanate with the appropriate sulfonamide is treated with phosgene according to the above reference.

Alternatively, compounds of Formula I can be prepared by contacting a sulfonyl carbamate of Formula IV with amine III as shown in Equation 2.

Equation 2

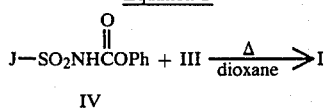

IV

The reaction is carried out at 50° to 100° C. in a solvent such as dioxane for 0.5 to 24 hours as taught in EP-A-44,807. The required carbamates IV are prepared by contacting the corresponding sulfonamides V with diphenylcarbonate or phenylchloroformate in the presence of base.

The compounds of Formula I can also be prepared by contacting a sulfonamide of Formula V with an O-phenylcarbamate of Formula VI in the presence of base as shown in Equation 3.

Equation 3

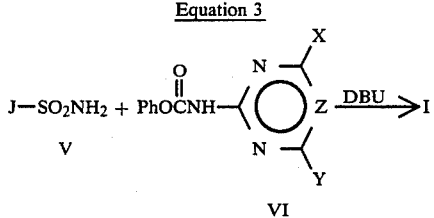

VI

The reaction is carried out at 0° to 50° C. in an inert solvent such as acetonitrile for 0.1 to 24 hours in the presence of a base such as 1,8-diazabicyclo[5.4.0]undec-7-ene (DBU) as taught in EP-A-44,807. The required carbamate VI is prepared by reacting amine III with diphenylcarbonate or phenylchloroformate in the presence of base.

The sulfonamides used as intermediates for this invention can be prepared by methods known in the art. The preparation of $LSO_2NH_2$ where L is L-1 can be prepared as taught in U.S. Pat. Nos. 4,127,405; 4,310,346 or 4,435,205. When L is L-3, L-4 or L-5, methods such as those referred to in EP-A-64,804 and U.S. Pat. No. 4,398,939 can be used for the preparation of the sulfonamide intermediates. Naphthalenesulfonamides (L is L-2) can be prepared according to procedures referred to or described in U.S. Pat. No. 4,370,479. Sulfonamides where L is L-6, L-7, L-8, L-9 or L-10 can be prepared as described in EP-A-107,979.

Aminotriazines of structure III can be prepared by methods described in EP-A-9,419 (published Apr. 2, 1980). Pyrimidine intermediates of structure III can be prepared by similar procedures by substituting an appropriately substituted pyrimidine for triazines used in the procedures referred to above.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., an alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble.

Acid addition salts, useful in this invention, can be obtained by reacting a compound of Formula I with a suitable acid, e.g., p-toluenesulfonic acid, trichloroacetic acid or the like.

The compounds of this invention and their preparation are further illustrated by the following examples wherein temperatures are given in degrees centigrade.

EXAMPLE 1

2-Amino-4-(2,2,2-trifluoroethoxy)-6-methoxy-1,3,5-triazine

A. A solution of 300 g (1.63 mol) of cyanuric chloride in 1 liter THF and 0.24 liter diglyme was cooled to 0° C. and 81.6 mL (3.36 mol) of liquid ammonia added dropwise over 90 min. keeping the temperature between 10°–15°. The mixture was stirred for one hour at −10° to 0° and then allowed to warm to ambient temperature over one hour. The resulting suspension was filtered, the solid washed with THF, the filtrate reduced to ½ its original volume, and poured over 1 liter of ice water to give a white solid which was collected, washed with water, and dried in vacuo to give 244.3 g of 2-amino-4,6-dichloro-1,3,5-triazine with m.p. 221°–223.5° (dec).

B. To a suspension of 50.0 g (0.3 mol) of 2-amino-4,6-dichloro-1,3,5-triazine in 600 mL of methanol was added portionwise 19.5 g (0.3 mol) of 85% potassium hydroxide pellets with the temperature being kept between 15°–20°. The resulting suspension was stirred at 10°–15° for one hour and then allowed to warm to room temperature over 1.5 hours. The white solid was collected, washed three times with water, and dried in vacuo to give 37.1 g of 2-amino-4-chloro-6-methoxy-1,3,5-triazine with m.p. 221°–223.5° (dec).

C. To a suspension of 10.0 g (0.06 mol) of 2-amino-4-chloro-6-methoxy-1,3,5-triazine and 6.2 g (0.06 mol) of 2,2,2-trifluoroethanol in 150 mL of methylene chloride was added portionwise over five minutes 4.1 g (0.06 mol) of 85% potassium hydroxide pellets. After an initial exotherm to 27° the reaction mixture was stirred at ambient temperature overnight. The suspended solid was removed by filtration and filtrate concentrated in vacuo to give 13.21 g of white solid with m.p. 77°–80°. This was recrystallized from n-butyl chloride to give 11.16 g of 2-amino-4-(2,2,2-trifluoroethoxy)-6-methoxy-1,3,5-triazine as a white powder with m.p. 78°–80°.

NMR: $(CDCl_3+DMSO-d_6)$ δ3.96 (s, $OCH_3$) 4.79 (q, $OCH_2CF_3$) 6.5 (br s, $NH_2$)

EXAMPLE 2

2-Ethoxy-N-[[4-methoxy-6-(2,2,2-trifluoroethoxy)-1,3,5-triazin-2-yl]aminocarbonyl]benzenesulfonamide To 1.9 g of 2-amino-4-(2,2,2-trifluoroethoxy)-6-methoxy-1,3,5-triazine suspended in 50 mL of dry methylene chloride was added 2.4 g of 2-ethoxybenzenesulfonyl isocyanate. The mixture was stirred at ambient temperature for three days, filtered, and the filtrate stripped to an oil which crystallized. The solid was triturated with n-butyl chloride and collected to give 2.94 g of white solid with m.p. 180°–181° (dec).

NMR: (CDCl$_3$+DMSO-d$_6$) δ1.25 (t, CH$_3$) 4.0 (s, OCH$_3$) 4.2 (q, OCH$_2$) 5.2 (Q, OCH$_2$CF$_3$) 7.0–8.0 (m, aromatics) 10.8 (br s, NH) 11.7 (br s, NH).

EXAMPLE 3

N-[[4-methoxy-6-(2,2,2-trifluoroethoxy)-1,3,5-triazin-2-yl]aminocarbonyl]-2-propoxybenzenesulfonamide To 2.0 g of 2-amino-4-(2,2,2-trifluoroethoxy)-6-methoxy-1,3,5-triazine suspended in 35 mL of dry methylene chloride was added 4.4 g of a 50% solution of 2-n-propoxybenzenesulfonyl isocyanate in methylene chloride. The mixture was stirred overnight at ambient temperature and the resulting solution stripped to an amber oil which was triturated with ethanol to give 1.42 g of white solid with m.p. 161°–163° (dec).

NMR: (CDCl$_3$+DMSO-d$_6$) δ0.9 (t, CH$_3$) 1.7 (m, CH$_2$) 4.1 (m, OCH$_3$ and OCH$_2$) 5.1 (q, OCH$_2$CF$_3$) 7.0–8.0 (m, aromatics) 10.7 (br s, NH) 11.6 (br s, NH)

The following compounds can be prepared by one skilled in the art using the proper reactants and the procedures outlined above.

General Structures for Tables

General Structure I

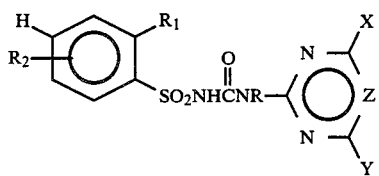

General Structure II

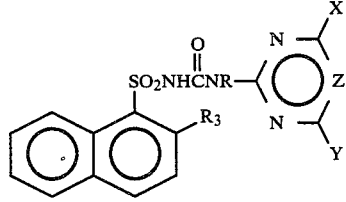

General Structure III

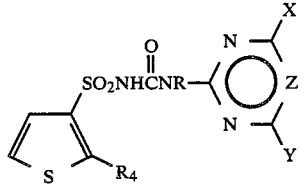

General Structure IV

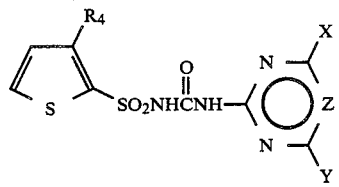

General Structure V

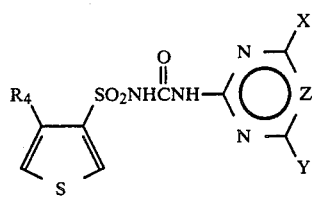

General Structure VI

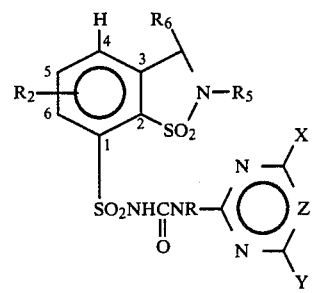

General Structure VIa

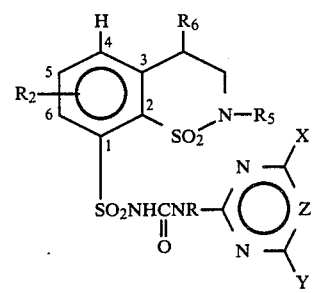

General Structure VII

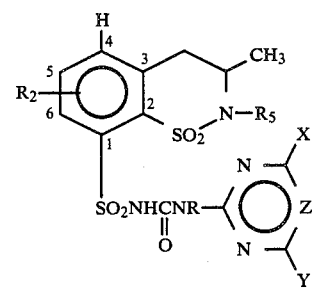

General Structure VIII

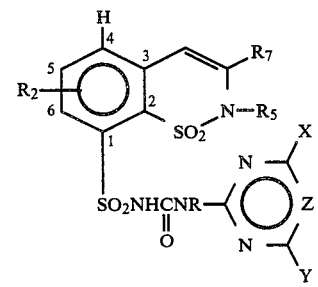

General Structure IX

-continued
General Structures for Tables

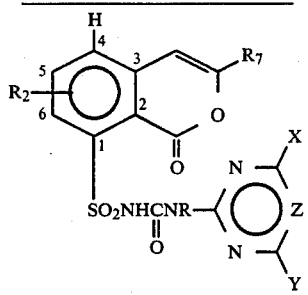

-continued
General Structures for Tables
General Structure X

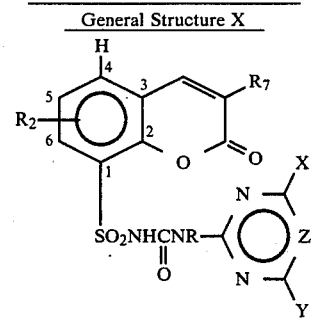

TABLE I

General Structure I

| R₁ | R₂ | R | X | Y | Z | m.p. (°C.) |
|---|---|---|---|---|---|---|
| C₂H₅ | H | H | CH₃ | OCH₂CH₂F | N | |
| C₂H₅ | H | H | CH₃ | OCH₂CHF₂ | N | |
| C₂H₅ | H | H | CH₃ | OCH₂CF₃ | N | |
| C₂H₅ | H | H | CH₃ | OCH₂CH₂F | CH | |
| C₂H₅ | H | H | CH₃ | OCH₂CHF₂ | CH | |
| C₂H₅ | H | H | CH₃ | OCH₂CF₃ | CH | |
| C₂H₅ | H | H | OCH₃ | OCH₂CH₂F | N | |
| C₂H₅ | H | H | OCH₃ | OCH₂CHF₂ | N | |
| C₂H₅ | H | H | OCH₃ | OCH₂CF₃ | N | |
| C₂H₅ | H | H | OCH₃ | OCH₂CH₂F | CH | |
| C₂H₅ | H | H | OCH₃ | OCH₂CHF₂ | CH | |
| C₂H₅ | H | H | OCH₃ | OCH₂CF₃ | CH | |
| CH₂CH₂CH₃ | H | H | OCH₃ | OCH₂CH₂F | CH | |
| CH₂CH₂CH₃ | H | H | OCH₃ | OCH₂CHF₂ | CH | |
| CH₂CH₂CH₃ | H | H | OCH₃ | OCH₂CF₃ | CH | |
| CH₂CH₂CH₃ | H | H | OCH₃ | OCH₂CH₂F | N | |
| CH₂CH₂CH₃ | H | H | OCH₃ | OCH₂CHF₂ | N | |
| CH₂CH₂CH₃ | H | H | OCH₃ | OCH₂CF₃ | N | |
| CH₂CH₂CH₃ | H | H | CH₃ | OCH₂CH₂F | N | |
| CH₂CH₂CH₃ | H | H | CH₃ | OCH₂CHF₂ | N | |
| CH₂CH₂CH₃ | H | H | CH₃ | OCH₂CF₃ | N | |
| CH₂CH₂CH₃ | H | H | CH₃ | OCH₂CH₂F | CH | |
| CH₂CH₂CH₃ | H | H | CH₃ | OCH₂CHF₂ | CH | |
| CH₂CH₂CH₃ | H | H | CH₃ | OCH₂CF₃ | CH | |
| OC₂H₅ | H | H | CH₃ | OCH₂CH₂F | N | 138–142 |
| OC₂H₅ | H | H | CH₃ | OCH₂CHF₂ | N | 125–131(d) |
| OC₂H₅ | H | H | CH₃ | OCH₂CF₃ | N | 132–137 |
| OC₂H₅ | H | H | CH₃ | OCH₂CH₂F | CH | 198–202 |
| OC₂H₅ | H | H | CH₃ | OCH₂CHF₂ | CH | |
| OC₂H₅ | H | H | CH₃ | OCH₂CF₃ | CH | |
| OC₂H₅ | H | H | OCH₃ | OCH₂CH₂F | N | 94–102; 112(d) |
| OC₂H₅ | H | H | OCH₃ | OCH₂CHF₂ | N | |
| OC₂H₅ | H | H | OCH₃ | OCH₂CF₃ | N | 180–181(d) |
| OC₂H₅ | H | H | OCH₃ | OCH₂CH₂F | CH | |
| OC₂H₅ | H | H | OCH₃ | OCH₂CF₂ | CH | |
| OC₂H₅ | H | H | OCH₃ | OCH₂CF₃ | CH | 165–168 |
| OCH₂CH₂CH₃ | H | H | OCH₃ | OCH₂CH₂F | CH | |
| OCH₂CH₂CH₃ | H | H | OCH₃ | OCH₂CHF₂ | CH | |
| OCH₂CH₂CH₃ | H | H | OCH₃ | OCH₂CF₃ | CH | 168–170 |
| OCH₂CH₂CH₃ | H | H | OCH₃ | OCH₂CH₂F | N | 120–124(d) |
| OCH₂CH₂CH₃ | H | H | OCH₃ | OCH₂CHF₂ | N | |
| OCH₂CH₂CH₃ | H | H | OCH₃ | OCH₂CF₃ | N | 161–163(d) |
| OCH₂CH₂CH₃ | H | H | CH₃ | OCH₂CH₂F | N | 139–141(d) |
| OCH₂CH₂CH₃ | H | H | CH₃ | OCH₂CHF₂ | N | |
| OCH₂CH₂CH₃ | H | H | CH₃ | OCH₂CF₃ | N | 121–126(d) |
| OCH₂CH₂CH₃ | H | H | CH₃ | OCH₂CH₂F | CH | 176–179 |
| OCH₂CH₂CH₃ | H | H | CH₃ | OCH₂CHF₂ | CH | |
| OCH₂CH₂CH₃ | H | H | CH₃ | OCH₂CF₃ | CH | |
| CH(CH₃)₂ | H | H | CH₃ | OCH₂CH₂F | N | |
| CH(CH₃)₂ | H | H | CH₃ | OCH₂CHF₂ | N | |
| CH(CH₃)₂ | H | H | CH₃ | OCH₂CF₃ | N | |
| CH(CH₃)₂ | H | H | CH₃ | OCH₂CH₂F | CH | |
| CH(CH₃)₂ | H | H | CH₃ | OCH₂CHF₂ | CH | |
| CH(CH₃)₂ | H | H | CH₃ | OCH₂CF₃ | CH | |
| (CH₂)₃CH₃ | H | H | CH₃ | OCH₂CH₂F | CH | |
| (CH₂)₃CH₃ | H | H | CH₃ | OCH₂CHF₂ | CH | |
| (CH₂)₃CH₃ | H | H | CH₃ | OCH₂CF₃ | CH | |
| (CH₂)₃CH₃ | H | H | CH₃ | OCH₂CH₂F | N | |
| (CH₂)₃CH₃ | H | H | CH₃ | OCH₂CHF₂ | N | |
| (CH₂)₃CH₃ | H | H | CH₃ | OCH₂CF₃ | N | |
| CH₂CH(CH₃)₂ | H | H | CH₃ | OCH₂CH₂F | N | |

TABLE I-continued

General Structure I

| R₁ | R₂ | R | X | Y | Z | m.p. (°C.) |
|---|---|---|---|---|---|---|
| CH₂CH(CH₃)₂ | H | H | CH₃ | OCH₂CHF₂ | N | |
| CH₂CH(CH₃)₂ | H | H | CH₃ | OCH₂CF₃ | N | |
| CH₂CH(CH₃)₂ | H | H | CH₃ | OCH₂CH₂F | CH | |
| CH₂CH(CH₃)₂ | H | H | CH₃ | OCH₂CHF₂ | CH | |
| CH₂CH(CH₃)₂ | H | H | CH₃ | OCH₂CF₃ | CH | |
| CH(CH₃)C₂H₅ | H | H | CH₃ | OCH₂CH₂F | CH | |
| CH(CH₃)C₂H₅ | H | H | CH₃ | OCH₂CHF₂ | CH | |
| CH(CH₃)C₂H₅ | H | H | CH₃ | OCH₂CF₃ | CH | |
| CH(CH₃)C₂H₅ | H | H | CH₃ | OCH₂CH₂F | N | |
| CH(CH₃)C₂H₅ | H | H | CH₃ | OCH₂CHF₂ | N | |
| CH(CH₃)C₂H₅ | H | H | CH₃ | OCH₂CF₃ | N | |
| CH(CH₃)₂ | H | H | OCH₃ | OCH₂CH₂F | N | |
| CH(CH₃)₂ | H | H | OCH₃ | OCH₂CHF₂ | N | |
| CH(CH₃)₂ | H | H | OCH₃ | OCH₂CF₃ | N | |
| CH(CH₃)₂ | H | H | OCH₃ | OCH₂CH₂F | CH | |
| CH(CH₃)₂ | H | H | OCH₃ | OCH₂CHF₂ | CH | |
| CH(CH₃)₂ | H | H | OCH₃ | OCH₂CF₃ | CH | |
| (CH₂)₃CH₃ | H | H | OCH₃ | OCH₂CH₂F | CH | |
| (CH₂)₃CH₃ | H | H | OCH₃ | OCH₂CHF₂ | CH | |
| (CH₂)₃CH₃ | H | H | OCH₃ | OCH₂CF₃ | CH | |
| (CH₂)₃CH₃ | H | H | OCH₃ | OCH₂CH₂F | N | |
| (CH₂)₃CH₃ | H | H | OCH₃ | OCH₂CHF₂ | N | |
| (CH₂)₃CH₃ | H | H | OCH₃ | OCH₂CF₃ | N | |
| CH₂CH(CH₃)₂ | H | H | OCH₃ | OCh₂CH₂F | N | |
| CH₂CH(CH₃)₂ | H | H | OCH₃ | OCH₂CHF₂ | N | |
| CH₂CH(CH₃)₂ | H | H | OCH₃ | OCH₂CF₃ | N | |
| CH₂CH(CH₃)₂ | H | H | OCH₃ | OCH₂CH₂F | CH | |
| CH₂CH(CH₃)₂ | H | H | OCH₃ | OCH₂CHF₂ | CH | |
| CH₂CH(CH₃)₂ | H | H | OCH₃ | OCH₂CF₃ | CH | |
| CH(CH₃)C₂H₅ | H | H | OCH₃ | OCH₂CH₂F | CH | |
| CH(CH₃)C₂H₅ | H | H | OCH₃ | OCH₂CHF₂ | CH | |
| CH(CH₃)C₂H₅ | H | H | OCH₃ | OCH₂CF₃ | CH | |
| CH(CH₃)C₂H₅ | H | H | OCH₃ | OCH₂CH₂F | N | |
| CH(CH₃)C₂H₅ | H | H | OCH₃ | OCH₂CHF₂ | N | |
| CH(CH₃)C₂H₅ | H | H | OCH₃ | OCH₂CF₃ | N | |
| OCH(CH₃)₂ | H | H | CH₃ | OCH₂CH₂F | N | |
| OCH(CH₃)₂ | H | H | CH₃ | OCH₂CHF₂ | N | |
| OCH(CH₃)₂ | H | H | CH₃ | OCH₂CF₃ | N | |
| OCH(CH₃)₂ | H | H | CH₃ | OCH₂CH₂F | CH | |
| OCH(CH₃)₂ | H | H | CH₃ | OCH₂CHF₂ | CH | |
| OCH(CH₃)₂ | H | H | CH₃ | OCH₂CF₃ | CH | |
| O(CH₂)₃CH₃ | H | H | CH₃ | OCH₂CH₂F | CH | |
| O(CH₂)₃CH₃ | H | H | CH₃ | OCH₂CHF₂ | CH | |
| O(CH₂)₃CH₃ | H | H | CH₃ | OCH₂CF₃ | CH | |
| O(CH₂)₃CH₃ | H | H | CH₃ | OCH₂CH₂F | N | |
| O(CH₂)₃CH₃ | H | H | CH₃ | OCH₂CHF₂ | N | |
| O(CH₂)₃CH₃ | H | H | CH₃ | OCH₂CF₃ | N | |
| OCH₂CH(CH₃)₂ | H | H | CH₃ | OCH₂CH₂F | N | |
| OCH₂CH(CH₃)₂ | H | H | CH₃ | OCH₂CHF₂ | N | |
| OCH₂CH(CH₃)₂ | H | H | CH₃ | OCH₂CF₃ | N | |
| OCH₂CH(CH₃)₂ | H | H | CH₃ | OCH₂CH₂F | CH | |
| OCH₂CH(CH₃)₂ | H | H | CH₃ | OCH₂CHF₂ | CH | |
| OCH₂CH(CH₃)₂ | H | H | CH₃ | OCH₂CF₃ | CH | |
| OCH(CH₃)C₂H₅ | H | H | CH₃ | OCH₂CH₂F | CH | |
| OCH(CH₃)C₂H₅ | H | H | CH₃ | OCH₂CHF₂ | CH | |
| OCH(CH₃)C₂H₅ | H | H | CH₃ | OCH₂CF₃ | CH | |
| OCH(CH₃)C₂H₅ | H | H | CH₃ | OCH₂CH₂F | N | |
| OCH(CH₃)C₂H₅ | H | H | CH₃ | OCH₂CHF₂ | N | |
| OCH(CH₃)C₂H₅ | H | H | CH₃ | OCH₂CF₃ | N | |
| OCH(CH₃)₂ | H | H | OCH₃ | OCH₂CH₂F | N | |
| OCH(CH₃)₂ | H | H | OCH₃ | OCH₂CHF₂ | N | |
| OCH(CH₃)₂ | H | H | OCH₃ | OCH₂CF₃ | N | |
| OCH(CH₃)₂ | H | H | OCH₃ | OCH₂CH₂F | CH | |
| OCH(CH₃)₂ | H | H | OCH₃ | OCH₂CHF₂ | CH | |
| OCH(CH₃)₂ | H | H | OCH₃ | OCH₂CF₃ | CH | |
| O(CH₂)₃CH₃ | H | H | OCH₃ | OCH₂CH₂F | CH | |
| O(CH₂)₃CH₃ | H | H | OCH₃ | OCH₂CHF₂ | CH | |
| O(CH₂)₃CH₃ | H | H | OCH₃ | OCH₂CF₃ | CH | |
| O(CH₂)₃CH₃ | H | H | OCH₃ | OCH₂CH₂F | N | |
| O(CH₂)₃CH₃ | H | H | OCH₃ | OCH₂CHF₂ | N | |
| O(CH₂)₃CH₃ | H | H | OCH₃ | OCH₂CF₃ | N | |
| OCH₂CH(CH₃)₂ | H | H | OCH₃ | OCH₂CH₂F | N | |
| OCH₂CH(CH₃)₂ | H | H | OCH₃ | OCH₂CHF₂ | N | |
| OCH₂CH(CH₃)₂ | H | H | OCH₃ | OCH₂CF₃ | N | |
| OCH₂CH(CH₃)₂ | H | H | OCH₃ | OCH₂CH₂F | CH | |
| OCH₂CH(CH₃)₂ | H | H | OCH₃ | OCH₂CHF₂ | CH | |
| OCH₂CH(CH₃)₂ | H | H | OCH₃ | OCH₂CF₃ | CH | |
| OCH(CH₃)C₂H₅ | H | H | OCH₃ | OCH₂CH₂F | CH | |
| OCH(CH₃)C₂H₅ | H | H | OCH₃ | OCH₂CHF₂ | CH | |
| OCH(CH₃)C₂H₅ | H | H | OCH₃ | OCH₂CF₃ | CH | |

TABLE I-continued

General Structure I

| R₁ | R₂ | R | X | Y | Z | m.p. (°C.) |
|---|---|---|---|---|---|---|
| OCH(CH₃)C₂H₅ | H | H | OCH₃ | OCH₂CH₂F | N | |
| OCH(CH₃)C₂H₅ | H | H | OCH₃ | OCH₂CHF₂ | N | |
| OCH(CH₃)C₂H₅ | H | H | OCH₃ | OCH₂CF₃ | N | |
| OC(CH₃)₃ | H | H | CH₃ | OCH₂CH₂F | N | |
| OC(CH₃)₃ | H | H | CH₃ | OCH₂CHF₂ | N | |
| OC(CH₃)₃ | H | H | CH₃ | OCH₂CF₃ | N | |
| OC(CH₃)₃ | H | H | CH₃ | OCH₂CH₂F | CH | |
| OC(CH₃)₃ | H | H | CH₃ | OCH₂CHF₂ | CH | |
| OC(CH₃)₃ | H | H | CH₃ | OCH₂CF₃ | CH | |
| OC(CH₃)₃ | H | H | OCH₃ | OCH₂CH₂F | N | |
| OC(CH₃)₃ | H | H | OCH₃ | OCH₂CHF₂ | N | |
| OC(CH₃)₃ | H | H | OCH₃ | OCH₂CF₃ | N | |
| OC(CH₃)₃ | H | H | OCH₃ | OCH₂CH₂F | CH | |
| OC(CH₃)₃ | H | H | OCH₃ | OCH₂CHF₂ | CH | |
| OC(CH₃)₃ | H | H | OCH₃ | OCH₂CF₃ | CH | |
| C(CH₃)₃ | H | H | OCH₃ | OCH₂CH₂F | CH | |
| C(CH₃)₃ | H | H | OCH₃ | OCH₂CHF₂ | CH | |
| C(CH₃)₃ | H | H | OCH₃ | OCH₂CF₃ | CH | |
| C(CH₃)₃ | H | H | OCH₃ | OCH₂CH₂F | N | |
| C(CH₃)₃ | H | H | OCH₃ | OCH₂CHF₂ | N | |
| C(CH₃)₃ | H | H | OCH₃ | OCH₂CF₃ | N | |
| C(CH₃)₃ | H | H | CH₃ | OCH₂CH₂F | N | |
| C(CH₃)₃ | H | H | CH₃ | OCH₂CHF₂ | N | |
| C(CH₃)₃ | H | H | CH₃ | OCH₂CF₃ | N | |
| C(CH₃)₃ | H | H | CH₃ | OCH₂CH₂F | CH | |
| C(CH₃)₃ | H | H | CH₃ | OCH₂CHF₂ | CH | |
| C(CH₃)₃ | H | H | CH₃ | OCH₂CF₃ | CH | |
| SO₂N(CH₃)₂ | H | H | CH₃ | OCH₂CH₂F | N | 159–164(d) |
| SO₂N(CH₃)₂ | H | H | CH₃ | OCH₂CHF₂ | N | |
| SO₂N(CH₃)₂ | H | H | CH₃ | OCH₂CH₂F | CH | |
| SO₂N(CH₃)₂ | H | H | CH₃ | OCH₂CHF₂ | CH | |
| SO₂N(CH₃)₂ | H | H | OCH₃ | OCH₂CH₂F | N | 152–156 |
| SO₂N(CH₃)₂ | H | H | OCH₃ | OCH₂CHF₂ | N | |
| SO₂N(CH₃)₂ | H | H | OCH₃ | OCH₂CH₂F | CH | |
| SO₂N(CH₃)₂ | H | H | OCH₃ | OCH₂CHF₂ | CH | |
| SO₂N(C₃H₅)₂ | H | H | OCH₃ | OCH₂CH₂F | CH | |
| SO₂N(C₃H₅)₂ | H | H | OCH₃ | OCH₂CHF₂ | CH | |
| SO₂N(C₃H₅)₂ | H | H | OCH₃ | OCH₂CH₂F | N | |
| SO₂N(C₃H₅)₂ | H | H | OCH₃ | OCH₂CHF₂ | N | |
| SO₂N(C₃H₅)₂ | H | H | CH₃ | OCH₂CH₂F | N | |
| SO₂N(C₃H₅)₂ | H | H | CH₃ | OCH₂CHF₂ | N | |
| SO₂N(C₃H₅)₂ | H | H | CH₃ | OCH₂CH₂F | CH | |
| SO₂N(C₃H₅)₂ | H | H | CH₃ | OCH₂CHF₂ | CH | |
| SO₂N(CH₃)CH(CH₃)₂ | H | H | CH₃ | OCH₂CH₂F | N | |
| SO₂N(CH₃)CH(CH₃)₂ | H | H | CH₃ | OCH₂CHF₂ | N | |
| SO₂N(CH₃)CH(CH₃)₂ | H | H | CH₃ | OCH₂CH₂F | CH | |
| SO₂N(CH₃)CH(CH₃)₂ | H | H | CH₃ | OCH₂CHF₂ | CH | |
| SO₂N(CH₃)CH₂CH₂CH₃ | H | H | CH₃ | OCH₂CH₂F | CH | |
| SO₂N(CH₃)CH₂CH₂CH₃ | H | H | CH₃ | OCH₂CHF₂ | CH | |
| SO₂N(CH₃)CH₂CH₂CH₃ | H | H | CH₃ | OCH₂CH₂F | N | |
| SO₂N(CH₃)CH₂CH₂CH₃ | H | H | CH₃ | OCH₂CHF₂ | N | |
| SO₂N(OCH₃)CH₃ | H | H | CH₃ | OCH₂CH₂F | N | |
| SO₂N(OCH₃)CH₃ | H | H | CH₃ | OCH₂CHF₂ | N | |
| SO₂N(OCH₃)CH₃ | H | H | CH₃ | OCH₂CH₂F | CH | |
| SO₂N(OCH₃)CH₃ | H | H | CH₃ | OCH₂CHF₂ | CH | |
| SO₂N(CH₃)₂ | 5-OCH₃ | H | CH₃ | OCH₂CH₂F | CH | |
| SO₂N(CH₃)₂ | 5-OCH₃ | H | CH₃ | OCH₂CHF₂ | CH | |
| SO₂N(CH₃)₂ | 5-OCH₃ | H | CH₃ | OCH₂CH₂F | N | |
| SO₂N(CH₃)₂ | 5-OCH₃ | H | CH₃ | OCH₂CHF₂ | N | |
| SO₂N(CH₃)CH(CH₃)₂ | H | H | OCH₃ | OCH₂CH₂F | N | |
| SO₂N(CH₃)CH(CH₃)₂ | H | H | OCH₃ | OCH₂CHF₂ | N | |
| SO₂N(CH₃)CH(CH₃)₂ | H | H | OCH₃ | OCH₂CH₂F | CH | |
| SO₂N(CH₃)CH(CH₃)₂ | H | H | OCH₃ | OCH₂CHF₂ | CH | |
| SO₂N(CH₃)CH₂CH₂CH₃ | H | H | OCH₃ | OCH₂CH₂F | CH | |
| SO₂N(CH₃)CH₂CH₂CH₃ | H | H | OCH₃ | OCH₂CHF₂ | CH | |
| SO₂N(CH₃)CH₂CH₂CH₃ | H | H | OCH₃ | OCH₂CH₂F | N | |
| SO₂N(CH₃)CH₂CH₂CH₃ | H | H | OCH₃ | OCH₂CHF₂ | N | |
| SO₂N(OCH₃)CH₃ | H | H | OCH₃ | OCH₂CH₂F | N | |
| SO₂N(OCH₃)CH₃ | H | H | OCH₃ | OCH₂CHF₂ | N | |
| SO₂N(OCH₃)CH₃ | H | H | OCH₃ | OCH₂CH₂F | CH | |
| SO₂N(OCH₃)CH₃ | H | H | OCH₃ | OCH₂CHF₂ | CH | |
| SO₂N(CH₃)₂ | 5-OCH₃ | H | OCH₃ | OCH₂CH₂F | CH | |
| SO₂N(CH₃)₂ | 5-OCH₃ | H | OCH₃ | OCH₂CHF₂ | CH | |
| SO₂N(CH₃)₂ | 5-OCH₃ | H | OCH₃ | OCH₂CH₂F | N | |
| SO₂N(CH₃)₂ | 5-OCH₃ | H | OCH₃ | OCH₂CHF₂ | N | |
| C₂H₅ | 5-OCH₃ | H | CH₃ | OCH₂CH₂F | N | |
| C₂H₅ | 5-OCH₃ | H | CH₃ | OCH₂CHF₂ | N | |
| C₂H₅ | 5-OCH₃ | H | CH₃ | OCH₂CF₃ | N | |
| C₂H₅ | 5-OCH₃ | H | CH₃ | OCH₂CH₂F | CH | |
| C₂H₅ | 5-OCH₃ | H | CH₃ | OCH₂CHF₂ | CH | |

TABLE I-continued

General Structure I

| R₁ | R₂ | R | X | Y | Z | m.p. (°C.) |
|---|---|---|---|---|---|---|
| C₂H₅ | 5-OCH₃ | H | CH₃ | OCH₂CF₃ | CH | |
| C₂H₅ | 5-OCH₃ | H | OCH₃ | OCH₂CH₂F | N | |
| C₂H₅ | 5-OCH₃ | H | OCH₃ | OCH₂CHF₂ | N | |
| C₂H₅ | 5-OCH₃ | H | OCH₃ | OCH₂CF₃ | N | |
| C₂H₅ | 5-OCH₃ | H | OCH₃ | OCH₂CH₂F | CH | |
| C₂H₅ | 5-OCH₃ | H | OCH₃ | OCH₂CHF₂ | CH | |
| C₂H₅ | 5-OCH₃ | H | OCH₃ | OCH₂CF₃ | CH | |
| CH₂CH₂CH₃ | 5-Cl | H | OCH₃ | OCH₂CH₂F | CH | |
| CH₂CH₂CH₃ | 5-Cl | H | OCH₃ | OCH₂CHF₂ | CH | |
| CH₂CH₂CH₃ | 5-Cl | H | OCH₃ | OCH₂CF₃ | CH | |
| CH₂CH₂CH₃ | 5-Cl | H | OCH₃ | OCH₂CH₂F | N | |
| CH₂CH₂CH₃ | 5-Cl | H | OCH₃ | OCH₂CHF₂ | N | |
| CH₂CH₂CH₃ | 5-Cl | H | OCH₃ | OCH₂CF₃ | N | |
| CH₂CH₂CH₃ | 5-Cl | H | CH₃ | OCH₂CH₂F | N | |
| CH₂Ch₂CH₃ | 5-Cl | H | CH₃ | OCH₂CHF₂ | N | |
| CH₂CH₂CH₃ | 5-Cl | H | CH₃ | OCH₂CF₃ | N | |
| CH₂CH₂CH₃ | 5-Cl | H | CH₃ | OCH₂CH₂F | CH | |
| CH₂CH₂CH₃ | 5-Cl | H | CH₃ | OCH₂CHF₂ | CH | |
| CH₂CH₂CH₃ | 5-Cl | H | CH₃ | OCH₂CF₃ | CH | |
| OC₂H₅ | 5-OCH₃ | H | CH₃ | OCH₂CH₂F | N | |
| OC₂H₅ | 5-OCH₃ | H | CH₃ | OCH₂CHF₂ | N | |
| OC₂H₅ | 5-OCH₃ | H | CH₃ | OCH₂CF₃ | N | |
| OC₂H₅ | 5-OCH₃ | H | CH₃ | OCH₂CH₂F | CH | |
| OC₂H₅ | 5-OCH₃ | H | CH₃ | OCH₂CHF₂ | CH | |
| OC₂H₅ | 5-OCH₃ | H | CH₃ | OCH₂CF₃ | CH | |
| OC₂H₅ | 5-OCH₃ | H | OCH₃ | OCH₂CH₂F | N | |
| OC₂H₅ | 5-OCH₃ | H | OCH₃ | OCH₂CHF₂ | N | |
| OC₂H₅ | 5-OCH₃ | H | OCH₃ | OCH₂CF₃ | N | |
| OC₂H₅ | 5-OCH₃ | H | OCH₃ | OCH₂CH₂F | CH | |
| OC₂H₅ | 5-OCH₃ | H | OCH₃ | OCH₂CHF₂ | CH | |
| OC₂H₅ | 5-OCH₃ | H | OCH₃ | OCH₂CF₃ | CH | |
| OCH₂CH₂CH₃ | 5-OCH₃ | H | OCH₃ | OCH₂CH₂F | CH | |
| OCH₂CH₂CH₃ | 5-OCH₃ | H | OCH₃ | OCH₂CHF₂ | CH | |
| OCH₂CH₂CH₃ | 5-OCH₃ | H | OCH₃ | OCH₂CF₃ | CH | |
| OCH₂CH₂CH₃ | 5-OCH₃ | H | OCH₃ | OCH₂CH₂F | N | |
| OCH₂CH₂CH₃ | 5-OCH₃ | H | OCH₃ | OCH₂CHF₂ | N | |
| OCH₂CH₂CH₃ | 5-OCH₃ | H | OCH₃ | OCH₂CF₃ | N | |
| OCH₂CH₂CH₃ | 5-OCH₃ | H | CH₃ | OCH₂CH₂F | N | |
| OCH₂CH₂CH₃ | 5-OCH₃ | H | CH₃ | OCH₂CHF₂ | N | |
| OCH₂CH₂CH₃ | 5-OCH₃ | H | CH₃ | OCH₂CF₃ | N | |
| OCH₂CH₂CH₃ | 5-OCH₃ | H | CH₃ | OCH₂CH₂F | CH | |
| OCH₂CH₂CH₃ | 5-OCH₃ | H | CH₃ | OCH₂CHF₂ | CH | |
| OCH₂CH₂CH₃ | 5-OCH₃ | H | CH₃ | OCH₂CF₃ | CH | |
| OC₂H₅ | 5-Cl | H | CH₃ | OCH₂CH₂F | N | |
| OC₂H₅ | 5-Cl | H | CH₃ | OCH₂CHF₂ | N | |
| OC₂H₅ | 5-Cl | H | CH₃ | OCH₂CF₃ | N | |
| OC₂H₅ | 5-Cl | H | CH₃ | OCH₂CH₂F | CH | |
| OC₂H₅ | 5-Cl | H | CH₃ | OCH₂CHF₂ | CH | |
| OC₂H₅ | 5-Cl | H | CH₃ | OCH₂CF₃ | CH | |
| OC₂H₅ | 5-Cl | H | OCH₃ | OCH₂CH₂F | N | |
| OC₂H₅ | 5-Cl | H | OCH₃ | OCH₂CHF₂ | N | |
| OC₂H₅ | 5-Cl | H | OCH₃ | OCH₂CF₃ | N | |
| OC₂H₅ | 5-Cl | H | OCH₃ | OCH₂CH₂F | CH | |
| OC₂H₅ | 5-Cl | H | OCH₃ | OCH₂CHF₂ | CH | |
| OC₂H₅ | 5-Cl | H | OCH₃ | OCH₂CF₃ | CH | |
| OCH₂CH₂CH₃ | 5-CF₃ | H | OCH₃ | OCH₂CH₂F | CH | |
| OCH₂CH₂CH₃ | 5-CF₃ | H | OCH₃ | OCH₂CHF₂ | CH | |
| OCH₂CH₂CH₃ | 5-CF₃ | H | OCH₃ | OCH₂CF₃ | CH | |
| OCH₂CH₂CH₃ | 5-CF₃ | H | OCH₃ | OCH₂CH₂F | N | |
| OCH₂CH₂CH₃ | 5-CF₃ | H | OCH₃ | OCH₂CHF₂ | N | |
| OCH₂CH₂CH₃ | 5-CF₃ | H | OCH₃ | OCH₂CF₃ | N | |
| OCH₂CH₂CH₃ | 5-CF₃ | H | CH₃ | OCH₂CH₂F | N | |
| OCH₂CH₂CH₃ | 5-CF₃ | H | CH₃ | OCH₂CHF₂ | N | |
| OCH₂CH₂CH₃ | 5-CF₃ | H | CH₃ | OCH₂CF₃ | N | |
| OCH₂CH₂CH₃ | 5-CF₃ | H | CH₃ | OCH₂CH₂F | CH | |
| OCH₂CH₂CH₃ | 5-CF₃ | H | CH₃ | OCH₂CHF₂ | CH | |
| OCH₂CH₂CH₃ | 5-CF₃ | H | CH₃ | OCH₂CF₃ | CH | |
| OC₂H₅ | 5-SCH₃ | H | CH₃ | OCH₂CH₂F | N | |
| OC₂H₅ | 5-SCH₃ | H | CH₃ | OCH₂CHF₂ | N | |
| OC₂H₅ | 5-SCH₃ | H | CH₃ | OCH₂CF₃ | N | |
| OC₂H₅ | 5-SCH₃ | H | CH₃ | OCH₂CH₂F | CH | |
| OC₂H₅ | 5-SCH₃ | H | CH₃ | OCH₂CHF₂ | CH | |
| OC₂H₅ | 5-SCH₃ | H | CH₃ | OCH₂CF₃ | CH | |
| OC₂H₅ | 5-SCH₃ | H | OCH₃ | OCH₂CH₂F | N | |
| OC₂H₅ | 5-SCH₃ | H | OCH₃ | OCH₂CHF₂ | N | |
| OC₂H₅ | 5-SCH₃ | H | OCH₃ | OCH₂CF₃ | N | |
| OC₂H₅ | 5-SCH₃ | H | OCH₃ | OCH₂CH₂F | CH | |
| OC₂H₅ | 5-SCH₃ | H | OCH₃ | OCH₂CHF₂ | CH | |
| OC₂H₅ | 5-SCH₃ | H | OCH₃ | OCH₂CF₃ | CH | |
| OC₂H₅ | 5-Br | H | OCH₃ | OCH₂CH₂F | CH | |

TABLE I-continued

General Structure I

| R₁ | R₂ | R | X | Y | Z | m.p. (°C.) |
|---|---|---|---|---|---|---|
| OC₂H₅ | 5-Br | H | OCH₃ | OCH₂CHF₂ | CH | |
| OC₂H₅ | 5-Br | H | OCH₃ | OCH₂CF₃ | CH | |
| OC₂H₅ | 5-Br | H | OCH₃ | OCH₂CH₂F | N | |
| OC₂H₅ | 5-Br | H | OCH₃ | OCH₂CHF₂ | N | |
| OC₂H₅ | 5-Br | H | OCH₃ | OCH₂CF₃ | N | |
| OC₂H₅ | 5-Br | H | CH₃ | OCH₂CH₂F | N | |
| OC₂H₅ | 5-Br | H | CH₃ | OCH₂CHF₂ | N | |
| OC₂H₅ | 5-Br | H | CH₃ | OCH₂CF₃ | N | |
| OC₂H₅ | 5-Br | H | CH₃ | OCH₂CH₂F | CH | |
| OC₂H₅ | 5-Br | H | CH₃ | OCH₂CHF₂ | CH | |
| OC₂H₅ | 5-Br | H | CH₃ | OCH₂CF₃ | CH | |
| OC₂H₅ | 5-F | H | CH₃ | OCH₂CH₂F | N | |
| OC₂H₅ | 5-F | H | CH₃ | OCH₂CHF₂ | N | |
| OC₂H₅ | 5-F | H | CH₃ | OCH₂CF₃ | N | |
| OC₂H₅ | 5-F | H | CH₃ | OCH₂CH₂F | CH | |
| OC₂H₅ | 5-F | H | CH₃ | OCH₂CHF₂ | CH | |
| OC₂H₅ | 5-F | H | CH₃ | OCH₂CF₃ | CH | |
| OC₂H₅ | 5-F | H | OCH₃ | OCH₂CH₂F | N | |
| OC₂H₅ | 5-F | H | OCH₃ | OCH₂CHF₂ | N | |
| OC₂H₅ | 5-F | H | OCH₃ | OCH₂CF₃ | N | |
| OC₂H₅ | 5-F | H | OCH₃ | OCH₂CH₂F | CH | |
| OC₂H₅ | 5-F | H | OCH₃ | OCH₂CHF₂ | CH | |
| OC₂H₅ | 5-F | H | OCH₃ | OCH₂CF₃ | CH | |
| OCH₂CH₂CH₃ | 5-F | H | OCH₃ | OCH₂CH₂F | CH | |
| OCH₂CH₂CH₃ | 5-F | H | OCH₃ | OCH₂CHF₂ | CH | |
| OCH₂CH₂CH₃ | 5-F | H | OCH₃ | OCH₂CF₃ | CH | |
| OCH₂CH₂CH₃ | 5-F | H | OCH₃ | OCH₂CH₂F | N | |
| OCH₂CH₂CH₃ | 5-F | H | OCH₃ | OCH₂CHF₂ | N | |
| OCH₂CH₂CH₃ | 5-F | H | OCH₃ | OCH₂CF₃ | N | |
| OCH₂CH₂CH₃ | 5-F | H | CH₃ | OCH₂CH₂F | N | |
| OCH₂CH₂CH₃ | 5-F | H | CH₃ | OCH₂CHF₂ | N | |
| OCH₂CH₂CH₃ | 5-F | H | CH₃ | OCH₂CF₃ | N | |
| OCH₂CH₂CH₃ | 5-F | H | CH₃ | OCH₂CH₂F | CH | |
| OCH₂CH₂CH₃ | 5-F | H | CH₃ | OCH₂CHF₂ | CH | |
| OCH₂CH₂CH₃ | 5-F | H | CH₃ | OCH₂CF₃ | CH | |
| OC₂H₅ | 5-CH₃ | H | CH₃ | OCH₂CH₂F | N | |
| OC₂H₅ | 5-CH₃ | H | CH₃ | OCH₂CHF₂ | N | |
| OC₂H₅ | 5-CH₃ | H | CH₃ | OCH₂CF₃ | N | |
| OC₂H₅ | 5-CH₃ | H | CH₃ | OCH₂CH₂F | CH | |
| OC₂H₅ | 5-CH₃ | H | CH₃ | OCH₂CHF₂ | CH | |
| OC₂H₅ | 5-CH₃ | H | CH₃ | OCH₂CF₃ | CH | |
| OC₂H₅ | 5-CH₃ | H | OCH₃ | OCH₂CH₂F | N | |
| OC₂H₅ | 5-CH₃ | H | OCH₃ | OCH₂CHF₂ | N | |
| OC₂H₅ | 5-CH₃ | H | OCH₃ | OCH₂CF₃ | N | |
| OC₂H₅ | 5-CH₃ | H | OCH₃ | OCH₂CH₂F | CH | |
| OC₂H₅ | 5-CH₃ | H | OCH₃ | OCH₂CHF₂ | CH | |
| OC₂H₅ | 5-CH₃ | H | OCH₃ | OCH₂CF₃ | CH | |
| OCH₂CH₂CH₃ | 5-CH₃ | H | OCH₃ | OCH₂CH₂F | CH | |
| OCH₂CH₂CH₃ | 5-CH₃ | H | OCH₃ | OCH₂CHF₂ | CH | |
| OCH₂CH₂CH₃ | 5-CH₃ | H | OCH₃ | OCH₂CF₃ | CH | |
| OCH₂CH₂CH₃ | 5-CH₃ | H | OCH₃ | OCH₂CH₂F | N | |
| OCH₂CH₂CH₃ | 5-CH₃ | H | OCH₃ | OCH₂CHF₂ | N | |
| OCH₂CH₂CH₃ | 5-CH₃ | H | OCH₃ | OCH₂CF₃ | N | |
| OCH₂CH₂CH₃ | 5-CH₃ | H | CH₃ | OCH₂CH₂F | N | |
| OCH₂CH₂CH₃ | 5-CH₃ | H | CH₃ | OCH₂CHF₂ | N | |
| OCH₂CH₂CH₃ | 5-CH₃ | H | CH₃ | OCH₂CF₃ | N | |
| OCH₂CH₂CH₃ | 5-CH₃ | H | CH₃ | OCH₂CH₂F | CH | |
| OCH₂CH₂CH₃ | 5-CH₃ | H | CH₃ | OCH₂CHF₂ | CH | |
| OCH₂CH₂CH₃ | 5-CH₃ | H | CH₃ | OCH₂CF₃ | CH | |
| OC₂H₅ | 3-Cl | H | CH₃ | OCH₂CH₂F | N | |
| OC₂H₅ | 3-Cl | H | CH₃ | OCH₂CF₃ | N | |
| OC₂H₅ | 3-Cl | H | CH₃ | OCH₂CF₃ | CH | |
| OC₂H₅ | 3-Cl | H | CH₃ | OCH₂CH₂F | CH | |
| C₂H₅ | 6-Cl | H | CH₃ | OCH₂CH₂F | CH | |
| C₂H₅ | 6-Cl | H | CH₃ | OCH₂CF₃ | CH | |
| C₂H₅ | 6-Cl | H | OCH₃ | OCH₂CH₂F | N | |
| C₂H₅ | 6-Cl | H | OCH₃ | OCH₂CF₃ | N | |
| 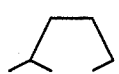 | | H | OCH₃ | OCH₂CH₂F | N | |
| 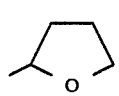 | | H | OCH₃ | OCH₂CHF₂ | N | |

TABLE I-continued

General Structure I

| R₁ | R₂ | R | X | Y | Z | m.p. (°C.) |
|---|---|---|---|---|---|---|
| tetrahydrofuran-2-yl | H | H | CH₃ | OCH₂CH₂F | N | |
| tetrahydrofuran-2-yl | H | H | CH₃ | OCH₂CH₂F | CH | |
| tetrahydrofuran-2-yl | H | H | OCH₃ | OCH₂CH₂F | CH | |
| C₂H₅ | H | H | CH₃ | CH₃ | OCH₂CH₂F | N |
| C₂H₅ | H | H | CH₃ | CH₃ | OCH₂CHF₂ | N |
| C₂H₅ | H | H | CH₃ | CH₃ | OCH₂CF₃ | N |
| C₂H₅ | H | H | CH₃ | CH₃ | OCH₂CH₂F | CH |
| C₂H₅ | H | H | CH₃ | CH₃ | OCH₂CHF₂ | CH |
| C₂H₅ | H | H | CH₃ | CH₃ | OCH₂CF₃ | CH |
| C₂H₅ | H | H | CH₃ | OCH₃ | OCH₂CH₂F | N |
| C₂H₅ | H | H | CH₃ | OCH₃ | OCH₂CHF₂ | N |
| C₂H₅ | H | H | CH₃ | OCH₃ | OCH₂CF₃ | N |
| C₂H₅ | H | H | CH₃ | OCH₃ | OCH₂CH₂F | CH |
| C₂H₅ | H | H | CH₃ | OCH₃ | OCH₂CHF₂ | CH |
| C₂H₅ | H | H | CH₃ | OCH₃ | OCH₂CF₃ | CH |
| CH₂CH₂CH₃ | H | H | CH₃ | OCH₃ | OCH₂CH₂F | CH |
| CH₂CH₂CH₃ | H | H | CH₃ | OCH₃ | OCH₂CHF₂ | CH |
| CH₂CH₂CH₃ | H | H | CH₃ | OCH₃ | OCH₂CF₃ | CH |
| CH₂CH₂CH₃ | H | H | CH₃ | OCH₃ | OCH₂CH₂F | N |
| CH₂CH₂CH₃ | H | H | CH₃ | OCH₃ | OCH₂CHF₂ | N |
| CH₂CH₂CH₃ | H | H | CH₃ | OCH₃ | OCH₂CF₃ | N |
| CH₂CH₂CH₃ | H | H | CH₃ | CH₃ | OCH₂CH₂F | N |
| CH₂CH₂CH₃ | H | H | CH₃ | CH₃ | OCH₂CHF₂ | N |
| CH₂CH₂CH₃ | H | H | CH₃ | CH₃ | OCH₂CF₃ | N |
| CH₂CH₂CH₃ | H | H | CH₃ | CH₃ | OCH₂CH₂F | CH |
| CH₂CH₂CH₃ | H | H | CH₃ | CH₃ | OCH₂CHF₂ | CH |
| CH₂CH₂CH₃ | H | H | CH₃ | CH₃ | OCH₂CF₃ | CH |
| CH(CH₃)₂ | H | H | CH₃ | CH₃ | OCH₂CH₂F | N |
| CH(CH₃)₂ | H | H | CH₃ | CH₃ | OCH₂CHF₂ | N |
| CH(CH₃)₂ | H | H | CH₃ | CH₃ | OCH₂CF₃ | N |
| CH(CH₃)₂ | H | H | CH₃ | CH₃ | OCH₂CH₂F | CH |
| CH(CH₃)₂ | H | H | CH₃ | CH₃ | OCH₂CHF₂ | CH |
| CH(CH₃)₂ | H | H | CH₃ | CH₃ | OCH₂CF₃ | CH |
| (CH₂)₃CH₃ | H | H | CH₃ | CH₃ | OCH₂CH₂F | CH |
| (CH₂)₃CH₃ | H | H | CH₃ | CH₃ | OCH₂CHF₂ | CH |
| (CH₂)₃CH₃ | H | H | CH₃ | CH₃ | OCH₂CF₃ | CH |
| (CH₂)₃CH₃ | H | H | CH₃ | CH₃ | OCH₂CH₂F | N |
| (CH₂)₃CH₃ | H | H | CH₃ | CH₃ | OCH₂CHF₂ | N |
| (CH₂)₃CH₃ | H | H | CH₃ | CH₃ | OCH₂CF₃ | N |
| CH₂CH(CH₃)₂ | H | H | CH₃ | CH₃ | OCH₂CH₂F | N |
| CH₂CH(CH₃)₂ | H | H | CH₃ | CH₃ | OCH₂CHF₂ | N |
| CH₂CH(CH₃)₂ | H | H | CH₃ | CH₃ | OCH₂CF₃ | N |
| CH₂CH(CH₃)₂ | H | H | CH₃ | CH₃ | OCH₂CH₂F | CH |
| CH₂CH(CH₃)₂ | H | H | CH₃ | CH₃ | OCH₂CHF₂ | CH |
| CH₂CH(CH₃)₂ | H | H | CH₃ | CH₃ | OCH₂CF₃ | CH |
| CH(CH₃)C₂H₅ | H | H | CH₃ | CH₃ | OCH₂CH₂F | CH |
| CH(CH₃)C₂H₅ | H | H | CH₃ | CH₃ | OCH₂CHF₂ | CH |
| CH(CH₃)C₂H₅ | H | H | CH₃ | CH₃ | OCH₂CF₃ | CH |
| CH(CH₃)C₂H₅ | H | H | CH₃ | CH₃ | OCH₂CH₂F | N |
| CH(CH₃)C₂H₅ | H | H | CH₃ | CH₃ | OCH₂CHF₂ | N |
| CH(CH₃)C₂H₅ | H | H | CH₃ | CH₃ | OCH₂CF₃ | N |

Note: The first three rows of R₁ show a tetrahydrofuran-2-yl (2-oxolanyl) substituent drawn as a five-membered ring containing oxygen.

TABLE II

General Structure II

| R₃ | R | X | Y | Z | m.p.(°C.) |
|---|---|---|---|---|---|
| H | H | CH₃ | OCH₂CH₂F | CH | |
| H | H | CH₃ | OCH₂CF₃ | CH | |
| H | H | CH₃ | OCH₂CHF₂ | CH | |
| H | H | OCH₃ | OCH₂CHF₂ | N | |
| H | H | OCH₃ | OCH₂CF₃ | CH | |
| H | H | OCH₃ | OCH₂CH₂F | N | |
| F | H | OCH₃ | OCH₂CF₃ | N | |
| F | H | OCH₃ | OCH₂CH₂F | N | |
| F | H | CH₃ | OCH₂CF₃ | CH | |
| Cl | H | CH₃ | OCH₂CF₃ | CH | |
| Cl | H | CH₃ | OCH₂CHF₂ | CH | |
| Cl | H | CH₃ | OCH₂CH₂F | CH | |
| Cl | H | OCH₃ | OCH₂CF₃ | CH | |
| Cl | H | OCH₃ | OCH₂CH₂F | CH | |
| Cl | H | OCH₃ | OCH₂CF₃ | N | 193–197(d) |
| Cl | H | OCH₃ | OCH₂CHF₂ | N | |
| Cl | H | OCH₃ | OCH₂CH₂F | N | |
| Br | H | CH₃ | OCH₂CH₂F | N | |

TABLE II-continued

General Structure II

| R₃ | R | X | Y | Z | m.p.(°C.) |
|---|---|---|---|---|---|
| Br | H | CH₃ | OCH₂CF₃ | N | |
| Br | H | CH₃ | OCH₂CHF₂ | N | |
| Br | H | OCH₃ | OCH₂CHF₂ | N | |
| Br | H | OCH₃ | OCH₂CF₃ | N | |
| Br | H | OCH₃ | OCH₂CH₂F | N | |
| OCH₃ | H | CH₃ | OCH₂CH₂F | CH | |
| OCH₃ | H | CH₃ | OCH₂CF₃ | CH | |
| OCH₃ | H | OCH₃ | OCH₂CF₃ | CH | |
| OCH₃ | H | OCH₃ | OCH₂CF₃ | N | |
| OCH₃ | H | OCH₃ | OCH₂CH₂F | N | |
| OCH₃ | H | OCH₃ | OCH₂CHF₂ | N | |
| CH₃ | H | CH₃ | OCH₂CH₂F | CH | |
| CH₃ | H | CH₃ | OCH₂CF₃ | CH | |
| CH₃ | H | OCH₃ | OCH₂CF₃ | CH | |
| CH₃ | H | OCH₃ | OCH₂CF₃ | N | |
| CH₃ | H | OCH₃ | OCH₂CHF₂ | N | |
| SO₂N(CH₃)₂ | H | CH₃ | OCH₂CF₃ | CH | |
| SO₂N(CH₃)₂ | H | CH₃ | OCH₂CH₂F | CH | |
| SO₂N(CH₃)₂ | H | CH₃ | OCH₂CF₃ | N | |
| SO₂N(CH₃)₂ | H | OCH₃ | OCH₂CF₃ | N | |
| SO₂N(CH₃)₂ | H | OCH₃ | OCH₂CH₂F | N | |
| SO₂N(CH₃)₂ | H | OCH₃ | OCH₂HF₂ | N | |
| OSO₂CH₃ | H | CH₃ | OCH₂CF₃ | CH | |
| OSO₂CH₃ | H | CH₃ | OCH₂CH₂F | CH | |
| OSO₂CH₃ | H | OCH₃ | OCH₂CH₂F | CH | |
| OSO₂CH₃ | H | OCH₃ | OCH₂CH₂F | N | |
| OSO₂CH₃ | H | OCH₃ | OCH₂CF₃ | N | |
| OSO₂CH₃ | H | OCH₃ | OCH₂CHF₂ | N | |
| SCH₃ | H | OCH₃ | OCH₂CF₃ | N | 115–118(d) |
| SCH₃ | H | OCH₃ | OCH₂CH₂F | N | |
| SCH₃ | H | CH₃ | OCH₂CH₂F | CH | |
| SOCH₃ | H | CH₃ | OCH₂CH₂F | CH | |
| SOCH₃ | H | OCH₃ | OCH₂CH₂F | N | |
| SOCH₃ | H | OCH₃ | OCH₂CF₃ | N | |
| SO₂CH₃ | H | OCH₃ | OCH₂CF₃ | N | |
| SO₂CH₃ | H | OCH₃ | OCH₂CH₂F | N | |
| SO₂CH₃ | H | CH₃ | OCH₂CH₂F | CH | |
| Cl | CH₃ | OCH₃ | OCH₂CF₃ | N | |
| Cl | CH₃ | OCH₃ | OCH₂CH₂F | N | |
| Cl | CH₃ | OCH₃ | OCH₂CHF₂ | N | |
| Cl | CH₃ | CH₃ | OCH₂CF₃ | CH | |
| OCH₃ | H | CH₃ | OCH₂CH₂F | N | |
| OCH₃ | H | CH₃ | OCH₂CHF₂ | N | |
| OCH₃ | H | CH₃ | OCH₂CF₃ | N | |
| CH₃ | H | CH₃ | OCH₂CH₂F | N | |
| CH₃ | H | CH₃ | OCH₂CHF₂ | N | |
| CH₃ | H | CH₃ | OCH₂CF₃ | N | |
| Cl | H | CH₃ | OCH₂CH₂F | N | |
| Cl | H | CH₃ | OCH₂CHF₂ | N | |
| Cl | H | CH₃ | OCH₂CF₃ | N | |
| SCH₃ | H | OCH₃ | OCH₂CHF₂ | N | |
| SCH₃ | H | CH₃ | OCH₂CHF₂ | N | |
| SCH₃ | H | CH₃ | OCH₂CF₃ | N | |
| SCH₃ | H | CH₃ | OCH₂CH₂F | N | |

TABLE III

General Structure III

| R₄ | R | X | Y | Z | m.p.(°C.) |
|---|---|---|---|---|---|
| CH₃ | H | CH₃ | OCH₂CF₃ | CH | |
| CH₃ | H | OCH₃ | OCH₂CF₃ | N | |
| CH₃ | H | OCH₃ | OCH₂CH₂F | N | |
| CH₃ | H | CH₃ | OCH₂CF₃ | N | |
| C₂H₅ | H | CH₃ | OCH₂CF₃ | CH | |
| C₂H₅ | H | CH₃ | OCH₂CH₂F | CH | |
| C₂H₅ | H | OCH₃ | OCH₂CH₂F | N | |
| C₂H₅ | H | OCH₃ | OCH₂CHF₂ | N | |
| C₂H₅ | H | OCH₃ | OCH₂CF₃ | N | |
| n-C₃H₇ | H | OCH₃ | OCH₂CF₃ | N | |
| n-C₃H₇ | H | OCH₃ | OCH₂CH₂F | N | |
| n-C₃H₇ | H | OCH₃ | OCH₂CHF₂ | N | |
| n-C₃H₇ | H | CH₃ | OCH₂CF₃ | CH | |
| F | H | CH₃ | OCH₂CF₃ | CH | |
| F | H | CH₃ | OCH₂CF₃ | N | |
| F | H | OCH₃ | OCH₂CF₃ | N | |
| Cl | H | OCH₃ | OCH₂CH₂F | N | |

TABLE III-continued

General Structure III

| R₄ | R | X | Y | Z | m.p.(°C.) |
|---|---|---|---|---|---|
| Cl | H | OCH₃ | OCH₂CHF₂ | N | |
| Cl | H | OCH₃ | OCH₂CF₃ | N | |
| Cl | H | CH₃ | OCH₂CF₃ | CH | |
| Cl | H | CH₃ | OCH₂CF₃ | N | |
| Br | H | CH₃ | OCH₂CF₃ | N | |
| Br | H | OCH₃ | OCH₃CF₃ | N | |
| Br | H | OCH₃ | OCH₂CH₂F | N | |
| Br | H | OCH₃ | OCH₂CHF₂ | N | |
| NO₂ | H | CH₃ | OCH₂CF₃ | CH | |
| NO₂ | H | OCH₃ | OCH₂CF₃ | N | |
| NO₂ | H | OCH₃ | OCH₂CHF₂ | N | |
| NO₂ | H | OCH₃ | OCH₂CH₂F | N | |
| SO₂N(CH₃)₂ | H | OCH₃ | OCH₂CH₂F | N | |
| SO₂N(CH₃)₂ | H | OCH₃ | OCH₂CF₂ | N | |
| SO₂N(CH₃)₂ | H | OCH₃ | OCH₂CF₃ | N | |
| SO₂N(CH₃)₂ | H | CH₃ | OCH₂CF₃ | CH | |
| SO₂N(C₂H₅)₂ | H | CH₃ | OCH₂CF₃ | CH | |
| SO₂N(C₂H₅)₂ | H | OCH₃ | OCH₂CF₃ | N | |
| SO₂N(C₂H₅)₂ | H | OCH₃ | OCH₂CHF₂ | N | |
| SO₂N(C₂H₅)₂ | H | OCH₃ | OCH₂CH₂F | N | |
| SO₂N(CH₃)n-C₃H₇ | H | OCH₃ | OCH₂CH₂F | N | |
| SO₂N(CH₃)n-C₃H₇ | H | OCH₃ | OCH₂CF₃ | N | |
| SO₂N(CH₃)n-C₃H₇ | H | CH₃ | OCH₂CF₃ | CH | |
| SO₂N(CH₃)OCH₃ | H | OCH₃ | OCH₂CF₃ | N | |
| SO₂N(CH₃)OCH₃ | H | OCH₃ | OCH₂CH₂F | N | |
| SO₂N(CH₃)OCH₃ | H | CH₃ | OCH₂CF₃ | CH | |
| SCH₃ | H | CH₃ | OCH₂CF₃ | CH | |
| SCH₃ | H | OCH₃ | OCH₂CF₃ | N | |
| SCH₃ | H | OCH₃ | OCH₂CH₂F | N | |
| SOCH₃ | H | OCH₃ | OCH₂CH₂F | N | |
| SOCH₃ | H | OCH₃ | OCH₂CF₃ | N | |
| SO₂CH₃ | H | OCH₃ | OCH₂CF₃ | N | |
| SO₂CH₃ | H | OCH₃ | OCH₂CH₂F | N | |
| SO₂CH₃ | H | CH₃ | OCH₂CH₂F | CH | |
| SC₂H₅ | H | CH₃ | OCH₂CF₃ | CH | |
| SC₂H₅ | H | OCH₃ | OCH₂CF₃ | N | |
| SC₂H₅ | H | OCH₃ | OCH₂CH₂F | N | |
| SO₂C₂H₅ | H | OCH₃ | OCH₂CH₂F | N | |
| SO₂C₂H₅ | H | OCH₃ | OCH₂CF₃ | N | |
| SO₂C₂H₅ | H | CH₃ | OCH₂CF₃ | CH | |
| SO₂CH(CH₃)₂ | H | CH₃ | OCH₂CF₃ | CH | |
| SO₂CH(CH₃)₂ | H | OCH₃ | OCH₂CF₃ | N | |
| SO₂CH(CH₃)₂ | H | OCH₃ | OCH₂CH₂F | N | |
| SO₂CH₂CH₂CH₃ | H | OCH₃ | OCH₂CH₂F | N | |
| SO₂CH₂CH₂CH₃ | H | OCH₃ | OCH₂CF₃ | N | |
| SO₂CH₂CH₂CH₃ | H | OCH₃ | OCH₂CF₃ | CH | |
| SCH₂CH=CH₃ | H | CH₃ | OCH₂CF₃ | CH | |
| SCH₂CH=CH₃ | H | OCH₃ | OCH₂CF₃ | N | |
| SCH₂CH=CH₃ | H | OCH₃ | OCH₂CHF₂ | N | |
| SCH₂CH=CH₃ | H | OCH₃ | OCH₂CH₂F | N | |
| SO₂CH₂CH=CH₂ | H | OCH₃ | OCH₂CH₂F | N | |
| SO₂CH₂CH=CH₂ | H | OCH₃ | OCH₂CHF₂ | N | |
| SO₂CH₂CH=CH₂ | H | OCH₃ | OCH₂CF₃ | N | |
| SO₂CH₂CH=CH₂ | H | CH₃ | OCH₂CF₃ | CH | |
| CH₃ | H | OCH₃ | OCH₂CF₃ | N | |
| CH₃ | H | CH₃ | OCH₂CH₂F | N | |
| CH₃ | H | CH₃ | OCH₂CHF₂ | N | |
| SCH₃ | H | CH₃ | OCH₂CHF₂ | N | |
| SCH₃ | H | CH₃ | OCH₂CH₂F | N | |
| SCH₃ | H | CH₃ | OCH₂CHF₂ | N | |
| SCH₃ | H | CH₃ | OCH₂CF₃ | N | |
| SOCH₃ | H | OCH₃ | OCH₂CHF₂ | N | |
| SOCH₃ | H | CH₃ | OCH₂CH₂F | N | |
| SOCH₃ | H | CH₃ | OCH₂CHF₂ | N | |
| SOCH₃ | H | CH₃ | OCH₂CF₃ | N | |
| SO₂CH₃ | H | OCH₃ | OCH₂CHF₂ | N | |
| SO₂CH₃ | H | CH₃ | OCH₂CH₂F | N | |
| SO₂CH₃ | H | CH₃ | OCH₂CHF₂ | N | |
| SO₂CH₃ | H | CH₃ | OCH₂CF₃ | N | |
| SCH₂CH₃ | H | OCH₃ | OCH₂CHF₂ | N | |
| SCH₂CH₃ | H | CH₃ | OCH₂CH₂F | N | |
| SCH₂CH₃ | H | CH₃ | OCH₂CHF₂ | N | |
| SCH₂CH₃ | H | CH₃ | OCH₂CF₃ | N | |
| SOCH₂CH₃ | H | OCH₃ | OCH₂CH₂F | N | |
| SOCH₂CH₃ | H | OCH₃ | OCH₂CF₃ | N | |
| SOCH₂CH₃ | H | CH₃ | OCH₂CH₂F | N | |
| SOCH₂CH₃ | H | CH₃ | OCH₂CHF₂ | N | |
| SOCH₂CH₃ | H | CH₃ | OCH₂CF₃ | N | |

TABLE III-continued

General Structure III

| R4 | R | X | Y | Z | m.p.(°C.) |
|---|---|---|---|---|---|
| SO2CH2CH3 | H | OCH3 | OCH2CHF2 | N | |
| SO2CH2CH3 | H | CH3 | OCH2CH2F | N | |
| SO2CH2CH3 | H | CH3 | OCH2CHF2 | N | |
| SO2CH2CH3 | H | CH3 | OCH2CF3 | N | |
| SO2N(CH3)2 | H | CH3 | OCH2CHF2 | N | |
| SO2N(CH3)2 | H | CH3 | OCH2CHF2 | N | |

TABLE IV

General Structure IV

| R4 | R | X | Y | Z | m.p.(°C.) |
|---|---|---|---|---|---|
| CH3 | H | CH3 | OCH2CF3 | CH | |
| CH3 | H | OCH3 | OCH2CF3 | N | |
| CH3 | H | OCH3 | OCH2CH2F | N | |
| CH3 | H | CH3 | OCH2CF3 | N | |
| C2H5 | H | CH3 | OCH2CF3 | CH | |
| C2H5 | H | CH3 | OCH2CH2F | CH | |
| C2H5 | H | OCH3 | OCH2CH2F | N | |
| C2H5 | H | OCH3 | OCH2CHF2 | N | |
| C2H5 | H | OCH3 | OCH2CF3 | N | |
| n-C3H7 | H | OCH3 | OCH2CF3 | N | |
| n-C3H7 | H | OCH3 | OCH2CH2F | N | |
| n-C3H7 | H | OCH3 | OCH2CHF2 | N | |
| n-C3H7 | H | CH3 | OCH2CF3 | CH | |
| F | H | CH3 | OCH2CF3 | CH | |
| F | H | OCH3 | OCH2CF3 | N | |
| F | H | OCH3 | OCH2CH2F | N | |
| Cl | H | OCH3 | OCH2CH2F | N | |
| Cl | H | OCH3 | OCH2CHF2 | N | |
| Cl | H | OCH3 | OCH2CF3 | N | |
| Cl | H | CH3 | OCH2CF3 | CH | |
| Cl | H | CH3 | OCH2CF3 | CH | |
| Br | H | CH3 | OCH2CF3 | N | |
| Br | H | OCH3 | OCH2CF3 | N | |
| Br | H | OCH3 | OCH2CH2F | N | |
| Br | H | OCH3 | OCH2CHF2 | N | |
| NO2 | H | CH3 | OCH2CF3 | CH | |
| NO2 | H | OCH3 | OCH2CF3 | N | |
| NO2 | H | OCH3 | OCH2CHF2 | N | |
| NO2 | H | OCH3 | OCH2CH2F | N | |
| SO2N(CH3)2 | H | OCH3 | OCH2CH2F | N | |
| SO2N(CH3)2 | H | OCH3 | OCH2CHF2 | N | |
| SO2N(CH3)2 | H | OCH3 | OCH2CF3 | N | |
| SO2N(CH3)2 | H | CH3 | OCH2CF3 | CH | |
| SO2N(C2H5)2 | H | CH3 | OCH2CF3 | CH | |
| SO2N(C2H5)2 | H | OCH3 | OCH2CF3 | N | |
| SO2N(C2H5)2 | H | OCH3 | OCH2CHF2 | N | |
| SO2N(C2H5)2 | H | OCH3 | OCH2CH2F | N | |
| SO2N(CH3)n-C3H7 | H | OCH3 | OCH2CH2F | N | |
| SO2N(CH3)n-C3H7 | H | OCH3 | OCH2CF3 | N | |
| SO2N(CH3)n-C3H7 | H | CH3 | OCH2CF3 | CH | |
| SO2N(CH3)OCH3 | H | OCH3 | OCH2CF3 | N | |
| SO2N(CH3)OCH3 | H | OCH3 | OCH2CH2F | N | |
| SO2N(CH3)OCH3 | H | CH3 | OCH2CF3 | CH | |
| SCH3 | H | CH3 | OCH2CF3 | CH | |
| SCH3 | H | OCH3 | OCH2CF3 | N | |
| SCH3 | H | OCH3 | OCH2CH2F | N | |
| SOCH3 | H | OCH3 | OCH2CH2F | N | |
| SOCH3 | H | OCH3 | OCH2CF3 | N | |
| SO2CH3 | H | OCH3 | OCH2CH2F | N | |
| SO2CH3 | H | OCH3 | OCH2CH2F | N | |
| SO2CH3 | H | CH3 | OCH2CH2F | CH | |
| SC2H5 | H | CH3 | OCH2CF3 | CH | |
| SC2H5 | H | OCH3 | OCH2CF3 | N | |
| SC2H5 | H | OCH3 | OCH2CH2F | N | |
| SO2C2H5 | H | OCH3 | OCH2CH2F | N | |
| SO2C2H5 | H | OCH3 | OCH2CH2F | N | |
| SO2C2H5 | H | CH3 | OCH2CF3 | CH | |
| SO2CH(CH3)2 | H | CH3 | OCH2CF3 | CH | |
| SO2CH(CH3)2 | H | OCH3 | OCH2CF3 | N | |
| SO2CH(CH3)2 | H | OCH3 | OCH2CH2F | N | |
| SO2CH2CH2CH3 | H | OCH3 | OCH2CH2F | N | |
| SO2CH2CH2CH3 | H | OCH3 | OCH2CF3 | N | |
| SO2CH2CH2CH3 | H | CH3 | OCH2CF3 | CH | |
| SCH2CH=CH3 | H | CH3 | OCH2CF3 | CH | |
| SCH2CH=CH3 | H | OCH3 | OCH2CF3 | N | |
| SCH2CH=CH3 | H | OCH3 | OCH2CHF2 | N | |
| SCH2CH=CH3 | H | OCH3 | OCH2CH2F | N | |

TABLE IV-continued

General Structure IV

| R4 | R | X | Y | Z | m.p.(°C.) |
|---|---|---|---|---|---|
| SO2CH2CH=CH2 | H | OCH3 | OCH2CH2F | N | |
| SO2CH2CH=CH2 | H | OCH3 | OCH2CHF2 | N | |
| SO2CH2CH=CH2 | H | OCH3 | OCH2CF3 | N | |
| SO2CH2CH=CH2 | H | CH3 | OCH2CF3 | CH | |
| CH3 | H | OCH3 | OCH2CHF2 | N | |
| CH3 | H | CH3 | OCH2CH2F | N | |
| CH3 | H | CH3 | OCH2CHF2 | N | |
| SCH3 | H | OCH3 | OCH2CHF2 | N | |
| SCH3 | H | CH3 | OCH2CH2F | N | |
| SCH3 | H | CH3 | OCH2CHF2 | N | |
| SCH3 | H | CH3 | OCH2CF3 | N | |
| SOCH3 | H | OCH3 | OCH2CHF2 | N | |
| SOCH3 | H | CH3 | OCH2CH2F | N | |
| SOCH3 | H | CH3 | OCH2CHF2 | N | |
| SOCH3 | H | CH3 | OCH2CF3 | N | |
| SO2CH3 | H | OCH3 | OCH2CHF2 | N | |
| SO2CH3 | H | CH3 | OCH2CH2F | N | |
| SO2CH3 | H | CH3 | OCH2CHF2 | N | |
| SO2CH3 | H | CH3 | OCH2CF3 | N | |
| SCH2CH3 | H | OCH3 | OCH2CHF2 | N | |
| SCH2CH3 | H | CH3 | OCH2CH2F | N | |
| SCH2CH3 | H | CH3 | OCH2CHF2 | N | |
| SCH2CH3 | H | CH3 | OCH2CF3 | N | |
| SOCH2CH3 | H | OCH3 | OCH2CH2F | N | |
| SOCH2CH3 | H | CH3 | OCH2CHF2 | N | |
| SOCH2CH3 | H | CH3 | OCH2CF3 | N | |
| SOCH2CH3 | H | OCH3 | OCH2CH2F | N | |
| SOCH2CH3 | H | OCH3 | OCH2CHF2 | N | |
| SOCH2CH3 | H | OCH3 | OCH2CF3 | N | |
| SO2CH2CH3 | H | OCH3 | OCH2CHF2 | N | |
| SO2CH2CH3 | H | CH3 | OCH2CH2F | N | |
| SO2CH2CH3 | H | CH3 | OCH2CHF2 | N | |
| SO2CH2CH3 | H | CH3 | OCH2CF3 | N | |
| SO2N(CH3)2 | H | CH3 | OCH2CH2F | N | |
| SO2N(CH3)2 | H | CH3 | OCH2CHF2 | N | |
| SO2N(CH3)2 | H | CH3 | OCH2CF3 | N | |

TABLE V

General Structure V

| R4 | R | X | Y | Z | m.p. (°C.) |
|---|---|---|---|---|---|
| CH3 | H | CH3 | OCH2CF3 | CH | |
| CH3 | H | OCH3 | OCH2CF3 | N | |
| CH3 | H | OCH3 | OCH2CH2F | N | |
| CH3 | H | CH3 | OCH2CF3 | N | |
| C2H5 | H | CH3 | OCH2CF3 | CH | |
| C2H5 | H | CH3 | OCH2CH2F | CH | |
| C2H5 | H | OCH3 | OCH2CH2F | N | |
| C2H5 | H | OCH3 | OCH2CHF2 | N | |
| C2H5 | H | OCH3 | OCH2CF3 | N | |
| n-C3H7 | H | OCH3 | OCH2CF3 | N | |
| n-C3H7 | H | OCH3 | OCH2CH2F | N | |
| n-C3H7 | H | OCH3 | OCH2CHF2 | N | |
| n-C3H7 | H | CH3 | OCH2CF3 | CH | |
| F | H | CH3 | OCH2CF3 | CH | |
| F | H | OCH3 | OCH2CF3 | N | |
| F | H | OCH3 | OCH2CH2F | N | |
| Cl | H | OCH3 | OCH2CH2F | N | |
| Cl | H | OCH3 | OCH2CHF2 | N | |
| Cl | H | OCH3 | OCH2CF3 | N | |
| Cl | H | CH3 | OCH2CF3 | CH | |
| Cl | H | CH3 | OCH2CF3 | N | |
| Br | H | CH3 | OCH2CF3 | N | |
| Br | H | OCH3 | OCH2CF3 | N | |
| Br | H | OCH3 | OCH2CH2F | N | |
| Br | H | OCH3 | OCH2CHF2 | N | |
| NO2 | H | CH3 | OCH2CF3 | CH | |
| NO2 | H | OCH3 | OCH2CF3 | N | |
| NO2 | H | OCH3 | OCH2CHF2 | N | |
| NO2 | H | OCH3 | OCH2CH2F | N | |
| SO2N(CH3)2 | H | OCH3 | OCH2CH2F | N | |
| SO2N(CH3)2 | H | OCH3 | OCH2CHF2 | N | |
| SO2N(CH3)2 | H | OCH3 | OCH2CF3 | N | |
| SO2N(CH3)2 | H | CH3 | OCH2CF3 | CH | |
| SO2N(C2H5)2 | H | CH3 | OCH2CF3 | CH | |
| SO2N(C2H5)2 | H | OCH3 | OCH2CF3 | N | |
| SO2N(C2H5)2 | H | OCH3 | OCH2CHF2 | N | |

TABLE V-continued

General Structure V

| R4 | R | X | Y | Z | m.p. (°C.) |
|---|---|---|---|---|---|
| SO2N(C2H5)2 | H | OCH3 | OCH2CH2F | N | |
| SO2N(CH3)n-C3H7 | H | OCH3 | OCH2CH2F | N | |
| SO2N(CH3)n-C3H7 | H | OCH3 | OCH2CF3 | N | |
| SO2N(CH3)n-C3H7 | H | CH3 | OCH2CF3 | CH | |
| SO2N(CH3)OCH3 | H | OCH3 | OCH2CF3 | N | |
| SO2N(CH3)OCH3 | H | OCH3 | OCH2CH2F | N | |
| SO2N(CH3)OCH3 | H | CH3 | OCH2CF3 | CH | |
| SCH3 | H | CH3 | OCH2CF3 | CH | |
| SCH3 | H | OCH3 | OCH2CF3 | N | |
| SCH3 | H | OCH3 | OCH2CH2F | N | |
| SOCH3 | H | OCH3 | OCH2CH2F | N | |
| SOCH3 | H | OCH3 | OCH2CF3 | N | |
| SO2CH3 | H | OCH3 | OCH2CF3 | N | |
| SO2CH3 | H | OCH3 | OCH2CH2F | N | |
| SO2CH3 | H | CH3 | OCH2CH2F | CH | |
| SC2H5 | H | CH3 | OCH2CF3 | CH | |
| SC2H5 | H | OCH3 | OCH2CF3 | N | |
| SC2H5 | H | OCH3 | OCH2CH2F | N | |
| SO2C2H5 | H | OCH3 | OCH2CH2F | N | |
| SO2C2H5 | H | OCH3 | OCH2CF3 | N | |
| SO2C2H5 | H | CH3 | OCH2CF3 | CH | |
| SO2CH(CH3)2 | H | CH3 | OCH2CF3 | CH | |
| SO2CH(CH3)2 | H | OCH3 | OCH2CF3 | N | |
| SO2CH(CH3)2 | H | OCH3 | OCH2CH2F | N | |
| SO2CH2CH2CH3 | H | OCH3 | OCH2CH2F | N | |
| SO2CH2CH2CH3 | H | OCH3 | OCH2CF3 | N | |
| SO2CH2CH2CH3 | H | CH3 | OCH2CF3 | CH | |
| SCH2CH=CH3 | H | CH3 | OCH2CF3 | CH | |
| SCH2CH=CH3 | H | OCH3 | OCH2CF3 | N | |
| SCH2CH=CH3 | H | OCH3 | OCH2CHF2 | N | |
| SCH2CH=CH3 | H | OCH3 | OCH2CH2F | N | |
| SO2CH2CH=CH2 | H | OCH3 | OCH2CH2F | N | |
| SO2CH2CH=CH2 | H | OCH3 | OCH2CHF2 | N | |
| SO2CH2CH=CH2 | H | OCH3 | OCH2CF3 | N | |
| SO2CH2CH=CH2 | H | CH3 | OCH2CF3 | CH | |
| CH3 | H | OCH3 | OCH2CF3 | N | |
| CH3 | H | CH3 | OCH2CH2F | N | |
| CH3 | H | CH3 | OCH2CHF2 | N | |
| SCH3 | H | OCH3 | OCH2CHF2 | N | |
| SCH3 | H | CH3 | OCH2CH2F | N | |
| SCH3 | H | CH3 | OCH2CHF2 | N | |
| SCH3 | H | CH3 | OCH2CF3 | N | |
| SOCH3 | H | OCH3 | OCH2CHF2 | N | |
| SOCH3 | H | CH3 | OCH2CH2F | N | |
| SOCH3 | H | CH3 | OCH2CHF2 | N | |
| SOCH3 | H | CH3 | OCH2CF3 | N | |
| SO2CH3 | H | OCH3 | OCH2CHF2 | N | |
| SO2CH3 | H | CH3 | OCH2CH2F | N | |
| SO2CH3 | H | CH3 | OCH2CHF2 | N | |
| SO2CH3 | H | CH3 | OCH2CF3 | N | |
| SCH2CH3 | H | OCH3 | OCH2CHF2 | N | |
| SCH2CH3 | H | CH3 | OCH2CH2F | N | |
| SCH2CH3 | H | CH3 | OCH2CHF2 | N | |
| SCH2CH3 | H | CH3 | OCH2CF3 | N | |
| SOCH2CH3 | H | CH3 | OCH2CH2F | N | |
| SOCH2CH3 | H | CH3 | OCH2CHF2 | N | |
| SOCH2CH3 | H | CH3 | OCH2CF3 | N | |
| SOCH2CH3 | H | OCH3 | OCH2CH2F | N | |
| SOCH2CH3 | H | OCH3 | OCH2CHF2 | N | |
| SOCH2CH3 | H | OCH3 | OCH2CF3 | N | |
| SO2CH2CH3 | H | OCH3 | OCH2CHF2 | N | |
| SO2CH2CH3 | H | CH3 | OCH2CH2F | N | |
| SO2CH2CH3 | H | CH3 | OCH2CHF2 | N | |
| SO2CH2CH3 | H | CH3 | OCH2CF3 | N | |
| SO2N(CH3)2 | H | CH3 | OCH2CH2F | N | |
| SO2N(CH3)2 | H | CH3 | OCH2CHF2 | N | |
| SO2N(CH3)2 | H | CH3 | OCH2CF3 | N | |

TABLE VI

General Structure VI

| R2 | R5 | R6 | R | X | Y | Z | m.p. (°C.) |
|---|---|---|---|---|---|---|---|
| H | CH3 | H | H | CH3 | OCH2CHF2 | CH | |
| H | CH3 | H | H | CH3 | OCH2CH2F | CH | |
| H | CH3 | H | H | CH3 | OCH2CHF2 | N | |
| H | CH3 | H | H | CH3 | OCH2CH2F | N | |
| H | CH3 | H | H | OCH3 | OCH2CH2F | N | |
| H | CH3 | H | H | OCH3 | OCH2CHF2 | N | |
| H | C2H5 | H | H | CH3 | OCH2CH2F | CH | |
| H | C2H5 | H | H | OCH3 | OCH2CH2F | N | |
| H | C2H5 | H | H | OCH3 | OCH2CHF2 | N | |
| H | CH(CH3)2 | H | H | OCH3 | OCH2CH2F | N | |
| H | CH(CH3)2 | H | H | OCH3 | OCH2CH2F | N | |
| H | CH(CH3)2 | H | H | CH3 | OCH2CH2F | CH | |
| H | CH2CH2CH3 | H | H | CH3 | OCH2CH2F | CH | |
| H | CH2CH2CH3 | H | H | OCH3 | OCH2CH2F | N | |
| H | CH2CH2CH3 | H | H | OCH3 | OCH2CHF2 | N | |
| H | (CH2)3CH3 | H | H | OCH3 | OCH2CHF2 | N | |
| H | (CH2)3CH3 | H | H | OCH3 | OCH2CH2F | N | |
| H | (CH2)3CH3 | H | H | CH3 | OCH2CH2F | CH | |
| H | CH2CH(CH3)2 | H | H | CH3 | OCH2CH2F | CH | |
| H | CH2CH(CH3)2 | H | H | OCH3 | OCH2CH2F | N | |
| H | CH2CH(CH3)2 | H | H | OCH3 | OCH2CHF2 | N | |
| H | CH(CH3)C2H5 | H | H | OCH3 | OCH2CH2F | N | |
| H | CH(CH3)C2H5 | H | H | OCH3 | OCH2CHF2 | N | |
| H | CH(CH3)C2H5 | H | H | CH3 | OCH2CH2F | N | |
| H | (CH2)4CH3 | H | H | CH3 | OCH2CH2F | CH | |
| H | (CH2)4CH3 | H | H | OCH3 | OCH2CH2F | N | |
| H | (CH2)4CH3 | H | H | OCH3 | OCH2CHF2 | N | |
| H | CH(CH3)(CH2)2CH3 | H | H | OCH3 | OCH2CH2F | N | |
| H | CH(CH3)(CH2)2CH3 | H | H | OCH3 | OCH2CH2F | N | |
| H | CH(CH3)(CH2)2CH3 | H | H | CH3 | OCH2CH2F | CH | |
| H | CH2CH2OCH3 | H | H | CH3 | OCH2CH2F | CH | |
| H | CH2CH2OCH3 | H | H | OCH3 | OCH2CH2F | N | |
| H | CH2CH2OCH3 | H | H | OCH3 | OCH2CHF2 | N | |
| H | CH2CH2OC2H5 | H | H | OCH3 | OCH2CHF2 | N | |
| H | CH2CH2OC2H5 | H | H | OCH3 | OCH2CH2F | N | |
| H | CH2CH2OC2H5 | H | H | CH3 | OCH2CH2F | CH | |
| H | CHF2 | H | H | CH3 | OCH2CH2F | CH | |
| H | CHF2 | H | H | OCH3 | OCH2CH2F | N | |
| H | CHF2 | H | H | OCH3 | OCH2CHF2 | N | |

TABLE VI-continued

General Structure VI

| R₂ | R₅ | R₆ | R | X | Y | Z | m.p. (°C.) |
|---|---|---|---|---|---|---|---|
| H | CF₃ | H | H | OCH₃ | OCH₂CHF₂ | N | |
| H | CF₃ | H | H | OCH₃ | OCH₂CH₂F | N | |
| H | CH₂CH₂F | H | H | OCH₃ | OCH₂CH₂F | N | |
| H | CH₂CH₂F | H | H | OCH₃ | OCH₂CHF₂ | N | |
| H | CH₂CF₃ | H | H | OCH₃ | OCH₂CHF₂ | N | |
| H | CH₂CF₃ | H | H | OCH₃ | OCH₂CH₂F | N | |
| H | CH₂CCl₃ | H | H | OCH₃ | OCH₂CH₂F | N | |
| H | CH₂CCl₃ | H | H | OCH₃ | OCH₂CHF₂ | N | |
| H | CH₂CH₂Cl | H | H | OCH₃ | OCH₂CHF₂ | N | |
| H | CH₂CH₂Cl | H | H | OCH₃ | OCH₂CH₂F | N | |
| H | CH₂CHCl₂ | H | H | OCH₃ | OCH₂CH₂F | N | |
| H | CH₂CHCl₂ | H | H | OCH₃ | OCH₂CHF₂ | N | |
| H | (CH₂)₃Cl | H | H | OCH₃ | OCH₂CH₂F | N | |
| H | (CH₂)₃Cl | H | H | OCH₃ | OCH₂CHF₂ | N | |
| H | (CH₂)₃Cl | H | H | CH₃ | OCH₂CHF₂ | CH | |
| H | (CH₂)₄Cl | H | H | CH₃ | OCH₂CHF₂ | CH | |
| H | (CH₂)₄Cl | H | H | OCH₃ | OCH₂CHF₂ | N | |
| H | (CH₂)₄Cl | H | H | OCH₃ | OCH₂CH₂F | N | |
| H | CH(CH₃)CH₂Cl | H | H | OCH₃ | OCH₂CH₂F | N | |
| H | CH(CH₃)CH₂Cl | H | H | OCH₃ | OCH₂CHF₂ | N | |
| H | CH₂CH₂Br | H | H | OCH₃ | OCH₂CHF₂ | N | |
| H | CH₂CH₂Br | H | H | OCH₃ | OCH₂CH₂F | N | |
| H | (CH₂)₃Br | H | H | OCH₃ | OCH₂CH₂F | N | |
| H | (CH₂)₃Br | H | H | OCH₃ | OCH₂CHF₂ | N | |
| 6-Cl | CH₃ | H | H | OCH₃ | OCH₂CHF₂ | N | |
| 6-Cl | CH₃ | H | H | OCH₃ | OCH₂CH₂F | N | |
| 5-Cl | CH₃ | H | H | OCH₃ | OCH₂CH₂F | N | |
| 5-OCH₃ | CH₃ | H | H | OCH₃ | OCH₂CH₂F | N | |
| 5-Br | CH₃ | H | H | OCH₃ | OCH₂CH₂F | N | |
| H | CH₃ | CH₃ | H | CH₃ | OCH₂CHF₂ | CH | |
| H | CH₃ | CH₃ | H | CH₃ | OCH₂CH₂F | CH | |
| H | CH₃ | CH₃ | H | CH₃ | OCH₂CHF₂ | N | |
| H | CH₃ | CH₃ | H | OCH₃ | OCH₂CH₂F | N | |
| H | CH₃ | CH₃ | H | OCH₃ | OCH₂CH₂F | N | |
| H | CH₃ | CH₃ | H | OCH₃ | OCH₂CHF₂ | N | |
| H | C₂H₅ | CH₃ | H | CH₃ | OCH₂CH₂F | CH | |
| H | C₂H₅ | CH₃ | H | OCH₃ | OCH₂CH₂F | N | |
| H | C₂H₅ | CH₃ | H | OCH₃ | OCH₂CHF₂ | N | |
| H | CH(CH₃)₂ | CH₃ | H | OCH₃ | OCH₂CHF₂ | N | |
| H | CH(CH₃)₂ | CH₃ | H | OCH₃ | OCH₂CH₂F | N | |
| H | CH(CH₃)₂ | CH₃ | H | CH₃ | OCH₂CH₂F | CH | |
| H | CH₂CH₂CH₃ | CH₃ | H | CH₃ | OCH₂CH₂F | CH | |
| H | CH₂CH₂CH₃ | CH₃ | H | OCH₃ | OCH₂CH₂F | N | |
| H | CH₂CH₂CH₃ | CH₃ | H | OCH₃ | OCH₂CHF₂ | N | |
| H | (CH₂)₃CH₃ | CH₃ | H | OCH₃ | OCH₂CHF₂ | N | |
| H | (CH₂)₃CH₃ | CH₃ | H | OCH₃ | OCH₂CH₂F | N | |
| H | (CH₂)₃CH₃ | CH₃ | H | CH₃ | OCH₂CH₂F | CH | |
| H | CH₂CH(CH₃)₂ | CH₃ | H | CH₃ | OCH₂CH₂F | CH | |
| H | CH₂CH(CH₃)₂ | CH₃ | H | OCH₃ | OCH₂CH₂F | N | |
| H | CH₂CH(CH₃)₂ | CH₃ | H | OCH₃ | OCH₂CHF₂ | N | |
| H | CH(CH₃)C₂H₅ | CH₃ | H | OCH₃ | OCH₂CHF₂ | N | |
| H | CH(CH₃)C₂H₅ | CH₃ | H | OCH₃ | OCH₂CH₂F | N | |
| H | CH(CH₃)C₂H₅ | CH₃ | H | CH₃ | OCH₂CH₂F | N | |
| H | (CH₂)₄CH₃ | CH₃ | H | CH₃ | OCH₂CH₂F | CH | |
| H | (CH₂)₄CH₃ | CH₃ | H | OCH₃ | OCH₂CH₂F | N | |
| H | (CH₂)₄CH₃ | CH₃ | H | OCH₃ | OCH₂CHF₂ | N | |
| H | CH(CH₃)(CH₂)₂CH₃ | CH₃ | H | OCH₃ | OCH₂CHF₂ | N | |
| H | CH(CH₃)(CH₂)₂CH₃ | CH₃ | H | OCH₃ | OCH₂CH₂F | N | |
| H | CH(CH₃)(CH₂)₂CH₃ | CH₃ | H | CH₃ | OCH₂CHF₂ | CH | |
| H | CH₂CH₂OCH₃ | CH₃ | H | CH₃ | OCH₂CH₂F | CH | |
| H | CH₂CH₂OCH₃ | CH₃ | H | OCH₃ | OCH₂CH₂F | N | |
| H | CH₂CH₂OCH₃ | CH₃ | H | OCH₃ | OCH₂CHF₂ | N | |
| H | CH₂CH₂OC₂H₅ | CH₃ | H | OCH₃ | OCH₂CHF₂ | N | |
| H | CH₂CH₂OC₂H₅ | CH₃ | H | OCH₃ | OCH₂CH₂F | N | |
| H | CH₂CH₂OC₂H₅ | CH₃ | H | CH₃ | OCH₂CH₂F | CH | |
| H | CHF₂ | CH₃ | H | CH₃ | OCH₂CH₂F | CH | |
| H | CHF₂ | CH₃ | H | OCH₃ | OCH₂CH₂F | N | |
| H | CHF₂ | CH₃ | H | OCH₃ | OCH₂CHF₂ | N | |
| H | CF₃ | CH₃ | H | OCH₃ | OCH₂CF₂H₂ | N | |
| H | CF₃ | CH₃ | H | OCH₃ | OCH₂CHF₂ | N | |
| H | CH₂CH₂F | CH₃ | H | OCH₃ | OCH₂CH₂F | N | |
| H | CH₂CH₂F | CH₃ | H | OCH₃ | OCH₂CHF₂ | N | |
| H | CH₂CF₃ | CH₃ | H | OCH₃ | OCH₂CHF₂ | N | |
| H | CH₂CF₃ | CH₃ | H | OCH₃ | OCH₂CH₂F | N | |
| H | CH₂CCl₃ | CH₃ | H | OCH₃ | OCH₂CH₂F | N | |
| H | CH₂CCl₃ | CH₃ | H | OCH₃ | OCH₂CHF₂ | N | |
| H | CH₂CH₂Cl | CH₃ | H | OCH₃ | OCH₂CHF₂ | N | |
| H | CH₂CH₂Cl | CH₃ | H | OCH₃ | OCH₂CH₂F | N | |
| H | CH₂CHCl₂ | CH₃ | H | OCH₃ | OCH₂CH₂F | N | |
| H | CH₂CHCl₂ | CH₃ | H | OCH₃ | OCH₂CHF₂ | N | |

TABLE VI-continued

General Structure VI

| R$_2$ | R$_5$ | R$_6$ | R | X | Y | Z | m.p. (°C.) |
|---|---|---|---|---|---|---|---|
| H | (CH$_2$)$_3$Cl | CH$_3$ | H | OCH$_3$ | OCH$_2$CH$_2$F | N | |
| H | (CH$_2$)$_3$Cl | CH$_3$ | H | OCH$_3$ | OCH$_2$CHF$_2$ | N | |
| H | (CH$_2$)$_3$Cl | CH$_3$ | H | CH$_3$ | OCH$_2$CHF$_2$ | CH | |
| H | (CH$_2$)$_4$Cl | CH$_3$ | H | CH$_3$ | OCH$_2$CHF$_2$ | CH | |
| H | (CH$_2$)$_4$Cl | CH$_3$ | H | OCH$_3$ | OCH$_2$CHF$_2$ | N | |
| H | (CH$_2$)$_4$Cl | CH$_3$ | H | OCH$_3$ | OCH$_2$CH$_2$F | N | |
| H | CH(CH$_3$)CH$_2$Cl | CH$_3$ | H | OCH$_3$ | OCH$_2$CH$_2$F | N | |
| H | CH(CH$_3$)CH$_2$Cl | CH$_3$ | H | OCH$_3$ | OCH$_2$CHF$_2$ | N | |
| H | CH$_2$CH$_2$Br | CH$_3$ | H | OCH$_3$ | OCH$_2$CHF$_2$ | N | |
| H | CH$_2$CH$_2$Br | CH$_3$ | H | OCH$_3$ | OCH$_2$CH$_2$F | N | |
| H | (CH$_2$)$_3$Br | CH$_3$ | H | OCH$_3$ | OCH$_2$CH$_2$F | N | |
| H | (CH$_2$)$_3$Br | CH$_3$ | H | OCH$_3$ | OCH$_2$CHF$_2$ | N | |
| 6-Cl | CH$_3$ | CH$_3$ | H | OCH$_3$ | OCH$_2$CHF$_2$ | N | |
| 6-Cl | CH$_3$ | CH$_3$ | H | OCH$_3$ | OCH$_2$CH$_2$F | N | |
| 5-Cl | CH$_3$ | CH$_3$ | H | OCH$_3$ | OCH$_2$CH$_2$F | N | |
| 5-OCH$_3$ | CH$_3$ | CH$_3$ | H | OCH$_3$ | OCH$_2$CH$_2$F | N | |
| 5-Br | CH$_3$ | CH$_3$ | H | OCH$_3$ | OCH$_2$CH$_2$F | N | |
| 5-Cl | CH$_2$CH$_3$ | H | H | OCH$_3$ | OCH$_2$CH$_2$F | N | |
| 5-Cl | CH$_2$CH$_2$CH$_3$ | H | H | OCH$_3$ | OCH$_2$CH$_2$F | N | |
| 5-Cl | CH(CH$_3$)$_2$ | H | H | OCH$_3$ | OCH$_2$CH$_2$F | N | |
| 5-Cl | CH$_2$CH$_2$CH$_2$CH$_3$ | H | H | OCH$_3$ | OCH$_2$CH$_2$F | N | |
| 5-Cl | CH$_2$CH(CH$_3$)$_2$ | H | H | OCH$_3$ | OCH$_2$CH$_2$F | N | |
| 5-Cl | CH(CH$_3$)C$_2$H$_5$ | H | H | OCH$_3$ | OCH$_2$CH$_2$F | N | |
| 5-Cl | (CH$_2$)$_4$CH$_3$ | H | H | OCH$_3$ | OCH$_2$CH$_2$F | N | |
| 5-Cl | CH$_2$CH$_2$OCH$_3$ | H | H | OCH$_3$ | OCH$_2$CH$_2$F | N | |
| 5-Cl | CH$_2$CH$_2$OC$_2$H$_5$ | H | H | OCH$_3$ | OCH$_2$CH$_2$F | N | |
| 5-Cl | CH$_2$CH$_2$CH$_2$Cl | H | H | OCH$_3$ | OCH$_2$CH$_2$F | N | |
| H | H | H | H | CH$_3$ | OCH$_2$CH$_2$F | N | |
| H | H | H | H | CH$_3$ | OCH$_2$CHF$_2$ | N | |
| H | H | H | H | OCH$_3$ | OCH$_2$CH$_2$F | N | |
| H | H | H | H | OCH$_3$ | OCH$_2$CHF$_2$ | N | |
| H | CH$_2$CH$_3$ | H | H | CH$_3$ | OCH$_2$CH$_2$F | N | |
| H | CH$_2$CH$_3$ | H | H | CH$_3$ | OCH$_2$CHF$_2$ | N | |
| H | CH(CH$_3$)$_2$ | H | H | CH$_3$ | OCH$_2$CH$_2$F | N | |
| H | CH(CH$_3$)$_2$ | H | H | CH$_3$ | OCH$_2$CHF$_2$ | N | |
| H | CH$_2$CH$_2$CH$_3$ | H | H | CH$_3$ | OCH$_2$CH$_2$F | N | |
| H | CH$_2$CH$_2$CH$_3$ | H | H | CH$_3$ | OCH$_2$CHF$_2$ | N | |
| H | (CH$_2$)$_3$CH$_3$ | H | H | CH$_3$ | OCH$_2$CH$_2$F | N | |
| H | (CH$_2$)$_3$CH$_3$ | H | H | CH$_3$ | OCH$_2$CHF$_2$ | N | |
| H | CH$_2$CH(CH$_3$)$_2$ | H | H | CH$_3$ | OCH$_2$CH$_2$F | N | |
| H | CH$_2$CH(CH$_3$)$_2$ | H | H | CH$_3$ | OCH$_2$CHF$_2$ | N | |
| H | CH(CH$_3$)C$_2$H$_5$ | H | H | CH$_3$ | OCH$_2$CHF$_2$ | N | |
| H | CH$_2$CH$_2$OCH$_3$ | H | H | CH$_3$ | OCH$_2$CH$_2$F | N | |
| H | CH$_2$CH$_2$OCH$_3$ | H | H | CH$_3$ | OCH$_2$CHF$_2$ | N | |
| H | CH$_2$CH$_2$OC$_2$H$_5$ | H | H | CH$_3$ | OCH$_2$CH$_2$F | N | |
| H | CH$_2$CH$_2$OC$_2$H$_5$ | H | H | CH$_3$ | OCH$_2$CHF$_2$ | N | |
| H | CHF$_2$ | H | H | CH$_3$ | OCH$_2$CH$_2$F | N | |
| H | CHF$_2$ | H | H | CH$_3$ | OCH$_2$CHF$_2$ | N | |
| H | CF$_3$ | H | H | CH$_3$ | OCH$_2$CH$_2$F | N | |
| H | CF$_3$ | H | H | CH$_3$ | OCH$_2$CHF$_2$ | N | |
| H | CH$_2$CH$_2$F | H | H | CH$_3$ | OCH$_2$CH$_2$F | N | |
| H | CH$_2$CH$_2$F | H | H | CH$_3$ | OCH$_2$CHF$_2$ | N | |
| H | CH$_2$CF$_3$ | H | H | CH$_3$ | OCH$_2$CH$_2$F | N | |
| H | CH$_2$CF$_3$ | H | H | CH$_3$ | OCH$_2$CHF$_2$ | N | |
| H | CH$_2$CH$_2$Cl | H | H | CH$_3$ | OCH$_2$CH$_2$F | N | |
| H | CH$_2$CH$_2$Cl | H | H | CH$_3$ | OCH$_2$CHF$_2$ | N | |
| H | CH$_2$CHCl$_2$ | H | H | CH$_3$ | OCH$_2$CH$_2$F | N | |
| H | CH$_2$CHCl$_2$ | H | H | CH$_3$ | OCH$_2$CHF$_2$ | N | |
| H | CH$_2$CCl$_3$ | H | H | CH$_3$ | OCH$_2$CH$_2$F | N | |
| H | CH$_2$CCl$_3$ | H | H | CH$_3$ | OCH$_2$CHF$_2$ | N | |
| H | (CH$_2$)$_3$Cl | H | H | CH$_3$ | OCH$_2$CH$_2$F | N | |
| H | (CH$_2$)$_3$Cl | H | H | CH$_3$ | OCH$_2$CHF$_2$ | N | |
| H | CH(CH$_3$)CH$_2$Cl | H | H | CH$_3$ | OCH$_2$CH$_2$F | N | |
| H | CH(CH$_3$)CH$_2$Cl | H | H | CH$_3$ | OCH$_2$CHF$_2$ | N | |
| H | (CH$_2$)$_4$Cl | H | H | CH$_3$ | OCH$_2$CH$_2$F | N | |
| H | (CH$_2$)$_4$Cl | H | H | CH$_3$ | OCH$_2$CHF$_2$ | N | |
| H | (CH$_2$)$_4$F | H | H | CH$_3$ | OCH$_2$CH$_2$F | N | |
| H | (CH$_2$)$_4$F | H | H | CH$_3$ | OCH$_2$CHF$_2$ | N | |
| H | (CH$_2$)$_4$F | H | H | OCH$_3$ | OCH$_2$CH$_2$F | N | |
| H | (CH$_2$)$_4$F | H | H | OCH$_3$ | OCH$_2$CHF$_2$ | N | |
| H | CH$_2$CH$_2$Br | H | H | CH$_3$ | OCH$_2$CH$_2$F | N | |
| H | CH$_2$CH$_2$Br | H | H | CH$_3$ | OCH$_2$CHF$_2$ | N | |
| H | (CH$_2$)$_3$Br | H | H | CH$_3$ | OCH$_2$CH$_2$F | N | |
| H | (CH$_2$)$_3$Br | H | H | CH$_3$ | OCH$_2$CHF$_2$ | N | |
| H | (CH$_2$)$_4$Br | H | H | CH$_3$ | OCH$_2$CH$_2$F | N | |
| H | (CH$_2$)$_4$Br | H | H | CH$_3$ | OCH$_2$CHF$_2$ | N | |
| H | (CH$_2$)$_4$Br | H | H | OCH$_3$ | OCH$_2$CH$_2$F | N | |
| H | (CH$_2$)$_4$Br | H | H | OCH$_3$ | OCH$_2$CHF$_2$ | N | |
| H | (CH$_2$)$_3$F | H | H | CH$_3$ | OCH$_2$CH$_2$F | N | |
| H | (CH$_2$)$_3$F | H | H | CH$_3$ | OCH$_2$CHF$_2$ | N | |

TABLE VI-continued

General Structure VI

| R$_2$ | R$_5$ | R$_6$ | R | X | Y | Z | m.p. (°C.) |
|---|---|---|---|---|---|---|---|
| H | (CH$_2$)$_3$F | H | H | OCH$_3$ | OCH$_2$CH$_2$F | N | |
| H | (CH$_2$)$_3$F | H | H | OCH$_3$ | OCH$_2$CHF$_2$ | N | |
| H | CH$_2$CHF$_2$ | H | H | CH$_3$ | OCH$_2$CH$_2$F | N | |
| H | CH$_2$CHF$_2$ | H | H | CH$_3$ | OCH$_2$CHF$_2$ | N | |
| H | CH$_2$CHF$_2$ | H | H | OCH$_3$ | OCH$_2$CH$_2$F | N | |
| H | CH$_2$CHF$_2$ | H | H | OCH$_3$ | OCH$_2$CHF$_2$ | N | |
| H | CH$_2$F | H | H | CH$_3$ | OCH$_2$CH$_2$F | N | |
| H | CH$_2$F | H | H | CH$_3$ | OCH$_2$CHF$_2$ | N | |
| H | CH$_2$F | H | H | OCH$_3$ | OCH$_2$CH$_2$F | N | |
| H | CH$_2$F | H | H | OCH$_3$ | OCH$_2$CHF$_2$ | N | |
| H | CH$_2$(CH$_3$)CH$_2$Br | H | H | CH$_3$ | OCH$_2$CH$_2$F | N | |
| H | CH$_2$(CH$_3$)CH$_2$Br | H | H | CH$_3$ | OCH$_2$CHF$_2$ | N | |
| H | CH$_2$(CH$_3$)CH$_2$Br | H | H | OCH$_3$ | OCH$_2$CH$_2$F | N | |
| H | CH$_2$(CH$_3$)CH$_2$Br | H | H | OCH$_3$ | OCH$_2$CHF$_2$ | N | |
| H | CH$_2$(CH$_3$)CH$_2$F | H | H | CH$_3$ | OCH$_2$CH$_2$F | N | |
| H | CH$_2$(CH$_3$)CH$_2$F | H | H | CH$_3$ | OCH$_2$CHF$_2$ | N | |
| H | CH$_2$(CH$_3$)CH$_2$F | H | H | OCH$_3$ | OCH$_2$CH$_2$F | N | |
| H | CH$_2$(CH$_3$)CH$_2$F | H | H | OCH$_3$ | OCH$_2$CHF$_2$ | N | |
| H | CH$_2$CHClCH$_3$ | H | H | CH$_3$ | OCH$_2$CH$_2$F | N | |
| H | CH$_2$CHClCH$_3$ | H | H | CH$_3$ | OCH$_2$CHF$_2$ | N | |
| H | CH$_2$CHClCH$_3$ | H | H | OCH$_3$ | OCH$_2$CH$_2$F | N | |
| H | CH$_2$CHClCH$_3$ | H | H | OCH$_3$ | OCH$_2$CHF$_2$ | N | |
| H | CH$_2$CHBrCH$_3$ | H | H | CH$_3$ | OCH$_2$CH$_2$F | N | |
| H | CH$_2$CHBrCH$_3$ | H | H | CH$_3$ | OCH$_2$CHF$_2$ | N | |
| H | CH$_2$CHBrCH$_3$ | H | H | OCH$_3$ | OCH$_2$CH$_2$F | N | |
| H | CH$_2$CHBrCH$_3$ | H | H | OCH$_3$ | OCH$_2$CHF$_2$ | N | |
| H | CH$_2$CHFCH$_3$ | H | H | CH$_3$ | OCH$_2$CH$_2$F | N | |
| H | CH$_2$CHFCH$_3$ | H | H | CH$_3$ | OCH$_2$CHF$_2$ | N | |
| H | CH$_2$CHFCH$_3$ | H | H | OCH$_3$ | OCH$_2$CH$_2$F | N | |
| H | CH$_2$CHFCH$_3$ | H | H | OCH$_3$ | OCH$_2$CHF$_2$ | N | |
| H | CH(CH$_2$Cl)$_2$ | H | H | CH$_3$ | OCH$_2$CH$_2$F | N | |
| H | CH(CH$_2$Cl)$_2$ | H | H | CH$_3$ | OCH$_2$CHF$_2$ | N | |
| H | CH(CH$_2$Cl)$_2$ | H | H | OCH$_3$ | OCH$_2$CH$_2$F | N | |
| H | CH(CH$_2$Cl)$_2$ | H | H | OCH$_3$ | OCH$_2$CHF$_2$ | N | |
| H | CH(CH$_2$F)$_2$ | H | H | CH$_3$ | OCH$_2$CH$_2$F | N | |
| H | CH(CH$_2$F)$_2$ | H | H | CH$_3$ | OCH$_2$CHF$_2$ | N | |
| H | CH(CH$_2$F)$_2$ | H | H | OCH$_3$ | OCH$_2$CH$_2$F | N | |
| H | CH(CH$_2$F)$_2$ | H | H | OCH$_3$ | OCH$_2$CHF$_2$ | N | |
| H | CH(CH$_3$)CCl$_3$ | H | H | CH$_3$ | OCH$_2$CXH$_2$F | N | |
| H | CH(CH$_3$)CCl$_3$ | H | H | CH$_3$ | OCH$_2$CHF$_2$ | N | |
| H | CH(CH$_3$)CCl$_3$ | H | H | OCH$_3$ | OCH$_2$CH$_2$F | N | |
| H | CH(CH$_3$)CCl$_3$ | H | H | OCH$_3$ | OCH$_2$CHF$_2$ | N | |
| H | CH$_2$CH$_2$CHClCH$_3$ | H | H | CH$_3$ | OCH$_2$CH$_2$F | N | |
| H | CH$_2$CH$_2$CHClCH$_3$ | H | H | CH$_3$ | OCH$_2$CHF$_2$ | N | |
| H | CH$_2$CH$_2$CHClCH$_3$ | H | H | OCH$_3$ | OCH$_2$CH$_2$F | N | |
| H | CH$_2$CH$_2$CHClCH$_3$ | H | H | OCH$_3$ | OCH$_2$CHF$_2$ | N | |
| H | CH$_2$CH$_2$CHBrCH$_3$ | H | H | CH$_3$ | OCH$_2$CH$_2$F | N | |
| H | CH$_2$CH$_2$CHBrCH$_3$ | H | H | CH$_3$ | OCH$_2$CHF$_2$ | N | |
| H | CH$_2$CH$_2$CHBrCH$_3$ | H | H | OCH$_3$ | OCH$_2$CH$_2$F | N | |
| H | CH$_2$CH$_2$CHBrCH$_3$ | H | H | OCH$_3$ | OCH$_2$CHF$_2$ | N | |
| H | CH$_2$CH$_2$CHFCH$_3$ | H | H | CH$_3$ | OCH$_2$CH$_2$F | N | |
| H | CH$_2$CH$_2$CHFCH$_3$ | H | H | CH$_3$ | OCH$_2$CHF$_2$ | N | |
| H | CH$_2$CH$_2$CHFCH$_3$ | H | H | OCH$_3$ | OCH$_2$CH$_2$F | N | |
| H | CH$_2$CH$_2$CHFCH$_3$ | H | H | OCH$_3$ | OCH$_2$CHF$_2$ | N | |
| H | CH$_2$CHClCH$_2$CH$_3$ | H | H | CH$_3$ | OCH$_2$CH$_2$F | N | |
| H | CH$_2$CHClCH$_2$CH$_3$ | H | H | CH$_3$ | OCH$_2$CHF$_2$ | N | |
| H | CH$_2$CHClCH$_2$CH$_3$ | H | H | OCH$_3$ | OCH$_2$CH$_2$F | N | |
| H | CH$_2$CHClCH$_2$CH$_3$ | H | H | OCH$_3$ | OCH$_2$CHF$_2$ | N | |
| H | CH$_2$CHBrCH$_2$CH$_3$ | H | H | CH$_3$ | OCH$_2$CH$_2$F | N | |
| H | CH$_2$CHBrCH$_2$CH$_3$ | H | H | CH$_3$ | OCH$_2$CHF$_2$ | N | |
| H | CH$_2$CHBrCH$_2$CH$_3$ | H | H | OCH$_3$ | OCH$_2$CH$_2$F | N | |
| H | CH$_2$CHBrCH$_2$CH$_3$ | H | H | OCH$_3$ | OCH$_2$CHF$_2$ | N | |
| H | CH$_2$CHFCH$_2$CH$_3$ | H | H | CH$_3$ | OCH$_2$CH$_2$F | N | |
| H | CH$_2$CHFCH$_2$CH$_3$ | H | H | CH$_3$ | OCH$_2$CHF$_2$ | N | |
| H | CH$_2$CHFCH$_2$CH$_3$ | H | H | OCH$_3$ | OCH$_2$CH$_2$F | N | |
| H | CH$_2$CHFCH$_2$CH$_3$ | H | H | OCH$_3$ | OCH$_2$CHF$_2$ | N | |
| H | CH(CH$_3$)CHClCH$_3$ | H | H | CH$_3$ | OCH$_2$CH$_2$F | N | |
| H | CH(CH$_3$)CHClCH$_3$ | H | H | CH$_3$ | OCH$_2$CHF$_2$ | N | |
| H | CH(CH$_3$)CHClCH$_3$ | H | H | OCH$_3$ | OCH$_2$CH$_2$F | N | |
| H | CH(CH$_3$)CHClCH$_3$ | H | H | OCH$_3$ | OCH$_2$CHF$_2$ | N | |
| H | CH(CH$_3$)CHBrCH$_3$ | H | H | CH$_3$ | OCH$_2$CH$_2$F | N | |
| H | CH(CH$_3$)CHBrCH$_3$ | H | H | CH$_3$ | OCH$_2$CHF$_2$ | N | |
| H | CH(CH$_3$)CHBrCH$_3$ | H | H | OCH$_3$ | OCH$_2$CH$_2$F | N | |
| H | CH(CH$_3$)CHBrCH$_3$ | H | H | OCH$_3$ | OCH$_2$CHF$_2$ | N | |
| H | CH(CH$_3$)CHFCH$_3$ | H | H | CH$_3$ | OCH$_2$CH$_2$F | N | |
| H | CH(CH$_3$)CHFCH$_3$ | H | H | CH$_3$ | OCH$_2$CHF$_2$ | N | |
| H | CH(CH$_3$)CHFCH$_3$ | H | H | OCH$_3$ | OCH$_2$CH$_2$F | N | |
| H | CH(CH$_3$)CHFCH$_3$ | H | H | OCH$_3$ | OCH$_2$CHF$_2$ | N | |
| H | CH$_2$CCl$_2$CH$_3$ | H | H | CH$_3$ | OCH$_2$CH$_2$F | N | |
| H | CH$_2$CCl$_2$CH$_3$ | H | H | CH$_3$ | OCH$_2$CHF$_2$ | N | |

TABLE VI-continued

General Structure VI

| R2 | R5 | R6 | R | X | Y | Z | m.p. (°C.) |
|---|---|---|---|---|---|---|---|
| H | CH2CCl2CH3 | H | H | OCH3 | OCH2CH2F | N | |
| H | CH2CCl2CH3 | H | H | OCH3 | OCH2CHF2 | N | |
| H | CH2CH(CH3)CH2Cl | H | H | CH3 | OCH2CH2F | N | |
| H | CH2CH(CH3)CH2Cl | H | H | CH3 | OCH2CHF2 | N | |
| H | CH2CH(CH3)CH2Cl | H | H | OCH3 | OCH2CH2F | N | |
| H | CH2CH(CH3)CH2Cl | H | H | OCH3 | OCH2CHF2 | N | |
| H | CH2CH(CH3)CH2Br | H | H | CH3 | OCH2CH2F | N | |
| H | CH2CH(CH3)CH2Br | H | H | CH3 | OCH2CHF2 | N | |
| H | CH2CH(CH3)CH2Br | H | H | OCH3 | OCH2CH2F | N | |
| H | CH2CH(CH3)CH2Br | H | H | OCH3 | OCH2CHF2 | N | |
| H | CH2CH(CH3)CH2F | H | H | CH3 | OCH2CH2F | N | |
| H | CH2CH(CH3)CH2F | H | H | CH3 | OCH2CHF2 | N | |
| H | CH2CH(CH3)CH2F | H | H | OCH3 | OCH2CH2F | N | |
| H | CH2CH(CH3)CH2F | H | H | OCH3 | OCH2CHF2 | N | |
| H | CH2CF2Cl | H | H | CH3 | OCH2CH2F | N | |
| H | CH2CF2Cl | H | H | CH3 | OCH2CHF2 | N | |
| H | CH2CF2Cl | H | H | OCH3 | OCH2CH2F | N | |
| H | CH2CF2Cl | H | H | OCH3 | OCH2CHF2 | N | |
| H | CH(CHCl2)CH2Cl | H | H | CH3 | OCH2CH2F | N | |
| H | CH(CHCl2)CH2Cl | H | H | CH3 | OCH2CHF2 | N | |
| H | CH(CHCl2)CH2Cl | H | H | OCH3 | OCH2CH2F | N | |
| H | CH(CHCl2)CH2Cl | H | H | OCH3 | OCH2CHF2 | N | |
| H | CH(CHCl2)CH2F | H | H | CH3 | OCH2CH2F | N | |
| H | CH(CHCl2)CH2F | H | H | CH3 | OCH2CHF2 | N | |
| H | CH(CHCl2)CH2F | H | H | OCH3 | OCH2CH2F | N | |
| H | CH(CHCl2)CH2F | H | H | OCH3 | OCH2CHF2 | N | |
| H | CH(CH2Cl)CH2CH2Cl | H | H | CH3 | OCH2CH2F | N | |
| H | CH(CH2Cl)CH2CH2Cl | H | H | CH3 | OCH2CHF2 | N | |
| H | CH(CH2Cl)CH2CH2Cl | H | H | OCH3 | OCH2CH2F | N | |
| H | CH(CH2Cl)CH2CH2Cl | H | H | OCH3 | OCH2CHF2 | N | |
| H | CH2Br | H | H | CH3 | OCH2CH2F | N | |
| H | CH2Br | H | H | CH3 | OCH2CHF2 | N | |
| H | CH2Br | H | H | OCH3 | OCH2CH2F | N | |
| H | CH2Br | H | H | OCH3 | OCH2CHF2 | N | |
| H | CH2Cl | H | H | CH3 | OCH2CH2F | N | |
| H | CH2Cl | H | H | CH3 | OCH2CHF2 | N | |
| H | CH2Cl | H | H | OCH3 | OCH2CH2F | N | |
| H | CH2Cl | H | H | OCH3 | OCH2CHF2 | N | |
| H | CHCl2 | H | H | CH3 | OCH2CH2F | N | |
| H | CHCl2 | H | H | CH3 | OCH2CHF2 | N | |
| H | CHCl2 | H | H | OCH3 | OCH2CH2F | N | |
| H | CHCl2 | H | H | OCH3 | OCH2CHF2 | N | |
| H | CCl3 | H | H | CH3 | OCH2CH2F | N | |
| H | CCl3 | H | H | CH3 | OCH2CHF2 | N | |
| H | CCl3 | H | H | OCH3 | OCH2CH2F | N | |
| H | CCl3 | H | H | OCH3 | OCH2CHF2 | N | |

TABLE VIa

General Structure VIa

| R2 | R5 | R6 | R | X | Y | Z | m.p. (°C.) |
|---|---|---|---|---|---|---|---|
| H | CH3 | H | H | CH3 | OCH2CHF2 | CH | |
| H | CH3 | H | H | CH3 | OCH2CH2F | CH | |
| H | CH3 | H | H | CH3 | OCH2CHF2 | N | |
| H | CH3 | H | H | CH3 | OCH2CH2F | N | |
| H | CH3 | H | H | OCH3 | OCH2CH2F | N | |
| H | CH3 | H | H | OCH3 | OCH2CHF2 | N | |
| H | C2H5 | H | H | CH3 | OCH2CH2F | CH | |
| H | C2H5 | H | H | OCH3 | OCH2CH2F | N | |
| H | C2H5 | H | H | OCH3 | OCH2CHF2 | N | |
| H | CH(CH3)2 | H | H | OCH3 | OCH2CHF2 | N | |
| H | CH(CH3)2 | H | H | OCH3 | OCH2CH2F | N | |
| H | CH(CH3)2 | H | H | CH3 | OCH2CH2F | CH | |
| H | CH2CH2CH3 | H | H | CH3 | OCH2CH2F | CH | |
| H | CH2CH2CH3 | H | H | OCH3 | OCH2CH2F | N | |
| H | CH2CH2CH3 | H | H | OCH3 | OCH2CHF2 | N | |
| H | (CH2)3CH3 | H | H | OCH3 | OCH2CHF2 | N | |
| H | (CH2)3CH3 | H | H | OCH3 | OCH2CH2F | N | |
| H | (CH2)3CH3 | H | H | CH3 | OCH2CH2F | CH | |
| H | CH2CH(CH3)2 | H | H | CH3 | OCH2CH2F | CH | |
| H | CH2CH(CH3)2 | H | H | OCH3 | OCH2CH2F | N | |
| H | CH2CH(CH3)2 | H | H | OCH3 | OCH2CHF2 | N | |
| H | CH(CH3)C2H5 | H | H | OCH3 | OCH2CH2F | N | |
| H | CH(CH3)C2H5 | H | H | OCH3 | OCH2CHF2 | N | |
| H | CH(CH3)C2H5 | H | H | CH3 | OCH2CH2F | N | |
| H | (CH2)4CH3 | H | H | CH3 | OCH2CH2F | CH | |
| H | (CH2)4CH3 | H | H | OCH3 | OCH2CH2F | N | |

TABLE VIa-continued

General Structure VIa

| R$_2$ | R$_5$ | R$_6$ | R | X | Y | Z | m.p. (°C.) |
|---|---|---|---|---|---|---|---|
| H | (CH$_2$)$_4$CH$_3$ | H | H | OCH$_3$ | OCH$_2$CHF$_2$ | N | |
| H | CH(CH$_3$)(CH$_2$)$_2$CH$_3$ | H | H | OCH$_3$ | OCH$_2$CHF$_2$ | N | |
| H | CH(CH$_3$)(CH$_2$)$_2$CH$_3$ | H | H | OCH$_3$ | OCH$_2$CH$_2$F | N | |
| H | CH(CH$_3$)(CH$_2$)$_2$CH$_3$ | H | H | CH$_3$ | OCH$_2$CHF$_2$ | CH | |
| H | CH$_2$CH$_2$OCH$_3$ | H | H | CH$_3$ | OCH$_2$CH$_2$F | CH | |
| H | CH$_2$CH$_2$OCH$_3$ | H | H | OCH$_3$ | OCH$_2$CH$_2$F | N | |
| H | CH$_2$CH$_2$OCH$_3$ | H | H | OCH$_3$ | OCH$_2$CHF$_2$ | N | |
| H | CH$_2$CH$_2$OC$_2$H$_5$ | H | H | OCH$_3$ | OCH$_2$CHF$_2$ | N | |
| H | CH$_2$CH$_2$OC$_2$H$_5$ | H | H | OCH$_3$ | OCH$_2$CH$_2$F | N | |
| H | CH$_2$CH$_2$OC$_2$H$_5$ | H | H | CH$_3$ | OCH$_2$CH$_2$F | CH | |
| H | CHF$_2$ | H | H | CH$_3$ | OCH$_2$CH$_2$F | CH | |
| H | CHF$_2$ | H | H | OCH$_3$ | OCH$_2$CH$_2$F | N | |
| H | CHF$_2$ | H | H | OCH$_3$ | OCH$_2$CHF$_2$ | N | |
| H | CF$_3$ | H | H | OCH$_3$ | OCH$_2$CHF$_2$ | N | |
| H | CF$_3$ | H | H | OCH$_3$ | OCH$_2$CH$_2$F | N | |
| H | CH$_2$CH$_2$F | H | H | OCH$_3$ | OCH$_2$CH$_2$F | N | |
| H | CH$_2$CH$_2$F | H | H | OCH$_3$ | OCH$_2$CHF$_2$ | N | |
| H | CH$_2$CF$_3$ | H | H | OCH$_3$ | OCH$_2$CHF$_2$ | N | |
| H | CH$_2$CF$_3$ | H | H | OCH$_3$ | OCH$_2$CH$_2$F | N | |
| H | CH$_2$CCl$_3$ | H | H | OCH$_3$ | OCH$_2$CH$_2$F | N | |
| H | CH$_2$CCl$_3$ | H | H | OCH$_3$ | OCH$_2$CHF$_2$ | N | |
| H | CH$_2$CH$_2$Cl | H | H | OCH$_3$ | OCH$_2$CHF$_2$ | N | |
| H | CH$_2$CH$_2$Cl | H | H | OCH$_3$ | OCH$_2$CH$_2$F | N | |
| H | CH$_2$CHCl$_2$ | H | H | OCH$_3$ | OCH$_2$CH$_2$F | N | |
| H | CH$_2$CHCl$_2$ | H | H | OCH$_3$ | OCH$_2$CHF$_2$ | N | |
| H | (CH$_2$)$_3$Cl | H | H | OCH$_3$ | OCH$_2$CH$_2$F | N | |
| H | (CH$_2$)$_3$Cl | H | H | OCH$_3$ | OCH$_2$CHF$_2$ | N | |
| H | (CH$_2$)$_3$Cl | H | H | CH$_3$ | OCH$_2$CHF$_2$ | CH | |
| H | (CH$_2$)$_4$Cl | H | H | CH$_3$ | OCH$_2$CHF$_2$ | CH | |
| H | (CH$_2$)$_4$Cl | H | H | OCH$_3$ | OCH$_2$CHF$_2$ | N | |
| H | (CH$_2$)$_4$Cl | H | H | OCH$_3$ | OCH$_2$CH$_2$F | N | |
| H | CH(CH$_3$)CH$_2$Cl | H | H | OCH$_3$ | OCH$_2$CH$_2$F | N | |
| H | CH(CH$_3$)CH$_2$Cl | H | H | OCH$_3$ | OCH$_2$CHF$_2$ | N | |
| H | CH$_2$CH$_2$Br | H | H | OCH$_3$ | OCH$_2$CHF$_2$ | N | |
| H | CH$_2$CH$_2$Br | H | H | OCH$_3$ | OCH$_2$CH$_2$F | N | |
| H | (CH$_2$)$_3$Br | H | H | OCH$_3$ | OCH$_2$CH$_2$F | N | |
| H | (CH$_2$)$_3$Br | H | H | OCH$_3$ | OCH$_2$CHF$_2$ | N | |
| 5-Cl | CH$_3$ | H | H | OCH$_3$ | OCH$_2$CHF$_2$ | N | |
| 5-Cl | CH$_3$ | H | H | OCH$_3$ | OCH$_2$CH$_2$F | N | |
| 6-Cl | CH$_3$ | H | H | OCH$_3$ | OCH$_2$CH$_2$F | N | |
| 6-OCH$_3$ | CH$_3$ | H | H | OCH$_3$ | OCH$_2$CH$_2$F | N | |
| 6-Br | CH$_3$ | H | H | OCH$_3$ | OCH$_2$CH$_2$F | N | |
| H | H | H | H | CH$_3$ | OCH$_2$CH$_2$F | N | |
| H | H | H | H | CH$_3$ | OCH$_2$CHF$_2$ | N | |
| H | H | H | H | OCH$_3$ | OCH$_2$CH$_2$F | N | |
| H | H | H | H | OCH$_3$ | OCH$_2$CHF$_2$ | N | |
| H | CH$_2$CH$_3$ | H | H | CH$_3$ | OCH$_2$CH$_2$F | N | |
| H | CH$_2$CH$_3$ | H | H | CH$_3$ | OCH$_2$CHF$_2$ | N | |
| H | CH(CH$_3$)$_2$ | H | H | CH$_3$ | OCH$_2$CH$_2$F | N | |
| H | CH(CH$_3$)$_2$ | H | H | CH$_3$ | OCH$_2$CHF$_2$ | N | |
| H | CH$_2$CH$_2$CH$_3$ | H | H | CH$_3$ | OCH$_2$CH$_2$F | N | |
| H | CH$_2$CH$_2$CH$_3$ | H | H | CH$_3$ | OCH$_2$CHF$_2$ | N | |
| H | (CH$_2$)$_3$CH$_3$ | H | H | CH$_3$ | OCH$_2$CH$_2$F | N | |
| H | (CH$_2$)$_3$CH$_3$ | H | H | CH$_3$ | OCH$_2$CHF$_2$ | N | |
| H | CH$_2$CH(CH$_3$)$_2$ | H | H | CH$_3$ | OCH$_2$CH$_2$F | N | |
| H | CH$_2$CH(CH$_3$)$_2$ | H | H | CH$_3$ | OCH$_2$CHF$_2$ | N | |
| H | CH(CH$_3$)C$_2$H$_5$ | H | H | CH$_3$ | OCH$_2$CHF$_2$ | N | |
| H | CH$_2$CH$_2$OCH$_3$ | H | H | CH$_3$ | OCH$_2$CH$_2$F | N | |
| H | CH$_2$CH$_2$OCH$_3$ | H | H | CH$_3$ | OCH$_2$CHF$_2$ | N | |
| H | CH$_2$CH$_2$OC$_2$H$_5$ | H | H | CH$_3$ | OCH$_2$CH$_2$F | N | |
| H | CH$_2$CH$_2$OC$_2$H$_5$ | H | H | CH$_3$ | OCH$_2$CHF$_2$ | N | |
| H | CHF$_2$ | H | H | CH$_3$ | OCH$_2$CH$_2$F | N | |
| H | CHF$_2$ | H | H | CH$_3$ | OCH$_2$CHF$_2$ | N | |
| H | CF$_3$ | H | H | CH$_3$ | OCH$_2$CH$_2$F | N | |
| H | CF$_3$ | H | H | CH$_3$ | OCH$_2$CHF$_2$ | N | |
| H | CH$_2$CH$_2$F | H | H | CH$_3$ | OCH$_2$CH$_2$F | N | |
| H | CH$_2$CH$_2$F | H | H | CH$_3$ | OCH$_2$CHF$_2$ | N | |
| H | CH$_2$CF$_3$ | H | H | CH$_3$ | OCH$_2$CH$_2$F | N | |
| H | CH$_2$CF$_3$ | H | H | CH$_3$ | OCH$_2$CHF$_2$ | N | |
| H | CH$_2$CH$_2$Cl | H | H | CH$_3$ | OCH$_2$CH$_2$F | N | |
| H | CH$_2$CH$_2$Cl | H | H | CH$_3$ | OCH$_2$CHF$_2$ | N | |
| H | CH$_2$CHCl$_2$ | H | H | CH$_3$ | OCH$_2$CH$_2$F | N | |
| H | CH$_2$CHCl$_2$ | H | H | CH$_3$ | OCH$_2$CHF$_2$ | N | |
| H | CH$_2$CCl$_3$ | H | H | CH$_3$ | OCH$_2$CH$_2$F | N | |
| H | CH$_2$CCl$_3$ | H | H | CH$_3$ | OCH$_2$CHF$_2$ | N | |
| H | (CH$_2$)$_3$Cl | H | H | CH$_3$ | OCH$_2$CH$_2$F | N | |
| H | (CH$_2$)$_3$Cl | H | H | CH$_3$ | OCH$_2$CHF$_2$ | N | |
| H | CH(CH$_3$)CH$_2$Cl | H | H | CH$_3$ | OCH$_2$CH$_2$F | N | |
| H | CH(CH$_3$)CH$_2$Cl | H | H | CH$_3$ | OCH$_2$CHF$_2$ | N | |

TABLE VIa-continued

General Structure VIa

| R$_2$ | R$_5$ | R$_6$ | R | X | Y | Z | m.p. (°C.) |
|---|---|---|---|---|---|---|---|
| H | (CH$_2$)$_4$Cl | H | H | CH$_3$ | OCH$_2$CH$_2$F | N | |
| H | (CH$_2$)$_4$Cl | H | H | CH$_3$ | OCH$_2$CHF$_2$ | N | |
| H | (CH$_2$)$_4$F | H | H | CH$_3$ | OCH$_2$CH$_2$F | N | |
| H | (CH$_2$)$_4$F | H | H | CH$_3$ | OCH$_2$CHF$_2$ | N | |
| H | (CH$_2$)$_4$F | H | H | OCH$_3$ | OCH$_2$CH$_2$F | N | |
| H | (CH$_2$)$_4$F | H | H | OCH$_3$ | OCH$_2$CHF$_2$ | N | |
| H | CH$_2$CH$_2$Br | H | H | CH$_3$ | OCH$_2$CH$_2$F | N | |
| H | CH$_2$CH$_2$Br | H | H | CH$_3$ | OCH$_2$CHF$_2$ | N | |
| H | (CH$_2$)$_3$Br | H | H | CH$_3$ | OCH$_2$CH$_2$F | N | |
| H | (CH$_2$)$_3$Br | H | H | CH$_3$ | OCH$_2$CHF$_2$ | N | |
| H | (CH$_2$)$_4$Br | H | H | CH$_3$ | OCH$_2$CH$_2$F | N | |
| H | (CH$_2$)$_2$Br | H | H | CH$_3$ | OCH$_2$CHF$_2$ | N | |
| H | (CH$_2$)$_4$Br | H | H | OCH$_3$ | OCH$_2$CH$_2$F | N | |
| H | (CH$_2$)$_4$Br | H | H | OCH$_3$ | OCH$_2$CHF$_2$ | N | |
| H | (CH$_2$)$_3$F | H | H | CH$_3$ | OCH$_2$CH$_2$F | N | |
| H | (CH$_2$)$_3$F | H | H | CH$_3$ | OCH$_2$CHF$_2$ | N | |
| H | (CH$_2$)$_3$F | H | H | OCH$_3$ | OCH$_2$CH$_2$F | N | |
| H | (CH$_2$)$_3$F | H | H | OCH$_3$ | OCH$_2$CHF$_2$ | N | |
| H | CH$_2$CHF$_2$ | H | H | CH$_3$ | OCH$_2$CH$_2$F | N | |
| H | CH$_2$CHF$_2$ | H | H | CH$_3$ | OCH$_2$CHF$_2$ | N | |
| H | CH$_2$CHF$_2$ | H | H | OCH$_3$ | OCH$_2$CH$_2$F | N | |
| H | CH$_2$CHF$_2$ | H | H | OCH$_3$ | OCH$_2$CHF$_2$ | N | |
| H | CH$_2$F | H | H | CH$_3$ | OCH$_2$CH$_2$F | N | |
| H | CH$_2$F | H | H | CH$_3$ | OCH$_2$CHF$_2$ | N | |
| H | CH$_2$F | H | H | OCH$_3$ | OCH$_2$CH$_2$F | N | |
| H | CH$_2$F | H | H | OCH$_3$ | OCH$_2$CHF$_2$ | N | |
| H | CH$_2$(CH$_3$)CH$_2$Br | H | H | CH$_3$ | OCH$_2$CH$_2$F | N | |
| H | CH$_2$(CH$_3$)CH$_2$Br | H | H | CH$_3$ | OCH$_2$CHF$_2$ | N | |
| H | CH$_2$(CH$_3$)CH$_2$Br | H | H | OCH$_3$ | OCH$_2$CH$_2$F | N | |
| H | CH$_2$(CH$_3$)CH$_2$Br | H | H | OCH$_3$ | OCH$_2$CHF$_2$ | N | |
| H | CH$_2$(CH$_3$)CH$_2$F | H | H | CH$_3$ | OCH$_2$CH$_2$F | N | |
| H | CH$_2$(CH$_3$)CH$_2$F | H | H | CH$_3$ | OCH$_2$CHF$_2$ | N | |
| H | CH$_2$(CH$_3$)CH$_2$F | H | H | OCH$_3$ | OCH$_2$CH$_2$F | N | |
| H | CH$_2$(CH$_3$)CH$_2$F | H | H | OCH$_3$ | OCH$_2$CHF$_2$ | N | |
| H | CH$_2$CHClCH$_3$ | H | H | CH$_3$ | OCH$_2$CH$_2$F | N | |
| H | CH$_2$CHClCH$_3$ | H | H | CH$_3$ | OCH$_2$CHF$_2$ | N | |
| H | CH$_2$CHClCH$_3$ | H | H | OCH$_3$ | OCH$_2$CH$_2$F | N | |
| H | CH$_2$CHClCH$_3$ | H | H | OCH$_3$ | OCH$_2$CHF$_2$ | N | |
| H | CH$_2$CHBrCH$_3$ | H | H | CH$_3$ | OCH$_2$CH$_2$F | N | |
| H | CH$_2$CHBrCH$_3$ | H | H | CH$_3$ | OCH$_2$CHF$_2$ | N | |
| H | CH$_2$CHBrCH$_3$ | H | H | OCH$_3$ | OCH$_2$CH$_2$F | N | |
| H | CH$_2$CHBrCH$_3$ | H | H | OCH$_3$ | OCH$_2$CHF$_2$ | N | |
| H | CH$_2$CHFCH$_3$ | H | H | CH$_3$ | OCH$_2$CH$_2$F | N | |
| H | CH$_2$CHFCH$_3$ | H | H | CH$_3$ | OCH$_2$CHF$_2$ | N | |
| H | CH$_2$CHFCH$_3$ | H | H | OCH$_3$ | OCH$_2$CH$_2$F | N | |
| H | CH$_2$CHFCH$_3$ | H | H | OCH$_3$ | OCH$_2$CHF$_2$ | N | |
| H | CH(CH$_2$Cl)$_2$ | H | H | CH$_3$ | OCH$_2$CH$_2$F | N | |
| H | CH(CH$_2$Cl)$_2$ | H | H | CH$_3$ | OCH$_2$CHF$_2$ | N | |
| H | CH(CH$_2$Cl)$_2$ | H | H | OCH$_3$ | OCH$_2$CH$_2$F | N | |
| H | CH(CH$_2$Cl)$_2$ | H | H | OCH$_3$ | OCH$_2$CHF$_2$ | N | |
| H | CH(CH$_2$F)$_2$ | H | H | CH$_3$ | OCH$_2$CH$_2$F | N | |
| H | CH(CH$_2$F)$_2$ | H | H | CH$_3$ | OCH$_2$CHF$_2$ | N | |
| H | CH(CH$_2$F)$_2$ | H | H | OCH$_3$ | OCH$_2$CH$_2$F | N | |
| H | CH(CH$_2$F)$_2$ | H | H | OCH$_3$ | OCH$_2$CHF$_2$ | N | |
| H | CH(CH$_3$)CCl$_3$ | H | H | CH$_3$ | OCH$_2$CH$_2$F | N | |
| H | CH(CH$_3$)CCl$_3$ | H | H | CH$_3$ | OCH$_2$CHF$_2$ | N | |
| H | CH(CH$_3$)CCl$_3$ | H | H | OCH$_3$ | OCH$_2$CH$_2$F | N | |
| H | CH(CH$_3$)CCl$_3$ | H | H | OCH$_3$ | OCH$_2$CHF$_2$ | N | |
| H | CH$_2$CH$_2$CHClCH$_3$ | H | H | CH$_3$ | OCH$_2$CH$_2$F | N | |
| H | CH$_2$CH$_2$CHClCH$_3$ | H | H | CH$_3$ | OCH$_2$CHF$_2$ | N | |
| H | CH$_2$CH$_2$CHClCH$_3$ | H | H | OCH$_3$ | OCH$_2$CH$_2$F | N | |
| H | CH$_2$CH$_2$CHClCH$_3$ | H | H | OCH$_3$ | OCH$_2$CHF$_2$ | N | |
| H | CH$_2$CH$_2$CHBrCH$_3$ | H | H | CH$_3$ | OCH$_2$CH$_2$F | N | |
| H | CH$_2$CH$_2$CHBrCH$_3$ | H | H | CH$_3$ | OCH$_2$CHF$_2$ | N | |
| H | CH$_2$CH$_2$CHBrCH$_3$ | H | H | OCH$_3$ | OCH$_2$CH$_2$F | N | |
| H | CH$_2$CH$_2$CHBrCH$_3$ | H | H | OCH$_3$ | OCH$_2$CHF$_2$ | N | |
| H | CH$_2$CH$_2$CHFCH$_3$ | H | H | CH$_3$ | OCH$_2$CH$_2$F | N | |
| H | CH$_2$CH$_2$CHFCH$_3$ | H | H | CH$_3$ | OCH$_2$CHF$_2$ | N | |
| H | CH$_2$CH$_2$CHFCH$_3$ | H | H | OCH$_3$ | OCH$_2$CH$_2$F | N | |
| H | CH$_2$CH$_2$CHFCH$_3$ | H | H | OCH$_3$ | OCH$_2$CHF$_2$ | N | |
| H | CH$_2$CHClCH$_2$CH$_3$ | H | H | CH$_3$ | OCH$_2$CH$_2$F | N | |
| H | CH$_2$CHClCH$_2$CH$_3$ | H | H | CH$_3$ | OCH$_2$CHF$_2$ | N | |
| H | CH$_2$CHClCH$_2$CH$_3$ | H | H | OCH$_3$ | OCH$_2$CH$_2$F | N | |
| H | CH$_2$CHClCH$_2$CH$_3$ | H | H | OCH$_3$ | OCH$_2$CHF$_2$ | N | |
| H | CH$_2$CHBrCH$_2$CH$_3$ | H | H | CH$_3$ | OCH$_2$CH$_2$F | N | |
| H | CH$_2$CHBrCH$_2$CH$_3$ | H | H | CH$_3$ | OCH$_2$CHF$_2$ | N | |
| H | CH$_2$CHBrCH$_2$CH$_3$ | H | H | OCH$_3$ | OCH$_2$CH$_2$F | N | |
| H | CH$_2$CHBrCH$_2$CH$_3$ | H | H | OCH$_3$ | OCH$_2$CHF$_2$ | N | |
| H | CH$_2$CHFCH$_2$CH$_3$ | H | H | CH$_3$ | OCH$_2$CH$_2$F | N | |

TABLE VIa-continued

General Structure VIa

| R2 | R5 | R6 | R | X | Y | Z | m.p. (°C.) |
|---|---|---|---|---|---|---|---|
| H | CH2CHFCH2CH3 | H | H | CH3 | OCH2CHF2 | N | |
| H | CH2CHFCH2CH3 | H | H | OCH3 | OCH2CH2F | N | |
| H | CH2CHFCH2CH3 | H | H | OCH3 | OCH2CHF2 | N | |
| H | CH(CH3)CHClCH3 | H | H | CH3 | OCH2CH2F | N | |
| H | CH(CH3)CHClCH3 | H | H | CH3 | OCH2CHF2 | N | |
| H | CH(CH3)CHClCH3 | H | H | OCH3 | OCH2CH2F | N | |
| H | CH(CH3)CHClCH3 | H | H | OCH3 | OCH2CHF2 | N | |
| H | CH(CH3)CHBrCH3 | H | H | CH3 | OCH2CH2F | N | |
| H | CH(CH3)CHBrCH3 | H | H | CH3 | OCH2CHF2 | N | |
| H | CH(CH3)CHBrCH3 | H | H | OCH3 | OCH2CH2F | N | |
| H | CH(CH3)CHBrCH3 | H | H | OCH3 | OCH2CHF2 | N | |
| H | CH(CH3)CHFCH3 | H | H | CH3 | OCH2CH2F | N | |
| H | CH(CH3)CHFCH3 | H | H | CH3 | OCH2CHF2 | N | |
| H | CH(CH3)CHFCH3 | H | H | OCH3 | OCH2CH2F | N | |
| H | CH(CH3)CHFCH3 | H | H | OCH3 | OCH2CHF2 | N | |
| H | CH2CCl2CH3 | H | H | CH3 | OCH2CH2F | N | |
| H | CH2CCl2CH3 | H | H | CH3 | OCH2CHF2 | N | |
| H | CH2CCl2CH3 | H | H | OCH3 | OCH2CH2F | N | |
| H | CH2CCl2CH3 | H | H | OCH3 | OCH2CHF2 | N | |
| H | CH2CH(CH3)CH2Cl | H | H | CH3 | OCH2CH2F | N | |
| H | CH2CH(CH3)CH2Cl | H | H | CH3 | OCH2CHF2 | N | |
| H | CH2CH(CH3)CH2Cl | H | H | OCH3 | OCH2CH2F | N | |
| H | CH2CH(CH3)CH2Cl | H | H | OCH3 | OCH2CHF2 | N | |
| H | CH2CH(CH3)CH2Br | H | H | CH3 | OCH2CH2F | N | |
| H | CH2CH(CH3)CH2Br | H | H | CH3 | OCH2CHF2 | N | |
| H | CH2CH(CH3)CH2Br | H | H | OCH3 | OCH2CH2F | N | |
| H | CH2CH(CH3)CH2Br | H | H | OCH3 | OCH2CHF2 | N | |
| H | CH2CH(CH3)CH2F | H | H | CH3 | OCH2CH2F | N | |
| H | CH2CH(CH3)CH2F | H | H | CH3 | OCH2CHF2 | N | |
| H | CH2CH(CH3)CH2F | H | H | OCH3 | OCH2CH2F | N | |
| H | CH2CH(CH3)CH2F | H | H | OCH3 | OCH2CHF2 | N | |
| H | CH2CF2Cl | H | H | CH3 | OCH2CH2F | N | |
| H | CH2CF2Cl | H | H | CH3 | OCH2CHF2 | N | |
| H | CH2CF2Cl | H | H | OCH3 | OCH2CH2F | N | |
| H | CH2CF2Cl | H | H | OCH3 | OCH2CHF2 | N | |
| H | CH(CHCl2)CH2Cl | H | H | CH3 | OCH2CH2F | N | |
| H | CH(CHCl2)CH2Cl | H | H | CH3 | OCH2CHF2 | N | |
| H | CH(CHCl2)CH2Cl | H | H | OCH3 | OCH2CH2F | N | |
| H | CH(CHCl2)CH2Cl | H | H | OCH3 | OCH2CHF2 | N | |
| H | CH(CHCl2)CH2F | H | H | CH3 | OCH2CH2F | N | |
| H | CH(CHCl2)CH2F | H | H | CH3 | OCH2CHF2 | N | |
| H | CH(CHCl2)CH2F | H | H | OCH3 | OCH2CH2F | N | |
| H | CH(CHCl2)CH2F | H | H | OCH3 | OCH2CHF2 | N | |
| H | CH(CH2Cl)CH2CH2Cl | H | H | CH3 | OCH2CH2F | N | |
| H | CH(CH2Cl)CH2CH2Cl | H | H | CH3 | OCH2CHF2 | N | |
| H | CH(CH2Cl)CH2CH2Cl | H | H | OCH3 | OCH2CH2F | N | |
| H | CH(CH2Cl)CH2CH2Cl | H | H | OCH3 | OCH2CHF2 | N | |
| H | CH2Br | H | H | CH3 | OCH2CH2F | N | |
| H | CH2Br | H | H | CH3 | OCH2CHF2 | N | |
| H | CH2Br | H | H | OCH3 | OCH2CH2F | N | |
| H | CH2Br | H | H | OCH3 | OCH2CHF2 | N | |
| H | CH2Cl | H | H | CH3 | OCH2CH2F | N | |
| H | CH2Cl | H | H | CH3 | OCH2CHF2 | N | |
| H | CH2Cl | H | H | OCH3 | OCH2CH2F | N | |
| H | CH2Cl | H | H | OCH3 | OCH2CHF2 | N | |
| H | CHCl2 | H | H | CH3 | OCH2CH2F | N | |
| H | CHCl2 | H | H | CH3 | OCH2CHF2 | N | |
| H | CHCl2 | H | H | OCH3 | OCH2CH2F | N | |
| H | CHCl2 | H | H | OCH3 | OCH2CHF2 | N | |
| H | CCl3 | H | H | CH3 | OCH2CH2F | N | |
| H | CCl3 | H | H | CH3 | OCH2CHF2 | N | |
| H | CCl3 | H | H | OCH3 | OCH2CH2F | N | |
| H | CCl3 | H | H | OCH3 | OCH2CHF2 | N | |

TABLE VII

General Structure VII

| R2 | R5 | R | X | Y | Z | m.p. (°C.) |
|---|---|---|---|---|---|---|
| H | CH3 | H | CH3 | OCH2CHF2 | CH | |
| H | CH3 | H | CH3 | OCH2CH2F | CH | |
| H | CH3 | H | CH3 | OCH2CHF2 | N | |
| H | CH3 | H | CH3 | OCH2CH2F | N | |
| H | CH3 | H | OCH3 | OCH2CH2F | N | |
| H | CH3 | H | OCH3 | OCH2CHF2 | N | |
| H | C2H5 | H | CH3 | OCH2CH2F | CH | |
| H | C2H5 | H | OCH3 | OCH2CH2F | N | |
| H | C2H5 | H | OCH3 | OCH2CHF2 | N | |

TABLE VII-continued

General Structure VII

| R₂ | R₅ | R | X | Y | Z | m.p. (°C.) |
|---|---|---|---|---|---|---|
| H | CH(CH₃)₂ | H | OCH₃ | OCH₂CHF₂ | N | |
| H | CH(CH₃)₂ | H | OCH₃ | OCH₂CH₂F | N | |
| H | CH(CH₃)₂ | H | CH₃ | OCH₂CH₂F | CH | |
| H | CH₂CH₂CH₃ | H | CH₃ | OCH₂CH₂F | CH | |
| H | CH₂CH₂CH₃ | H | OCH₃ | OCH₂CH₂F | N | |
| H | CH₂CH₂CH₃ | H | OCH₃ | OCH₂CHF₂ | N | |
| H | (CH₂)₃CH₃ | H | OCH₃ | OCH₂CHF₂ | N | |
| H | (CH₂)₃CH₃ | H | OCH₃ | OCH₂CH₂F | N | |
| H | (CH₂)₃CH₃ | H | CH₃ | OCH₂CH₂F | CH | |
| H | CH₂CH(CH₃)₂ | H | CH₃ | OCH₂CH₂F | CH | |
| H | CH₂CH(CH₃)₂ | H | OCH₃ | OCH₂CH₂F | N | |
| H | CH₂CH(CH₃)₂ | H | OCH₃ | OCH₂CHF₂ | N | |
| H | CH(CH₃)C₂H₅ | H | OCH₃ | OCH₂CHF₂ | N | |
| H | CH(CH₃)C₂H₅ | H | OCH₃ | OCH₂CH₂F | N | |
| H | CH(CH₃)C₂H₅ | H | CH₃ | OCH₂CH₂F | N | |
| H | (CH₂)₄CH₃ | H | CH₃ | OCH₂CH₂F | CH | |
| H | (CH₂)₄CH₃ | H | OCH₃ | OCH₂CH₂F | N | |
| H | (CH₂)₄CH₃ | H | OCH₃ | OCH₂CHF₂ | N | |
| H | CH(CH₃)(CH₂)₂CH₃ | H | OCH₃ | OCH₂CHF₂ | N | |
| H | CH(CH₃)(CH₂)₂CH₃ | H | OCH₃ | OCH₂CH₂F | N | |
| H | CH(CH₃)(CH₂)₂CH₃ | H | CH₃ | OCH₂CHF₂ | CH | |
| H | CH₂CH₂OCH₃ | H | CH₃ | OCH₂CH₂F | CH | |
| H | CH₂CH₂OCH₃ | H | OCH₃ | OCH₂CH₂F | N | |
| H | CH₂CH₂OCH₃ | H | OCH₃ | OCH₂CHF₂ | N | |
| H | CH₂CH₂OC₂H₅ | H | OCH₃ | OCH₂CHF₂ | N | |
| H | CH₂CH₂OC₂H₅ | H | OCH₃ | OCH₂CH₂F | N | |
| H | CH₂CH₂OC₂H₅ | H | CH₃ | OCH₂CH₂F | CH | |
| H | CHF₂ | H | CH₃ | OCH₂CH₂F | CH | |
| H | CHF₂ | H | OCH₃ | OCH₂CH₂F | N | |
| H | CHF₂ | H | OCH₃ | OCH₂CHF₂ | N | |
| H | CF₃ | H | OCH₃ | OCH₂CHF₂ | N | |
| H | CF₃ | H | OCH₃ | OCH₂CH₂F | N | |
| H | CH₂CH₂F | H | OCH₃ | OCH₂CHF₂ | N | |
| H | CH₂CH₂F | H | OCH₃ | OCH₂CH₂F | N | |
| H | CH₂CF₃ | H | OCH₃ | OCH₂CHF₂ | N | |
| H | CH₂CF₃ | H | OCH₃ | OCH₂CH₂F | N | |
| H | CH₂CCl₃ | H | OCH₃ | OCH₂CH₂F | N | |
| H | CH₂CCl₃ | H | OCH₃ | OCH₂CHF₂ | N | |
| H | CH₂CH₂Cl | H | OCH₃ | OCH₂CHF₂ | N | |
| H | CH₂CH₂Cl | H | OCH₃ | OCH₂CH₂F | N | |
| H | CH₂CHCl₂ | H | OCH₃ | OCH₂CH₂F | N | |
| H | CH₂CHCl₂ | H | OCH₃ | OCH₂CHF₂ | N | |
| H | (CH₂)₃Cl | H | OCH₃ | OCH₂CH₂F | N | |
| H | (CH₂)₃Cl | H | OCH₃ | OCH₂CHF₂ | N | |
| H | (CH₂)₃Cl | H | CH₃ | OCH₂CHF₂ | CH | |
| H | (CH₂)₄Cl | H | CH₃ | OCH₂CHF₂ | CH | |
| H | (CH₂)₄Cl | H | OCH₃ | OCH₂CHF₂ | N | |
| H | (CH₂)₄Cl | H | OCH₃ | OCH₂CH₂F | N | |
| H | CH(CH₃)CH₂Cl | H | OCH₃ | OCH₂CH₂F | N | |
| H | CH(CH₃)CH₂Cl | H | OCH₃ | OCH₂CHF₂ | N | |
| H | CH₂CH₂Br | H | OCH₃ | OCH₂CHF₂ | N | |
| H | CH₂CH₂Br | H | OCH₃ | OCH₂CH₂F | N | |
| H | (CH₂)₃Br | H | OCH₃ | OCH₂CH₂F | N | |
| H | (CH₂)₃Br | H | OCH₃ | OCH₂CHF₂ | N | |
| 5-Cl | CH₃ | H | OCH₃ | OCH₂CHF₂ | N | |
| 5-Cl | CH₃ | H | OCH₃ | OCH₂CH₂F | N | |
| 6-Cl | CH₃ | H | OCH₃ | OCH₂CH₂F | N | |
| 6-OCH₃ | CH₃ | H | OCH₃ | OCH₂CH₂F | N | |
| 6-Br | CH₃ | H | OCH₃ | OCH₂CH₂F | N | |
| H | CH₃ | H | CH₃ | OCH₂CHF₂ | CH | |
| H | CH₃ | H | CH₃ | OCH₂CH₂F | CH | |
| H | CH₃ | H | CH₃ | OCH₂CH₂F | N | |
| H | CH₃ | H | OCH₃ | OCH₂CH₂F | N | |
| H | CH₃ | H | OCH₃ | OCH₂CHF₂ | N | |
| H | C₂H₅ | H | CH₃ | OCH₂CH₂F | CH | |
| H | C₂H₅ | H | OCH₃ | OCH₂CH₂F | N | |
| H | C₂H₅ | H | OCH₃ | OCH₂CHF₂ | N | |
| H | CH(CH₃)₂ | H | OCH₃ | OCH₂CHF₂ | N | |
| H | CH(CH₃)₂ | H | OCH₃ | OCH₂CH₂F | N | |
| H | CH(CH₃)₂ | H | CH₃ | OCH₂CH₂F | CH | |
| H | CH₂CH₂CH₃ | H | CH₃ | OCH₂CH₂F | CH | |
| H | CH₂CH₂CH₃ | H | OCH₃ | OCH₂CH₂F | N | |
| H | CH₂CH₂CH₃ | H | OCH₃ | OCH₂CHF₂ | N | |
| H | (CH₂)₃CH₃ | H | OCH₃ | OCH₂CHF₂ | N | |
| H | (CH₂)₃CH₃ | H | OCH₃ | OCH₂CH₂F | N | |
| H | (CH₂)₃CH₃ | H | CH₃ | OCH₂CH₂F | CH | |
| H | CH₂CH(CH₃)₂ | H | CH₃ | OCH₂CH₂F | CH | |
| H | CH₂CH(CH₃)₂ | H | OCH₃ | OCH₂CH₂F | N | |
| H | CH₂CH(CH₃)₂ | H | OCH₃ | OCH₂CHF₂ | N | |

TABLE VII-continued

General Structure VII

| R₂ | R₅ | R | X | Y | Z | m.p. (°C.) |
|---|---|---|---|---|---|---|
| H | CH(CH₃)C₂H₅ | H | OCH₃ | OCH₂CHF₂ | N | |
| H | CH(CH₃)C₂H₅ | H | OCH₃ | OCH₂CH₂F | N | |
| H | CH(CH₃)C₂H₅ | H | CH₃ | OCH₂CH₂F | N | |
| H | (CH₂)₄CH₃ | H | CH₃ | OCH₂CH₂F | CH | |
| H | (CH₂)₄CH₃ | H | OCH₃ | OCH₂CH₂F | N | |
| H | (CH₂)₄CH₃ | H | OCH₃ | OCH₂CHF₂ | N | |
| H | CH(CH₃)(CH₂)₂CH₃ | H | OCH₃ | OCH₂CHF₂ | N | |
| H | CH(CH₃)(CH₂)₂CH₃ | H | OCH₃ | OCH₂CH₂F | N | |
| H | CH(CH₃)(CH₂)₂CH₃ | H | CH₃ | OCH₂CHF₂ | CH | |
| H | CH₂CH₂OCH₃ | H | CH₃ | OCH₂CH₂F | CH | |
| H | CH₂CH₂OCH₃ | H | OCH₃ | OCH₂CH₂F | N | |
| H | CH₂CH₂OCH₃ | H | OCH₃ | OCH₂CHF₂ | N | |
| H | CH₂CH₂OC₂H₅ | H | OCH₃ | OCH₂CHF₂ | N | |
| H | CH₂CH₂OC₂H₅ | H | OCH₃ | OCH₂CH₂F | N | |
| H | CH₂CH₂OC₂H₅ | H | CH₃ | OCH₂CH₂F | CH | |
| H | CHF₂ | H | CH₃ | OCH₂CH₂F | CH | |
| H | CHF₂ | H | OCH₃ | OCH₂CH₂F | N | |
| H | CHF₂ | H | OCH₃ | OCH₂CHF₂ | N | |
| H | CF₃ | H | OCH₃ | OCH₂CHF₂ | N | |
| H | CF₃ | H | OCH₃ | OCH₂CH₂F | N | |
| H | CH₂CH₂F | H | OCH₃ | OCH₂CH₂F | N | |
| H | CH₂CH₂F | H | OCH₃ | OCH₂CHF₂ | N | |
| H | CH₂CF₃ | H | OCH₃ | OCH₂CHF₂ | N | |
| H | CH₂CF₃ | H | OCH₃ | OCH₂CH₂F | N | |
| H | CH₂CCl₃ | H | OCH₃ | OCH₂CH₂F | N | |
| H | CH₂CCl₃ | H | OCH₃ | OCH₂CHF₂ | N | |
| H | CH₂CH₂Cl | H | OCH₃ | OCH₂CHF₂ | N | |
| H | CH₂CH₂Cl | H | OCH₃ | OCH₂CH₂F | N | |
| H | CH₂CHCl₂ | H | OCH₃ | OCH₂CH₂F | N | |
| H | CH₂CHCl₂ | H | OCH₃ | OCH₂CHF₂ | N | |
| H | (CH₂)₃Cl | H | OCH₃ | OCH₂CH₂F | N | |
| H | (CH₂)₃Cl | H | OCH₃ | OCH₂CHF₂ | N | |
| H | (CH₂)₃Cl | H | CH₃ | OCH₂CHF₂ | CH | |
| H | (CH₂)₄Cl | H | CH₃ | OCH₂CHF₂ | CH | |
| H | (CH₂)₄Cl | H | OCH₃ | OCH₂CH₂F | N | |
| H | (CH₂)₄Cl | H | OCH₃ | OCH₂CHF₂ | N | |
| H | CH(CH₃)CH₂Cl | H | OCH₃ | OCH₂CH₂F | N | |
| H | CH(CH₃)CH₂Cl | H | OCH₃ | OCH₂CHF₂ | N | |
| H | CH₂CH₂Br | H | OCH₃ | OCH₂CHF₂ | N | |
| H | CH₂CH₂Br | H | OCH₃ | OCH₂CH₂F | N | |
| H | (CH₂)₃Br | H | OCH₃ | OCH₂CH₂F | N | |
| H | (CH₂)₃Br | H | OCH₃ | OCH₂CHF₂ | N | |
| 5-Cl | CH₃ | H | OCH₃ | OCH₂CHF₂ | N | |
| 5-Cl | CH₃ | H | OCH₃ | OCH₂CH₂F | N | |
| 6-Cl | CH₃ | H | OCH₃ | OCH₂CH₂F | N | |
| 6-OCH₃ | CH₃ | H | OCH₃ | OCH₂CH₂F | N | |
| 6-Br | CH₃ | H | OCH₃ | OCH₂CH₂F | N | |
| H | H | H | CH₃ | OCH₂CH₂F | N | |
| H | H | H | CH₃ | OCH₂CHF₂ | N | |
| H | H | H | OCH₃ | OCH₂CH₂F | N | |
| H | H | H | OCH₃ | OCH₂CHF₂ | N | |
| H | CH₂CH₃ | H | CH₃ | OCH₂CH₂F | N | |
| H | CH₂CH₃ | H | CH₃ | OCH₂CHF₂ | N | |
| H | CH(CH₃)₂ | H | CH₃ | OCH₂CH₂F | N | |
| H | CH(CH₃)₂ | H | CH₃ | OCH₂CHF₂ | N | |
| H | CH₂CH₂CH₃ | H | CH₃ | OCH₂CH₂F | N | |
| H | CH₂CH₂CH₃ | H | CH₃ | OCH₂CHF₂ | N | |
| H | (CH₂)₃CH₃ | H | CH₃ | OCH₂CH₂F | N | |
| H | (CH₂)₃CH₃ | H | CH₃ | OCH₂CHF₂ | N | |
| H | CH₂CH(CH₃)₂ | H | CH₃ | OCH₂CH₂F | N | |
| H | CH₂CH(CH₃)₂ | H | CH₃ | OCH₂CHF₂ | N | |
| H | CH(CH₃)C₂H₅ | H | CH₃ | OCH₂CHF₂ | N | |
| H | CH₂CH₂OCH₃ | H | CH₃ | OCH₂CH₂F | N | |
| H | CH₂CH₂OCH₃ | H | CH₃ | OCH₂CHF₂ | N | |
| H | CH₂CH₂OC₂H₅ | H | CH₃ | OCH₂CH₂F | N | |
| H | CH₂CH₂OC₂H₅ | H | CH₃ | OCH₂CHF₂ | N | |
| H | CHF₂ | H | CH₃ | OCH₂CH₂F | N | |
| H | CHF₂ | H | CH₃ | OCH₂CHF₂ | N | |
| H | CF₃ | H | CH₃ | OCH₂CH₂F | N | |
| H | CF₃ | H | CH₃ | OCH₂CHF₂ | N | |
| H | CH₂CH₂F | H | CH₃ | OCH₂CH₂F | N | |
| H | CH₂CH₂F | H | CH₃ | OCH₂CHF₂ | N | |
| H | CH₂CF₃ | H | CH₃ | OCH₂CH₂F | N | |
| H | CH₂CF₃ | H | CH₃ | OCH₂CHF₂ | N | |
| H | CH₂CH₂Cl | H | CH₃ | OCH₂CH₂F | N | |
| H | CH₂CH₂Cl | H | CH₃ | OCH₂CHF₂ | N | |
| H | CH₂CHCl₂ | H | CH₃ | OCH₂CH₂F | N | |
| H | CH₂CHCl₂ | H | CH₃ | OCH₂CHF₂ | N | |
| H | CH₂CCl₃ | H | CH₃ | OCH₂CH₂F | N | |
| H | CH₂CCl₃ | H | CH₃ | OCH₂CHF₂ | N | |

TABLE VII-continued

General Structure VII

| R$_2$ | R$_5$ | R | X | Y | Z | m.p. (°C.) |
|---|---|---|---|---|---|---|
| H | (CH$_2$)$_3$Cl | H | CH$_3$ | OCH$_2$CH$_2$F | N | |
| H | (CH$_2$)$_3$Cl | H | CH$_3$ | OCH$_2$CHF$_2$ | N | |
| H | CH(CH$_3$)CH$_2$Cl | H | CH$_3$ | OCH$_2$CH$_2$F | N | |
| H | CH(CH$_3$)CH$_2$Cl | H | CH$_3$ | OCH$_2$CHF$_2$ | N | |
| H | (CH$_2$)$_4$Cl | H | CH$_3$ | OCH$_2$CH$_2$F | N | |
| H | (CH$_2$)$_4$Cl | H | CH$_3$ | OCH$_2$CHF$_2$ | N | |
| H | (CH$_2$)$_4$F | H | CH$_3$ | OCH$_2$CH$_2$F | N | |
| H | (CH$_2$)$_4$F | H | CH$_3$ | OCH$_2$CHF$_2$ | N | |
| H | (CH$_2$)$_4$F | H | OCH$_3$ | OCH$_2$CH$_2$F | N | |
| H | (CH$_2$)$_4$F | H | OCH$_3$ | OCH$_2$CHF$_2$ | N | |
| H | CH$_2$CH$_2$Br | H | CH$_3$ | OCH$_2$CH$_2$F | N | |
| H | CH$_2$CH$_2$Br | H | CH$_3$ | OCH$_2$CHF$_2$ | N | |
| H | (CH$_2$)$_3$Br | H | CH$_3$ | OCH$_2$CH$_2$F | N | |
| H | (CH$_2$)$_3$Br | H | CH$_3$ | OCH$_2$CHF$_2$ | N | |
| H | (CH$_2$)$_4$Br | H | CH$_3$ | OCH$_2$CH$_2$F | N | |
| H | (CH$_2$)$_4$Br | H | CH$_3$ | OCH$_2$CHF$_2$ | N | |
| H | (CH$_2$)$_4$Br | H | OCH$_3$ | OCH$_2$CH$_2$F | N | |
| H | (CH$_2$)$_4$Br | H | OCH$_3$ | OCH$_2$CHF$_2$ | N | |
| H | (CH$_2$)$_3$F | H | CH$_3$ | OCH$_2$CH$_2$F | N | |
| H | (CH$_2$)$_3$F | H | CH$_3$ | OCH$_2$CHF$_2$ | N | |
| H | (CH$_2$)$_3$F | H | OCH$_3$ | OCH$_2$CH$_2$F | N | |
| H | (CH$_2$)$_3$F | H | OCH$_3$ | OCH$_2$CHF$_2$ | N | |
| H | CH$_2$CHF$_2$ | H | CH$_3$ | OCH$_2$CH$_2$F | N | |
| H | CH$_2$CHF$_2$ | H | CH$_3$ | OCH$_2$CHF$_2$ | N | |
| H | CH$_2$CHF$_2$ | H | OCH$_3$ | OCH$_2$CH$_2$F | N | |
| H | CH$_2$CHF$_2$ | H | OCH$_3$ | OCH$_2$CHF$_2$ | N | |
| H | CH$_2$F | H | CH$_3$ | OCH$_2$CH$_2$F | N | |
| H | CH$_2$F | H | CH$_3$ | OCH$_2$CHF$_2$ | N | |
| H | CH$_2$F | H | OCH$_3$ | OCH$_2$CH$_2$F | N | |
| H | CH$_2$F | H | OCH$_3$ | OCH$_2$CHF$_2$ | N | |
| H | CH$_2$(CH$_3$)CH$_2$Br | H | CH$_3$ | OCH$_2$CH$_2$F | N | |
| H | CH$_2$(CH$_3$)CH$_2$Br | H | CH$_3$ | OCH$_2$CHF$_2$ | N | |
| H | CH$_2$(CH$_3$)CH$_2$Br | H | OCH$_3$ | OCH$_2$CH$_2$F | N | |
| H | CH$_2$(CH$_3$)CH$_2$Br | H | OCH$_3$ | OCH$_2$CHF$_2$ | N | |
| H | CH$_2$(CH$_3$)CH$_2$F | H | CH$_3$ | OCH$_2$CH$_2$F | N | |
| H | CH$_2$(CH$_3$)CH$_2$F | H | CH$_3$ | OCH$_2$CHF$_2$ | N | |
| H | CH$_2$(CH$_3$)CH$_2$F | H | OCH$_3$ | OCH$_2$CH$_2$F | N | |
| H | CH$_2$(CH$_3$)CH$_2$F | H | OCH$_3$ | OCH$_2$CHF$_2$ | N | |
| H | CH$_2$CHClCH$_3$ | H | CH$_3$ | OCH$_2$CH$_2$F | N | |
| H | CH$_2$CHClCH$_3$ | H | CH$_3$ | OCH$_2$CHF$_2$ | N | |
| H | CH$_2$CHClCH$_3$ | H | OCH$_3$ | OCH$_2$CH$_2$F | N | |
| H | CH$_2$CHClCH$_3$ | H | OCH$_3$ | OCH$_2$CHF$_2$ | N | |
| H | CH$_2$CHBrCH$_3$ | H | CH$_3$ | OCH$_2$CH$_2$F | N | |
| H | CH$_2$CHBrCH$_3$ | H | CH$_3$ | OCH$_2$CHF$_2$ | N | |
| H | CH$_2$CHBrCH$_3$ | H | OCH$_3$ | OCH$_2$CH$_2$F | N | |
| H | CH$_2$CHBrCH$_3$ | H | OCH$_3$ | OCH$_2$CHF$_2$ | N | |
| H | CH$_2$CHFCH$_3$ | H | CH$_3$ | OCH$_2$CH$_2$F | N | |
| H | CH$_2$CHFCH$_3$ | H | CH$_3$ | OCH$_2$CHF$_2$ | N | |
| H | CH$_2$CHFCH$_3$ | H | OCH$_3$ | OCH$_2$CH$_2$F | N | |
| H | CH$_2$CHFCH$_3$ | H | OCH$_3$ | OCH$_2$CHF$_2$ | N | |
| H | CH(CH$_2$Cl)$_2$ | H | CH$_3$ | OCH$_2$CH$_2$F | N | |
| H | CH(CH$_2$Cl)$_2$ | H | CH$_3$ | OCH$_2$CHF$_2$ | N | |
| H | CH(CH$_2$Cl)$_2$ | H | OCH$_3$ | OCH$_2$CH$_2$F | N | |
| H | CH(CH$_2$Cl)$_2$ | H | OCH$_3$ | OCH$_2$CHF$_2$ | N | |
| H | CH(CH$_2$F)$_2$ | H | CH$_3$ | OCH$_2$CH$_2$F | N | |
| H | CH(CH$_2$F)$_2$ | H | CH$_3$ | OCH$_2$CHF$_2$ | N | |
| H | CH(CH$_2$F)$_2$ | H | OCH$_3$ | OCH$_2$CH$_2$F | N | |
| H | CH(CH$_2$F)$_2$ | H | OCH$_3$ | OCH$_2$CHF$_2$ | N | |
| H | CH(CH$_3$)CCl$_3$ | H | CH$_3$ | OCH$_2$CH$_2$F | N | |
| H | CH(CH$_3$)CCl$_3$ | H | CH$_3$ | OCH$_2$CHF$_2$ | N | |
| H | CH(CH$_3$)CCl$_3$ | H | OCH$_3$ | OCH$_2$CH$_2$F | N | |
| H | CH(CH$_3$)CCl$_3$ | H | OCH$_3$ | OCH$_2$CHF$_2$ | N | |
| H | CH$_2$CH$_2$CHClCH$_3$ | H | CH$_3$ | OCH$_2$CH$_2$F | N | |
| H | CH$_2$CH$_2$CHClCH$_3$ | H | CH$_3$ | OCH$_2$CHF$_2$ | N | |
| H | CH$_2$CH$_2$CHClCH$_3$ | H | OCH$_3$ | OCH$_2$CH$_2$F | N | |
| H | CH$_2$CH$_2$CHClCH$_3$ | H | OCH$_3$ | OCH$_2$CHF$_2$ | N | |
| H | CH$_2$CH$_2$CHBrCH$_3$ | H | CH$_3$ | OCH$_2$CH$_2$F | N | |
| H | CH$_2$CH$_2$CHBrCH$_3$ | H | CH$_3$ | OCH$_2$CHF$_2$ | N | |
| H | CH$_2$CH$_2$CHBrCH$_3$ | H | OCH$_3$ | OCH$_2$CH$_2$F | N | |
| H | CH$_2$CH$_2$CHBrCH$_3$ | H | OCH$_3$ | OCH$_2$CHF$_2$ | N | |
| H | CH$_2$CH$_2$CHFCH$_3$ | H | CH$_3$ | OCH$_2$CH$_2$F | N | |
| H | CH$_2$CH$_2$CHFCH$_3$ | H | CH$_3$ | OCH$_2$CHF$_2$ | N | |
| H | CH$_2$CH$_2$CHFCH$_3$ | H | OCH$_3$ | OCH$_2$CH$_2$F | N | |
| H | CH$_2$CH$_2$CHFCH$_3$ | H | OCH$_3$ | OCH$_2$CHF$_2$ | N | |
| H | CH$_2$CHClCH$_2$CH$_3$ | H | CH$_3$ | OCH$_2$CH$_2$F | N | |
| H | CH$_2$CHClCH$_2$CH$_3$ | H | CH$_3$ | OCH$_2$CHF$_2$ | N | |
| H | CH$_2$CHClCH$_2$CH$_3$ | H | OCH$_3$ | OCH$_2$CH$_2$F | N | |
| H | CH$_2$CHClCH$_2$CH$_3$ | H | OCH$_3$ | OCH$_2$CHF$_2$ | N | |
| H | CH$_2$CHBrCH$_2$CH$_3$ | H | CH$_3$ | OCH$_2$CH$_2$F | N | |
| H | CH$_2$CHBrCH$_2$CH$_3$ | H | CH$_3$ | OCH$_2$CHF$_2$ | N | |

TABLE VII-continued

General Structure VII

| R₂ | R₅ | R | X | Y | Z | m.p. (°C.) |
|---|---|---|---|---|---|---|
| H | CH₂CHBrCH₂CH₃ | H | OCH₃ | OCH₂CH₂F | N | |
| H | CH₂CHBrCH₂CH₃ | H | OCH₃ | OCH₂CHF₂ | N | |
| H | CH₂CHFCH₂CH₃ | H | CH₃ | OCH₂CH₂F | N | |
| H | CH₂CHFCH₂CH₃ | H | CH₃ | OCH₂CHF₂ | N | |
| H | CH₂CHFCH₂CH₃ | H | OCH₃ | OCH₂CH₂F | N | |
| H | CH₂CHFCH₂CH₃ | H | OCH₃ | OCH₂CHF₂ | N | |
| H | CH(CH₃)CHClCH₃ | H | CH₃ | OCH₂CH₂F | N | |
| H | CH(CH₃)CHClCH₃ | H | CH₃ | OCH₂CHF₂ | N | |
| H | CH(CH₃)CHClCH₃ | H | OCH₃ | OCH₂CH₂F | N | |
| H | CH(CH₃)CHClCH₃ | H | OCH₃ | OCH₂CHF₂ | N | |
| H | CH(CH₃)CHBrCH₃ | H | CH₃ | OCH₂CH₂F | N | |
| H | CH(CH₃)CHBrCH₃ | H | CH₃ | OCH₂CHF₂ | N | |
| H | CH(CH₃)CHBrCH₃ | H | OCH₃ | OCH₂CH₂F | N | |
| H | CH(CH₃)CHBrCH₃ | H | OCH₃ | OCH₂CHF₂ | N | |
| H | CH(CH₃)CHFCH₃ | H | CH₃ | OCH₂CH₂F | N | |
| H | CH(CH₃)CHFCH₃ | H | CH₃ | OCH₂CHF₂ | N | |
| H | CH(CH₃)CHFCH₃ | H | OCH₃ | OCH₂CH₂F | N | |
| H | CH(CH₃)CHFCH₃ | H | OCH₃ | OCH₂CHF₂ | N | |
| H | CH₂CCl₂CH₃ | H | CH₃ | OCH₂CH₂F | N | |
| H | CH₂CCl₂CH₃ | H | CH₃ | OCH₂CHF₂ | N | |
| H | CH₂CCl₂CH₃ | H | OCH₃ | OCH₂CH₂F | N | |
| H | CH₂CCl₂CH₃ | H | OCH₃ | OCH₂CHF₂ | N | |
| H | CH₂CH(CH₃)CH₂Cl | H | CH₃ | OCH₂CH₂F | N | |
| H | CH₂CH(CH₃)CH₂Cl | H | CH₃ | OCH₂CHF₂ | N | |
| H | CH₂CH(CH₃)CH₂Cl | H | OCH₃ | OCH₂CH₂F | N | |
| H | CH₂CH(CH₃)CH₂Cl | H | OCH₃ | OCH₂CHF₂ | N | |
| H | CH₂CH(CH₃)CH₂Br | H | CH₃ | OCH₂CH₂F | N | |
| H | CH₂CH(CH₃)CH₂Br | H | CH₃ | OCH₂CHF₂ | N | |
| H | CH₂CH(CH₃)CH₂Br | H | OCH₃ | OCH₂CH₂F | N | |
| H | CH₂CH(CH₃)CH₂Br | H | OCH₃ | OCH₂CHF₂ | N | |
| H | CH₂CH(CH₃)CH₂F | H | CH₃ | OCH₂CH₂F | N | |
| H | CH₂CH(CH₃)CH₂F | H | CH₃ | OCH₂CHF₂ | N | |
| H | CH₂CH(CH₃)CH₂F | H | OCH₃ | OCH₂CH₂F | N | |
| H | CH₂CH(CH₃)CH₂F | H | OCH₃ | OCH₂CHF₂ | N | |
| H | CH₂CF₂Cl | H | CH₃ | OCH₂CH₂F | N | |
| H | CH₂CF₂Cl | H | CH₃ | OCH₂CHF₂ | N | |
| H | CH₂CF₂Cl | H | OCH₃ | OCH₂CH₂F | N | |
| H | CH₂CF₂Cl | H | OCH₃ | OCH₂CHF₂ | N | |
| H | CH(CHCl₂)CH₂Cl | H | CH₃ | OCH₂CH₂F | N | |
| H | CH(CHCl₂)CH₂Cl | H | CH₃ | OCH₂CHF₂ | N | |
| H | CH(CHCl₂)CH₂Cl | H | OCH₃ | OCH₂CH₂F | N | |
| H | CH(CHCl₂)CH₂Cl | H | OCH₃ | OCH₂CHF₂ | N | |
| H | CH(CHCl₂)CH₂F | H | CH₃ | OCH₂CH₂F | N | |
| H | CH(CHCl₂)CH₂F | H | CH₃ | OCH₂CHF₂ | N | |
| H | CH(CHCl₂)CH₂F | H | OCH₃ | OCH₂CH₂F | N | |
| H | CH(CHCl₂)CH₂F | H | OCH₃ | OCH₂CHF₂ | N | |
| H | CH(CH₂Cl)CH₂CH₂Cl | H | CH₃ | OCH₂CH₂F | N | |
| H | CH(CH₂Cl)CH₂CH₂Cl | H | CH₃ | OCH₂CHF₂ | N | |
| H | CH(CH₂Cl)CH₂CH₂Cl | H | OCH₃ | OCH₂CH₂F | N | |
| H | CH(CH₂Cl)CH₂CH₂Cl | H | OCH₃ | OCH₂CHF₂ | N | |
| H | CH₂Br | H | CH₃ | OCH₂CH₂F | N | |
| H | CH₂Br | H | CH₃ | OCH₂CHF₂ | N | |
| H | CH₂Br | H | OCH₃ | OCH₂CH₂F | N | |
| H | CH₂Br | H | OCH₃ | OCH₂CHF₂ | N | |
| H | CH₂Cl | H | CH₃ | OCH₂CH₂F | N | |
| H | CH₂Cl | H | CH₃ | OCH₂CHF₂ | N | |
| H | CH₂Cl | H | OCH₃ | OCH₂CH₂F | N | |
| H | CH₂Cl | H | OCH₃ | OCH₂CHF₂ | N | |
| H | CHCl₂ | H | CH₃ | OCH₂CH₂F | N | |
| H | CHCl₂ | H | CH₃ | OCH₂CHF₂ | N | |
| H | CHCl₂ | H | OCH₃ | OCH₂CH₂F | N | |
| H | CHCl₂ | H | OCH₃ | OCH₂CHF₂ | N | |
| H | CCl₃ | H | CH₃ | OCH₂CH₂F | N | |
| H | CCl₃ | H | CH₃ | OCH₂CHF₂ | N | |
| H | CCl₃ | H | OCH₃ | OCH₂CH₂F | N | |
| H | CCl₃ | H | OCH₃ | OCH₂CHF₂ | N | |

TABLE VIII

General Structure VIII

| R₂ | R₅ | R₇ | R | X | Y | Z | m.p. (°C.) |
|---|---|---|---|---|---|---|---|
| H | CH₃ | H | H | CH₃ | OCH₂CHF₂ | CH | |
| H | CH₃ | H | H | CH₃ | OCH₂CH₂F | CH | |
| H | CH₃ | H | H | CH₃ | OCH₂CHF₂ | N | |
| H | CH₃ | H | H | CH₃ | OCH₂CH₂F | N | |
| H | CH₃ | H | H | OCH₃ | OCH₂CH₂F | N | |
| H | CH₃ | H | H | OCH₃ | OCH₂CHF₂ | N | |
| H | C₂H₅ | H | H | CH₃ | OCH₂CH₂F | CH | |

TABLE VIII-continued

General Structure VIII

| R$_2$ | R$_5$ | R$_7$ | R | X | Y | Z | m.p. (°C.) |
|---|---|---|---|---|---|---|---|
| H | C$_2$H$_5$ | H | H | OCH$_3$ | OCH$_2$CH$_2$F | N | |
| H | C$_2$H$_5$ | H | H | OCH$_3$ | OCH$_2$CHF$_2$ | N | |
| H | CH(CH$_3$)$_2$ | H | H | OCH$_3$ | OCH$_2$CHF$_2$ | N | |
| H | CH(CH$_3$)$_2$ | H | H | OCH$_3$ | OCH$_2$CH$_2$F | N | |
| H | CH(CH$_3$)$_2$ | H | H | CH$_3$ | OCH$_2$CH$_2$F | CH | |
| H | CH$_2$CH$_2$CH$_3$ | H | H | CH$_3$ | OCH$_2$CH$_2$F | CH | |
| H | CH$_2$CH$_2$CH$_3$ | H | H | OCH$_3$ | OCH$_2$CH$_2$F | N | |
| H | CH$_2$CH$_2$CH$_3$ | H | H | OCH$_3$ | OCH$_2$CHF$_2$ | N | |
| H | (CH$_2$)$_3$CH$_3$ | H | H | OCH$_3$ | OCH$_2$CHF$_2$ | N | |
| H | (CH$_2$)$_3$CH$_3$ | H | H | OCH$_3$ | OCH$_2$CH$_2$F | N | |
| H | (CH$_2$)$_3$CH$_3$ | H | H | CH$_3$ | OCH$_2$CH$_2$F | CH | |
| H | CH$_2$CH(CH$_3$)$_2$ | H | H | CH$_3$ | OCH$_2$CH$_2$F | CH | |
| H | CH$_2$CH(CH$_3$)$_2$ | H | H | OCH$_3$ | OCH$_2$CH$_2$F | N | |
| H | CH$_2$CH(CH$_3$)$_2$ | H | H | OCH$_3$ | OCH$_2$CHF$_2$ | N | |
| H | CH(CH$_3$)C$_2$H$_5$ | H | H | OCH$_3$ | OCH$_2$CHF$_2$ | N | |
| H | CH(CH$_3$)C$_2$H$_5$ | H | H | OCH$_3$ | OCH$_2$CH$_2$F | N | |
| H | CH(CH$_3$)C$_2$H$_5$ | H | H | CH$_3$ | OCH$_2$CH$_2$F | CH | |
| H | (CH$_2$)$_4$CH$_3$ | H | H | CH$_3$ | OCH$_2$CH$_2$F | CH | |
| H | (CH$_2$)$_4$CH$_3$ | H | H | OCH$_3$ | OCH$_2$CH$_2$F | N | |
| H | (CH$_2$)$_4$CH$_3$ | H | H | OCH$_3$ | OCH$_2$CHF$_2$ | N | |
| H | CH(CH$_3$)(CH$_2$)$_2$CH$_3$ | H | H | OCH$_3$ | OCH$_2$CHF$_2$ | N | |
| H | CH(CH$_3$)(CH$_2$)$_2$CH$_3$ | H | H | OCH$_3$ | OCH$_2$CH$_2$F | N | |
| H | CH(CH$_3$)(CH$_2$)$_2$CH$_3$ | H | H | CH$_3$ | OCH$_2$CHF$_2$ | CH | |
| H | CH$_2$CH$_2$OCH$_3$ | H | H | CH$_3$ | OCH$_2$CH$_2$F | CH | |
| H | CH$_2$CH$_2$OCH$_3$ | H | H | OCH$_3$ | OCH$_2$CH$_2$F | N | |
| H | CH$_2$CH$_2$OCH$_3$ | H | H | OCH$_3$ | OCH$_2$CHF$_2$ | N | |
| H | CH$_2$CH$_2$OC$_2$H$_5$ | H | H | OCH$_3$ | OCH$_2$CHF$_2$ | N | |
| H | CH$_2$CH$_2$OC$_2$H$_5$ | H | H | OCH$_3$ | OCH$_2$CH$_2$F | N | |
| H | CH$_2$CH$_2$OC$_2$H$_5$ | H | H | CH$_3$ | OCH$_2$CH$_2$F | CH | |
| H | CHF$_2$ | H | H | CH$_3$ | OCH$_2$CH$_2$F | CH | |
| H | CHF$_2$ | H | H | OCH$_3$ | OCH$_2$CH$_2$F | N | |
| H | CHF$_2$ | H | H | OCH$_3$ | OCH$_2$CHF$_2$ | N | |
| H | CF$_3$ | H | H | OCH$_3$ | OCH$_2$CHF$_2$ | N | |
| H | CF$_3$ | H | H | OCH$_3$ | OCH$_2$CH$_2$F | N | |
| H | CH$_2$CH$_2$F | H | H | OCH$_3$ | OCH$_2$CH$_2$F | N | |
| H | CH$_2$CH$_2$F | H | H | OCH$_3$ | OCH$_2$CHF$_2$ | N | |
| H | CH$_2$CF$_3$ | H | H | OCH$_3$ | OCH$_2$CHF$_2$ | N | |
| H | CH$_2$CF$_3$ | H | H | OCH$_3$ | OCH$_2$CH$_2$F | N | |
| H | CH$_2$CCl$_3$ | H | H | OCH$_3$ | OCH$_2$CH$_2$F | N | |
| H | CH$_2$CCl$_3$ | H | H | OCH$_3$ | OCH$_2$CHF$_2$ | N | |
| H | CH$_2$CH$_2$Cl | H | H | OCH$_3$ | OCH$_2$CHF$_2$ | N | |
| H | CH$_2$CH$_2$Cl | H | H | OCH$_3$ | OCH$_2$CH$_2$F | N | |
| H | CH$_2$CHCl$_2$ | H | H | OCH$_3$ | OCH$_2$CH$_2$F | N | |
| H | CH$_2$CHCl$_2$ | H | H | OCH$_3$ | OCH$_2$CHF$_2$ | N | |
| H | (CH$_2$)$_3$Cl | H | H | OCH$_3$ | OCH$_2$CH$_2$F | N | |
| H | (CH$_2$)$_3$Cl | H | H | OCH$_3$ | OCH$_2$CHF$_2$ | N | |
| H | (CH$_2$)$_3$Cl | H | H | CH$_3$ | OCH$_2$CHF$_2$ | CH | |
| H | (CH$_2$)$_4$Cl | H | H | CH$_3$ | OCH$_2$CHF$_2$ | CH | |
| H | (CH$_2$)$_4$Cl | H | H | OCH$_3$ | OCH$_2$CH$_2$F | N | |
| H | (CH$_2$)$_4$Cl | H | H | OCH$_3$ | OCH$_2$CHF$_2$ | N | |
| H | CH(CH$_3$)CH$_2$Cl | H | H | OCH$_3$ | OCH$_2$CH$_2$F | N | |
| H | CH(CH$_3$)CH$_2$Cl | H | H | OCH$_3$ | OCH$_2$CHF$_2$ | N | |
| H | CH$_2$CH$_2$Br | H | H | OCH$_3$ | OCH$_2$CHF$_2$ | N | |
| H | CH$_2$CH$_2$Br | H | H | OCH$_3$ | OCH$_2$CH$_2$F | N | |
| H | (CH$_2$)$_3$Br | H | H | OCH$_3$ | OCH$_2$CH$_2$F | N | |
| H | (CH$_2$)$_3$Br | H | H | OCH$_3$ | OCH$_2$CHF$_2$ | N | |
| 5-Cl | CH$_3$ | H | H | OCH$_3$ | OCH$_2$CHF$_2$ | N | |
| 5-Cl | CH$_3$ | H | H | OCH$_3$ | OCH$_2$CH$_2$F | N | |
| 6-Cl | CH$_3$ | H | H | OCH$_3$ | OCH$_2$CH$_2$F | N | |
| 6-OCH$_3$ | CH$_3$ | H | H | OCH$_3$ | OCH$_2$CH$_2$F | N | |
| 6-Br | CH$_3$ | H | H | OCH$_3$ | OCH$_2$CH$_2$F | N | |
| H | CH$_3$ | CH$_3$ | H | CH$_3$ | OCH$_2$CHF$_2$ | CH | |
| H | CH$_3$ | CH$_3$ | H | CH$_3$ | OCH$_2$CH$_2$F | CH | |
| H | CH$_3$ | CH$_3$ | H | CH$_3$ | OCH$_2$CH$_2$F | N | |
| H | CH$_3$ | CH$_3$ | H | OCH$_3$ | OCH$_2$CH$_2$F | N | |
| H | CH$_3$ | CH$_3$ | H | OCH$_3$ | OCH$_2$CHF$_2$ | N | |
| H | C$_2$H$_5$ | CH$_3$ | H | CH$_3$ | OCH$_2$CH$_2$F | CH | |
| H | C$_2$H$_5$ | CH$_3$ | H | OCH$_3$ | OCH$_2$CH$_2$F | N | |
| H | C$_2$H$_5$ | CH$_3$ | H | OCH$_3$ | OCH$_2$CHF$_2$ | N | |
| H | CH(CH$_3$)$_2$ | CH$_3$ | H | OCH$_3$ | OCH$_2$CHF$_2$ | N | |
| H | CH(CH$_3$)$_2$ | CH$_3$ | H | OCH$_3$ | OCH$_2$CH$_2$F | N | |
| H | CH(CH$_3$)$_2$ | CH$_3$ | H | CH$_3$ | OCH$_2$CH$_2$F | CH | |
| H | CH$_2$CH$_2$CH$_3$ | CH$_3$ | H | CH$_3$ | OCH$_2$CH$_2$F | CH | |
| H | CH$_2$CH$_2$CH$_3$ | CH$_3$ | H | OCH$_3$ | OCH$_2$CH$_2$F | N | |
| H | CH$_2$CH$_2$CH$_3$ | CH$_3$ | H | OCH$_3$ | OCH$_2$CHF$_2$ | N | |
| H | (CH$_2$)$_3$CH$_3$ | CH$_3$ | H | OCH$_3$ | OCH$_2$CHF$_2$ | N | |
| H | (CH$_2$)$_3$CH$_3$ | CH$_3$ | H | OCH$_3$ | OCH$_2$CH$_2$F | N | |
| H | (CH$_2$)$_3$CH$_3$ | CH$_3$ | H | CH$_3$ | OCH$_2$CH$_2$F | CH | |
| H | CH$_2$CH(CH$_3$)$_2$ | CH$_3$ | H | CH$_3$ | OCH$_2$CH$_2$F | CH | |

TABLE VIII-continued

General Structure VIII

| R₂ | R₅ | R₇ | R | X | Y | Z | m.p. (°C.) |
|---|---|---|---|---|---|---|---|
| H | CH₂CH(CH₃)₂ | CH₃ | H | OCH₃ | OCH₂CH₂F | N | |
| H | CH₂CH(CH₃)₂ | CH₃ | H | OCH₃ | OCH₂CHF₂ | N | |
| H | CH(CH₃)C₂H₅ | CH₃ | H | OCH₃ | OCH₂CHF₂ | N | |
| H | CH(CH₃)C₂H₅ | CH₃ | H | OCH₃ | OCH₂CH₂F | N | |
| H | CH(CH₃)C₂H₅ | CH₃ | H | CH₃ | OCH₂CH₂F | N | |
| H | (CH₂)₄CH₃ | CH₃ | H | CH₃ | OCH₂CH₂F | CH | |
| H | (CH₂)₄CH₃ | CH₃ | H | OCH₃ | OCH₂CH₂F | N | |
| H | (CH₂)₄CH₃ | CH₃ | H | OCH₃ | OCH₂CHF₂ | N | |
| H | CH(CH₃)(CH₂)₂CH₃ | CH₃ | H | OCH₃ | OCH₂CHF₂ | N | |
| H | CH(CH₃)(CH₂)₂CH₃ | CH₃ | H | OCH₃ | OCH₂CH₂F | N | |
| H | CH(CH₃)(CH₂)₂CH₃ | CH₃ | H | CH₃ | OCH₂CHF₂ | CH | |
| H | CH₂CH₂OCH₃ | CH₃ | H | CH₃ | OCH₂CH₂F | CH | |
| H | CH₂CH₂OCH₃ | CH₃ | H | OCH₃ | OCH₂CH₂F | N | |
| H | CH₂CH₂OCH₃ | CH₃ | H | OCH₃ | OCH₂CHF₂ | N | |
| H | CH₂CH₂OC₂H₅ | CH₃ | H | OCH₃ | OCH₂CHF₂ | N | |
| H | CH₂CH₂OC₂H₅ | CH₃ | H | OCH₃ | OCH₂CH₂F | N | |
| H | CH₂CH₂OC₂H₅ | CH₃ | H | CH₃ | OCH₂CH₂F | CH | |
| H | CHF₂ | CH₃ | H | CH₃ | OCH₂CH₂F | CH | |
| H | CHF₂ | CH₃ | H | OCH₃ | OCH₂CH₂F | N | |
| H | CHF₂ | CH₃ | H | OCH₃ | OCH₂CHF₂ | N | |
| H | CF₃ | CH₃ | H | OCH₃ | OCH₂CHF₂ | N | |
| H | CF₃ | CH₃ | H | OCH₃ | OCH₂CH₂F | N | |
| H | CH₂CH₂F | CH₃ | H | OCH₃ | OCH₂CH₂F | N | |
| H | CH₂CH₂F | CH₃ | H | OCH₃ | OCH₂CHF₂ | N | |
| H | CH₂CF₃ | CH₃ | H | OCH₃ | OCH₂CH₂F | N | |
| H | CH₂CF₃ | CH₃ | H | OCH₃ | OCH₂CHF₂ | N | |
| H | CH₂CCl₃ | CH₃ | H | OCH₃ | OCH₂CH₂F | N | |
| H | CH₂CCl₃ | CH₃ | H | OCH₃ | OCH₂CHF₂ | N | |
| H | CH₂CH₂Cl | CH₃ | H | OCH₃ | OCH₂CH₂F | N | |
| H | CH₂CH₂Cl | CH₃ | H | OCH₃ | OCH₂CHF₂ | N | |
| H | CH₂CHCl₂ | CH₃ | H | OCH₃ | OCH₂CH₂F | N | |
| H | CH₂CHCl₂ | CH₃ | H | OCH₃ | OCH₂CHF₂ | N | |
| H | (CH₂)₃Cl | CH₃ | H | OCH₃ | OCH₂CH₂F | N | |
| H | (CH₂)₃Cl | CH₃ | H | OCH₃ | OCH₂CHF₂ | N | |
| H | (CH₂)₃Cl | CH₃ | H | CH₃ | OCH₂CHF₂ | CH | |
| H | (CH₂)₄Cl | CH₃ | H | CH₃ | OCH₂CHF₂ | CH | |
| H | (CH₂)₄Cl | CH₃ | H | OCH₃ | OCH₂CHF₂ | N | |
| H | (CH₂)₄Cl | CH₃ | H | OCH₃ | OCH₂CH₂F | N | |
| H | CH(CH₃)CH₂Cl | CH₃ | H | OCH₃ | OCH₂CH₂F | N | |
| H | CH(CH₃)CH₂Cl | CH₃ | H | OCH₃ | OCH₂CHF₂ | N | |
| H | CH₂CH₂Br | CH₃ | H | OCH₃ | OCH₂CH₂F | N | |
| H | CH₂CH₂Br | CH₃ | H | OCH₃ | OCH₂CHF₂ | N | |
| H | (CH₂)₃Br | CH₃ | H | OCH₃ | OCH₂CH₂F | N | |
| H | (CH₂)₃Br | CH₃ | H | OCH₃ | OCH₂CHF₂ | N | |
| 5-Cl | CH₃ | CH₃ | H | OCH₃ | OCH₂CHF₂ | N | |
| 5-Cl | CH₃ | CH₃ | H | OCH₃ | OCH₂CH₂F | N | |
| 6-Cl | CH₃ | CH₃ | H | OCH₃ | OCH₂CH₂F | N | |
| 6-OCH₃ | CH₃ | CH₃ | H | OCH₃ | OCH₂CH₂F | N | |
| 6-Br | CH₃ | CH₃ | H | OCH₃ | OCH₂CH₂F | N | |
| H | H | H | H | CH₃ | OCH₂CH₂F | N | |
| H | H | H | H | CH₃ | OCH₂CHF₂ | N | |
| H | H | H | H | OCH₃ | OCH₂CH₂F | N | |
| H | H | H | H | OCH₃ | OCH₂CHF₂ | N | |
| H | CH₂CH₃ | H | H | CH₃ | OCH₂CH₂F | N | |
| H | CH₃CH₃ | H | H | CH₃ | OCH₂CHF₂ | N | |
| H | CH(CH₃)₂ | H | H | CH₃ | OCH₂CH₂F | N | |
| H | CH(CH₃)₂ | H | H | CH₃ | OCH₂CHF₂ | N | |
| H | CH₂CH₂CH₃ | H | H | CH₃ | OCH₂CH₂F | N | |
| H | CH₂CH₂CH₃ | H | H | CH₃ | OCH₂CHF₂ | N | |
| H | (CH₂)₃CH₃ | H | H | CH₃ | OCH₂CH₂F | N | |
| H | (CH₂)₃CH₃ | H | H | CH₃ | OCH₂CHF₂ | N | |
| H | CH₂CH(CH₃)₂ | H | H | CH₃ | OCH₂CH₂F | N | |
| H | CH₂CH(CH₃)₂ | H | H | CH₃ | OCH₂CHF₂ | N | |
| H | CH(CH₃)C₂H₅ | H | H | CH₃ | OCH₂CHF₂ | N | |
| H | CH₂CH₂OCH₃ | H | H | CH₃ | OCH₂CH₂F | N | |
| H | CH₂CH₂OCH₃ | H | H | CH₃ | OCH₂CHF₂ | N | |
| H | CH₂CH₂OC₂H₅ | H | H | CH₃ | OCH₂CH₂F | N | |
| H | CH₂CH₂OC₂H₅ | H | H | CH₃ | OCH₂CHF₂ | N | |
| H | CHF₂ | H | H | CH₃ | OCH₂CH₂F | N | |
| H | CHF₂ | H | H | CH₃ | OCH₂CHF₂ | N | |
| H | CF₃ | H | H | CH₃ | OCH₂CH₂F | N | |
| H | CF₃ | H | H | CH₃ | OCH₂CHF₂ | N | |
| H | CH₂CH₂F | H | H | CH₃ | OCH₂CH₂F | N | |
| H | CH₂CH₂F | H | H | CH₃ | OCH₂CHF₂ | N | |
| H | CH₂CF₃ | H | H | CH₃ | OCH₂CH₂F | N | |
| H | CH₂CF₃ | H | H | CH₃ | OCH₂CHF₂ | N | |
| H | CH₂CH₂Cl | H | H | CH₃ | OCH₂CH₂F | N | |
| H | CH₂CH₂Cl | H | H | CH₃ | OCH₂CHF₂ | N | |
| H | CH₂CHCl₂ | H | H | CH₃ | OCH₂CH₂F | N | |
| H | CH₂CHCl₂ | H | H | CH₃ | OCH₂CHF₂ | N | |

TABLE VIII-continued

General Structure VIII

| R$_2$ | R$_5$ | R$_7$ | R | X | Y | Z | m.p. (°C.) |
|---|---|---|---|---|---|---|---|
| H | CH$_2$CCl$_3$ | H | H | CH$_3$ | OCH$_2$CH$_2$F | N | |
| H | CH$_2$CCl$_3$ | H | H | CH$_3$ | OCH$_2$CHF$_2$ | N | |
| H | (CH$_2$)$_3$Cl | H | H | CH$_3$ | OCH$_2$CH$_2$F | N | |
| H | (CH$_2$)$_3$Cl | H | H | CH$_3$ | OCH$_2$CHF$_2$ | N | |
| H | CH(CH$_3$)CH$_2$Cl | H | H | CH$_3$ | OCH$_2$CH$_2$F | N | |
| H | CH(CH$_3$)CH$_2$Cl | H | H | CH$_3$ | OCH$_2$CHF$_2$ | N | |
| H | (CH$_2$)$_4$Cl | H | H | CH$_3$ | OCH$_2$CH$_2$F | N | |
| H | (CH$_2$)$_4$Cl | H | H | CH$_3$ | OCH$_2$CHF$_2$ | N | |
| H | (CH$_2$)$_4$F | H | H | CH$_3$ | OCH$_2$CH$_2$F | N | |
| H | (CH$_2$)$_4$F | H | H | CH$_3$ | OCH$_2$CHF$_2$ | N | |
| H | (CH$_2$)$_4$F | H | H | OCH$_3$ | OCH$_2$CH$_2$F | N | |
| H | (CH$_2$)$_4$F | H | H | OCH$_3$ | OCH$_2$CHF$_2$ | N | |
| H | CH$_2$CH$_2$Br | H | H | CH$_3$ | OCH$_2$CH$_2$F | N | |
| H | CH$_2$CH$_2$Br | H | H | CH$_3$ | OCH$_2$CHF$_2$ | N | |
| H | (CH$_2$)$_3$Br | H | H | CH$_3$ | OCH$_2$CH$_2$F | N | |
| H | (CH$_2$)$_3$Br | H | H | CH$_3$ | OCH$_2$CHF$_2$ | N | |
| H | (CH$_2$)$_4$Br | H | H | CH$_3$ | OCH$_2$CH$_2$F | N | |
| H | (CH$_2$)$_4$Br | H | H | CH$_3$ | OCH$_2$CHF$_2$ | N | |
| H | (CH$_2$)$_4$Br | H | H | OCH$_3$ | OCH$_2$CH$_2$F | N | |
| H | (CH$_2$)$_4$Br | H | H | OCH$_3$ | OCH$_2$CHF$_2$ | N | |
| H | (CH$_2$)$_3$F | H | H | CH$_3$ | OCH$_2$CH$_2$F | N | |
| H | (CH$_2$)$_3$F | H | H | CH$_3$ | OCH$_2$CHF$_2$ | N | |
| H | (CH$_2$)$_3$F | H | H | OCH$_3$ | OCH$_2$CH$_2$F | N | |
| H | (CH$_2$)$_3$F | H | H | OCH$_3$ | OCH$_2$CHF$_2$ | N | |
| H | CH$_2$CHF$_2$ | H | H | CH$_3$ | OCH$_2$CH$_2$F | N | |
| H | CH$_2$CHF$_2$ | H | H | CH$_3$ | OCH$_2$CHF$_2$ | N | |
| H | CH$_2$CHF$_2$ | H | H | OCH$_3$ | OCH$_2$CH$_2$F | N | |
| H | CH$_2$CHF$_2$ | H | H | OCH$_3$ | OCH$_2$CHF$_2$ | N | |
| H | CH$_2$F | H | H | CH$_3$ | OCH$_2$CH$_2$F | N | |
| H | CH$_2$F | H | H | CH$_3$ | OCH$_2$CHF$_2$ | N | |
| H | CH$_2$F | H | H | OCH$_3$ | OCH$_2$CH$_2$F | N | |
| H | CH$_2$F | H | H | OCH$_3$ | OCH$_2$CHF$_2$ | N | |
| H | CH$_2$(CH$_3$)CH$_2$Br | H | H | CH$_3$ | OCH$_2$CH$_2$F | N | |
| H | CH$_2$(CH$_3$)CH$_2$Br | H | H | CH$_3$ | OCH$_2$CHF$_2$ | N | |
| H | CH$_2$(CH$_3$)CH$_2$Br | H | H | OCH$_3$ | OCH$_2$CH$_2$F | N | |
| H | CH$_2$(CH$_3$)CH$_2$Br | H | H | OCH$_3$ | OCH$_2$CHF$_2$ | N | |
| H | CH$_2$(CH$_3$)CH$_2$F | H | H | CH$_3$ | OCH$_2$CH$_2$F | N | |
| H | CH$_2$(CH$_3$)CH$_2$F | H | H | CH$_3$ | OCH$_2$CHF$_2$ | N | |
| H | CH$_2$(CH$_3$)CH$_2$F | H | H | OCH$_3$ | OCH$_2$CH$_2$F | N | |
| H | CH$_2$(CH$_3$)CH$_2$F | H | H | OCH$_3$ | OCH$_2$CHF$_2$ | N | |
| H | CH$_2$CHClCH$_3$ | H | H | CH$_3$ | OCH$_2$CH$_2$F | N | |
| H | CH$_2$CHClCH$_3$ | H | H | CH$_3$ | OCH$_2$CHF$_2$ | N | |
| H | CH$_2$CHClCH$_3$ | H | H | OCH$_3$ | OCH$_2$CH$_2$F | N | |
| H | CH$_2$CHClCH$_3$ | H | H | OCH$_3$ | OCH$_2$CHF$_2$ | N | |
| H | CH$_2$CHBrCH$_3$ | H | H | CH$_3$ | OCH$_2$CH$_2$F | N | |
| H | CH$_2$CHBrCH$_3$ | H | H | CH$_3$ | OCH$_2$CHF$_2$ | N | |
| H | CH$_2$CHBrCH$_3$ | H | H | OCH$_3$ | OCH$_2$CH$_2$F | N | |
| H | CH$_2$CHBrCH$_3$ | H | H | OCH$_3$ | OCH$_2$CHF$_2$ | N | |
| H | CH$_2$CHFCH$_3$ | H | H | CH$_3$ | OCH$_2$CH$_2$F | N | |
| H | CH$_2$CHFCH$_3$ | H | H | CH$_3$ | OCH$_2$CHF$_2$ | N | |
| H | CH$_2$CHFCH$_3$ | H | H | OCH$_3$ | OCH$_2$CH$_2$F | N | |
| H | CH$_2$CHFCH$_3$ | H | H | OCH$_3$ | OCH$_2$CHF$_2$ | N | |
| H | CH(CH$_2$Cl)$_2$ | H | H | CH$_3$ | OCH$_2$CH$_2$F | N | |
| H | CH(CH$_2$Cl)$_2$ | H | H | CH$_3$ | OCH$_2$CHF$_2$ | N | |
| H | CH(CH$_2$Cl)$_2$ | H | H | OCH$_3$ | OCH$_2$CH$_2$F | N | |
| H | CH(CH$_2$Cl)$_2$ | H | H | OCH$_3$ | OCH$_2$CHF$_2$ | N | |
| H | CH(CH$_2$F)$_2$ | H | H | CH$_3$ | OCH$_2$CH$_2$F | N | |
| H | CH(CH$_2$F)$_2$ | H | H | CH$_3$ | OCH$_2$CHF$_2$ | N | |
| H | CH(CH$_2$F)$_2$ | H | H | OCH$_3$ | OCH$_2$CH$_2$F | N | |
| H | CH(CH$_2$F)$_2$ | H | H | OCH$_3$ | OCH$_2$CHF$_2$ | N | |
| H | CH(CH$_3$)CCl$_3$ | H | H | CH$_3$ | OCH$_2$CH$_2$F | N | |
| H | CH(CH$_3$)CCl$_3$ | H | H | CH$_3$ | OCH$_2$CHF$_2$ | N | |
| H | CH(CH$_3$)CCl$_3$ | H | H | OCH$_3$ | OCH$_2$CH$_2$F | N | |
| H | CH(CH$_3$)CCl$_3$ | H | H | OCH$_3$ | OCH$_2$CHF$_2$ | N | |
| H | CH$_2$CH$_2$CHClCH$_3$ | H | H | CH$_3$ | OCH$_2$CH$_2$F | N | |
| H | CH$_2$CH$_2$CHClCH$_3$ | H | H | CH$_3$ | OCH$_2$CHF$_2$ | N | |
| H | CH$_2$CH$_2$CHClCH$_3$ | H | H | OCH$_3$ | OCH$_2$CH$_2$F | N | |
| H | CH$_2$CH$_2$CHClCH$_3$ | H | H | OCH$_3$ | OCH$_2$CHF$_2$ | N | |
| H | CH$_2$CH$_2$CHBrCH$_3$ | H | H | CH$_3$ | OCH$_2$CH$_2$F | N | |
| H | CH$_2$CH$_2$CHBrCH$_3$ | H | H | CH$_3$ | OCH$_2$CHF$_2$ | N | |
| H | CH$_2$CH$_2$CHBrCH$_3$ | H | H | OCH$_3$ | OCH$_2$CH$_2$F | N | |
| H | CH$_2$CH$_2$CHBrCH$_3$ | H | H | OCH$_3$ | OCH$_2$CHF$_2$ | N | |
| H | CH$_2$CH$_2$CHFCH$_3$ | H | H | CH$_3$ | OCH$_2$CH$_2$F | N | |
| H | CH$_2$CH$_2$CHFCH$_3$ | H | H | CH$_3$ | OCH$_2$CHF$_2$ | N | |
| H | CH$_2$CH$_2$CHFCH$_3$ | H | H | OCH$_3$ | OCH$_2$CH$_2$F | N | |
| H | CH$_2$CH$_2$CHFCH$_3$ | H | H | OCH$_3$ | OCH$_2$CHF$_2$ | N | |
| H | CH$_2$CHClCH$_2$CH$_3$ | H | H | CH$_3$ | OCH$_2$CH$_2$F | N | |
| H | CH$_2$CHClCH$_2$CH$_3$ | H | H | CH$_3$ | OCH$_2$CHF$_2$ | N | |
| H | CH$_2$CHClCH$_2$CH$_3$ | H | H | OCH$_3$ | OCH$_2$CH$_2$F | N | |
| H | CH$_2$CHClCH$_2$CH$_3$ | H | H | OCH$_3$ | OCH$_2$CHF$_2$ | N | |

TABLE VIII-continued

General Structure VIII

| R₂ | R₅ | R₇ | R | X | Y | Z | m.p. (°C.) |
|---|---|---|---|---|---|---|---|
| H | CH₂CHBrCH₂CH₃ | H | H | CH₃ | OCH₂CH₂F | N | |
| H | CH₂CHBrCH₂CH₃ | H | H | CH₃ | OCH₂CHF₂ | N | |
| H | CH₂CHBrCH₂CH₃ | H | H | OCH₃ | OCH₂CH₂F | N | |
| H | CH₂CHBrCH₂CH₃ | H | H | OCH₃ | OCH₂CHF₂ | N | |
| H | CH₂CHFCH₂CH₃ | H | H | CH₃ | OCH₂CH₂F | N | |
| H | CH₂CHFCH₂CH₃ | H | H | CH₃ | OCH₂CHF₂ | N | |
| H | CH₂CHFCH₂CH₃ | H | H | OCH₃ | OCH₂CH₂F | N | |
| H | CH₂CHFCH₂CH₃ | H | H | OCH₃ | OCH₂CHF₂ | N | |
| H | CH(CH₃)CHClCH₃ | H | H | CH₃ | OCH₂CH₂F | N | |
| H | CH(CH₃)CHClCH₃ | H | H | CH₃ | OCH₂CHF₂ | N | |
| H | CH(CH₃)CHClCH₃ | H | H | OCH₃ | OCH₂CH₂F | N | |
| H | CH(CH₃)CHClCH₃ | H | H | OCH₃ | OCH₂CHF₂ | N | |
| H | CH(CH₃)CHBrCH₃ | H | H | CH₃ | OCH₂CH₂F | N | |
| H | CH(CH₃)CHBrCH₃ | H | H | CH₃ | OCH₂CHF₂ | N | |
| H | CH(CH₃)CHBrCH₃ | H | H | OCH₃ | OCH₂CH₂F | N | |
| H | CH(CH₃)CHBrCH₃ | H | H | OCH₃ | OCH₂CHF₂ | N | |
| H | CH(CH₃)CHFCH₃ | H | H | CH₃ | OCH₂CH₂F | N | |
| H | CH(CH₃)CHFCH₃ | H | H | CH₃ | OCH₂CHF₂ | N | |
| H | CH(CH₃)CHFCH₃ | H | H | OCH₃ | OCH₂CH₂F | N | |
| H | CH(CH₃)CHFCH₃ | H | H | OCH₃ | OCH₂CHF₂ | N | |
| H | CH₂CCl₂CH₃ | H | H | CH₃ | OCH₂CH₂F | N | |
| H | CH₂CCl₂CH₃ | H | H | CH₃ | OCH₂CHF₂ | N | |
| H | CH₂CCl₂CH₃ | H | H | OCH₃ | OCH₂CH₂F | N | |
| H | CH₂CCl₂CH₃ | H | H | OCH₃ | OCH₂CHF₂ | N | |
| H | CH₂CH(CH₃)CH₂Cl | H | H | CH₃ | OCH₂CH₂F | N | |
| H | CH₂CH(CH₃)CH₂Cl | H | H | CH₃ | OCH₂CHF₂ | N | |
| H | CH₂CH(CH₃)CH₂Cl | H | H | OCH₃ | OCH₂CH₂F | N | |
| H | CH₂CH(CH₃)CH₂Cl | H | H | OCH₃ | OCH₂CHF₂ | N | |
| H | CH₂CH(CH₃)CH₂Br | H | H | CH₃ | OCH₂CH₂F | N | |
| H | CH₂CH(CH₃)CH₂Br | H | H | CH₃ | OCH₂CHF₂ | N | |
| H | CH₂CH(CH₃)CH₂Br | H | H | OCH₃ | OCH₂CH₂F | N | |
| H | CH₂CH(CH₃)CH₂Br | H | H | OCH₃ | OCH₂CHF₂ | N | |
| H | CH₂CH(CH₃)CH₂F | H | H | CH₃ | OCH₂CH₂F | N | |
| H | CH₂CH(CH₃)CH₂F | H | H | CH₃ | OCH₂CHF₂ | N | |
| H | CH₂CH(CH₃)CH₂F | H | H | OCH₃ | OCH₂CH₂F | N | |
| H | CH₂CH(CH₃)CH₂F | H | H | OCH₃ | OCH₂CHF₂ | N | |
| H | CH₂CF₂Cl | H | H | CH₃ | OCH₂CH₂F | N | |
| H | CH₂CF₂Cl | H | H | CH₃ | OCH₂CHF₂ | N | |
| H | CH₂CF₂Cl | H | H | OCH₃ | OCH₂CH₂F | N | |
| H | CH₂CF₂Cl | H | H | OCH₃ | OCH₂CHF₂ | N | |
| H | CH(CHCl₂)CH₂Cl | H | H | CH₃ | OCH₂CH₂F | N | |
| H | CH(CHCl₂)CH₂Cl | H | H | CH₃ | OCH₂CHF₂ | N | |
| H | CH(CHCl₂)CH₂Cl | H | H | OCH₃ | OCH₂CH₂F | N | |
| H | CH(CHCl₂)CH₂Cl | H | H | OCH₃ | OCH₂CHF₂ | N | |
| H | CH(CHCl₂)CH₂F | H | H | CH₃ | OCH₂CH₂F | N | |
| H | CH(CHCl₂)CH₂F | H | H | CH₃ | OCH₂CHF₂ | N | |
| H | CH(CHCl₂)CH₂F | H | H | OCH₃ | OCH₂CH₂F | N | |
| H | CH(CHCl₂)CH₂F | H | H | OCH₃ | OCH₂CHF₂ | N | |
| H | CH(CH₂Cl)CH₂CH₂Cl | H | H | CH₃ | OCH₂CH₂F | N | |
| H | CH(CH₂Cl)CH₂CH₂Cl | H | H | CH₃ | OCH₂CHF₂ | N | |
| H | CH(CH₂Cl)CH₂CH₂Cl | H | H | OCH₃ | OCH₂CH₂F | N | |
| H | CH(CH₂Cl)CH₂CH₂Cl | H | H | OCH₃ | OCH₂CHF₂ | N | |
| H | CH₂Br | H | H | CH₃ | OCH₂CH₂F | N | |
| H | CH₂Br | H | H | CH₃ | OCH₂CHF₂ | N | |
| H | CH₂Br | H | H | OCH₃ | OCH₂CH₂F | N | |
| H | CH₂Br | H | H | OCH₃ | OCH₂CHF₂ | N | |
| H | CH₂Cl | H | H | CH₃ | OCH₂CH₂F | N | |
| H | CH₂Cl | H | H | CH₃ | OCH₂CHF₂ | N | |
| H | CH₂Cl | H | H | OCH₃ | OCH₂CH₂F | N | |
| H | CH₂Cl | H | H | OCH₃ | OCH₂CHF₂ | N | |
| H | CHCl₂ | H | H | CH₃ | OCH₂CH₂F | N | |
| H | CHCl₂ | H | H | CH₃ | OCH₂CHF₂ | N | |
| H | CHCl₂ | H | H | OCH₃ | OCH₂CH₂F | N | |
| H | CHCl₂ | H | H | OCH₃ | OCH₂CHF₂ | N | |
| H | CCl₃ | H | H | CH₃ | OCH₂CH₂F | N | |
| H | CCl₃ | H | H | CH₃ | OCH₂CHF₂ | N | |
| H | CCl₃ | H | H | OCH₃ | OCH₂CH₂F | N | |
| H | CCl₃ | H | H | OCH₃ | OCH₂CHF₂ | N | |

TABLE IX

General Structure IX

| R₂ | R₇ | R | X | Y | Z | m.p. (°C.) |
|---|---|---|---|---|---|---|
| H | H | H | CH₃ | OCH₂CHF₂ | N | |
| H | H | H | OCH₃ | OCH₂CHF₂ | N | |
| H | H | H | OCH₃ | OCH₂CH₂F | N | |
| H | CH₃ | H | OCH₃ | OCH₂CH₂F | N | |
| H | CH₃ | H | OCH₃ | OCH₂CHF₂ | N | |
| H | CH₃ | H | CH₃ | OCH₂CHF₂ | N | |
| 6-OCH₃ | CH₃ | H | CH₃ | OCH₂CHF₂ | N | |
| H | H | H | CH₃ | OCH₂CH₂F | N | |
| H | CH₃ | F | CH₃ | OCH₂CH₂F | N | |
| H | H | H | OCH₃ | OCH₂CH₂F | CH | |

TABLE IX-continued

General Structure IX

| $R_2$ | $R_7$ | R | X | Y | Z | m.p. (°C.) |
|---|---|---|---|---|---|---|
| H | H | H | $OCH_3$ | $OCH_2CHF_2$ | CH | |

TABLE X

General Structure X

| $R_2$ | $R_7$ | R | X | Y | Z | m.p. (°C.) |
|---|---|---|---|---|---|---|
| H | H | H | $CH_3$ | $OCH_2CHF_2$ | N | |
| H | H | H | $OCH_3$ | $OCH_2CHF_2$ | N | |
| H | H | H | $OCH_3$ | $OCH_2CH_2F$ | N | |
| H | $CH_3$ | H | $OCH_3$ | $OCH_2CH_2F$ | N | |
| H | $CH_3$ | H | $OCH_3$ | $OCH_2CHF_2$ | N | |
| H | $CH_3$ | H | $CH_3$ | $OCH_2CHF_2$ | N | |
| 6-$OCH_3$ | $CH_3$ | H | $CH_3$ | $OCH_2CHF_2$ | N | |
| H | H | H | $CH_3$ | $OCH_2CH_2F$ | N | |
| H | $CH_3$ | H | $CH_3$ | $OCH_2CH_2F$ | N | |
| H | H | H | $OCH_3$ | $OCH_2CH_2F$ | CH | |
| H | H | H | $CH_3$ | $OCH_2CHF_2$ | CH | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1–99% by weight of active ingredient(s) and at least one of (a) about 0.1–20% surfactant(s) and (b) about 5–99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., *Handbook of Insecticide Dust Diluents and Carriers,* 2nd Edition, Dorland Books, Caldwell, NJ. The more absorptive diluents are preferred for wettable powders and the denser ones for dusts. Typical liquid diluents and solvents are described in Marsden, *Solvents Guide,* 2nd Edition, Interscience, New York 1950. Solubility under 0.1% is preferred for suspension concentrates; solution concentrates are preferably stable against phase separation at 0° C. *McCutcheon's Detergents and Emulsifiers Annual,* Allured Publishing Corp., Ridgewood, NJ, as well as Sisely and Wood, *Encyclopedia of Surface Active Agents,* Chemical Publishing Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration" *Chemical Engineering,* Dec. 4, 1967, pages 147ff and *Perry's Chemical Engineer's Handbook,* 4th Edition, McGraw-Hill, New York 1963, pages 8–59ff.

For further information regarding the art of formulation, see for example: H. M. Loux, U.S. Pat. No. 3,235,361, issued Feb. 15, 1966, Col. 6, lines 16 through Col. 7, line 19, and Examples 10 through 41; R. W. Luckenbaugh, U.S. Pat. No. 3,309,192, issued Mar. 14, 1967, Col. 5, lines 43 through Col. 7, line 62, and Examples 8, 12, 15, 39, 41, 52, 53, 58, 132, 138–140, 162–164, 166, 167, 169–182; H. Gysin and E. Knusli, U.S. Pat. No. 2,891,855 issued June 23, 1959, Col. 3, lines 66 through Col. 5, line 17 and Examples 1–4; G. C. Klingman, *Weed Control As a Science,* John Wiley & Sons, Inc., New York 1961, pages 81–96; and J. D. Fryer and S. A. Evans, *Weed Control Handbook,* 5th Edition, Blackwell Scientific Publications, Oxford, 1968, pages 101–103.

EXAMPLE 4

Wettable Powder

| | |
|---|---|
| 2-ethoxy-N—[[4-methoxy-6-(2,2,2-trifluoroethoxy)-1,3,5-triazin-2-yl]aminocarbonyl]benzenesulfonamide | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE 5

Wettable Powder

| | |
|---|---|
| N—[[4-methoxy-6-(2,2,2-trifluoroethoxy)-1,3,5 triazin-2-yl]aminocarbonyl]-2-propoxybenzenesulfonamide | 50% |
| sodium alkylnaphthalenesulfonate | 2% |
| low viscosity methyl cellulose | 2% |
| diatomaceous earth | 46% |

The ingredients are blended, coarsely hammer milled and the air milled to produce particles of active essentially all below 10 microns in diameter. The product is reblended before packaging.

EXAMPLE 6

Wettable Powder

| | |
|---|---:|
| 2-ethoxy-N—[[4-methoxy-6-(2,2,2-trifluoroethoxy)-1,3,5-triazin-2-yl]aminocarbonyl]benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammermilled until all the solids are essentially under 50 microns in diameter, and then reblended before packaging.

EXAMPLE 7

Wettable Powder

| | |
|---|---:|
| N—[[4-methoxy-6-(2,2,2-trifluoroethoxy)-1,3,5-triazin-2-yl]aminocarbonyl]-2-propoxybenzenesulfonamide | 65% |
| dodecylphenol polyethylene glycol ether | 2% |
| sodium ligninsulfonate | 4% |
| sodium silicoaluminate | 6% |
| montmorillonite (calcined) | 23% |

The ingredients are thoroughly blended. The liquid surfactant is added by spraying upon the solid ingredients in the blender. After grinding in a hammermill to produce particles essentially all below 100 microns, the material is reblended and sifted through a U.S.S. No. 50 sieve (0.3 mm opening) and packaged.

EXAMPLE 8

High Strength Concentrate

| | |
|---|---:|
| 2-ethoxy-N—[[4-methoxy-6-(2,2,2-trifluoroethoxy)-1,3,5-triazin-2-yl]aminocarbonyl]benzenesulfonamide | 98.5% |
| silica aerogel | 0.5% |
| synthetic amorphous fine silica | 1.0% |

The ingredients are blended and ground in a hammermill to produce a high strength concentrate essentially all passing a U.S.S. No. 50 sieve (0.3 mm opening). This material may then be formulated in a variety of ways.

EXAMPLE 9

Aqueous Suspension

| | |
|---|---:|
| N—[[4-methoxy-6-(2,2,2-trifluoroethoxy)-1,3,5-triazin-2-yl]aminocarbonyl]-2-propoxybenzenesulfonamide | 25% |
| hydrated attapulgite | 3% |
| crude calcium ligninsulfonate | 10% |
| sodium dihydrogen phosphapte | 0.5% |
| water | 61.5% |

The ingredients are ground together in a ball or roller mill until the solid particles have been reduced to diameters under 10 microns.

EXAMPLE 10

Oil Suspension

| | |
|---|---:|
| 2-ethoxy-N—[[4-methoxy-6-(2,2,2-trifluoroethoxy)-1,3,5-triazin-2-yl]aminocarbonyl]benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 11

Granule

| | |
|---|---:|
| 2-ethoxy-N—[[4-methoxy-6-(2,2,2-trifluoroethoxy)-1,3,5-triazin-2-yl]aminocarbonyl]benzenesulfonamide | 80% |
| Wetting Agent | 1% |
| Crude Ligninsulfonate salt (containing 5–20% of the natural sugars) | 10% |
| Attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the moisture in the material is reduced to the desired level, generally less than 1%. The material is then discharged, screened to the desired size range, generally 14–100 mesh (140–149 microns), and packaged for use.

EXAMPLE 12

Extruded Pellet

| | |
|---|---:|
| N—[[4-methoxy-6-(2,2,2-trifluoroethoxy)-1,3,5-triazin-2-yl]aminocarbonyl]-2-propoxybenzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammermilled and then moistened with about 12% water. The mixture is extruded as cylinders about 3 mm diameter which are cut to produce pellets about 3 mm long. These may be used directly after drying, or the dried pellets may be crushed to pass a U.S.S. No 20 sieve (0.54 mm openings). The granules held on a U.S.S. No. 40 sieve (0.42 mm openings) may be packaged for use and the fines recycled.

UTILITY

Test results indicate that the compounds of the present invention are active herbicides. They should have utility for broad spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful for the selective pre- or post-emergence weed control in corn.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.002–5 kg/ha, the lower rates being suggested for use on lighter soils and/or those having a low organic matter content, for selective weed control or for situations where only short-term persistence is required.

The compounds of the invention may be used in combination with any other commercial herbicide; examples of which are those of the triazine, triazole, uracil, urea, amide, diphenylether, carbamate, and bipyridylium types. They may also be used in combination with mefluidide.

| Compound | Structure | m.p. (°C.) |
|---|---|---|
| 1 | phenyl(OC$_2$H$_5$)-SO$_2$NHCNH-pyrimidine(OCH$_3$)(OCH$_2$CF$_3$) | 180–181 (d) |
| 2 | phenyl(OCH$_2$CH$_2$CH$_3$)-SO$_2$NHCNH-pyrimidine(OCH$_3$)(OCH$_2$CF$_3$) | 161–163 (d) |
| 3 | phenyl(OCH$_2$CH$_2$CH$_3$)-SO$_2$NHCNH-pyrimidine(CH$_3$)(OCH$_2$CF$_3$) | 121–126 (d) |
| 4 | phenyl(OCH$_2$CH$_2$CH$_3$)-SO$_2$NHCNH-pyrimidine(OCH$_3$)(OCH$_2$CH$_2$F) | 120–124 (d) |
| 5 | phenyl(OC$_2$H$_5$)-SO$_2$NHCNH-pyrimidine(CH$_3$)(OCH$_2$CF$_3$) | 132–137 |
| 6 | phenyl(OC$_2$H$_5$)-SO$_2$NHCNH-pyrimidine(OCH$_3$)(OCH$_2$CH$_2$F) | 94–102 112 (d) |
| 7 | naphthyl(SCH$_3$)-SO$_2$NHCNH-pyrimidine(OCH$_3$)(OCH$_2$CF$_3$) | 115–118 (d) |
| 8 | naphthyl(Cl)-SO$_2$NHCNH-pyrimidine(OCH$_3$)(OCH$_2$CF$_3$) | 193–197 (d) |
| 9 | phenyl(OC$_2$H$_5$)-SO$_2$NHCNH-pyrimidine(CH$_3$)(OCH$_2$CH$_2$F) | 198–202 |
| 10 | phenyl(OCH$_2$CH$_2$CH$_3$)-SO$_2$NHCNH-pyrimidine(CH$_3$)(OCH$_2$CH$_2$F) | 176–179 |
| 11 | phenyl(OC$_2$H$_5$)-SO$_2$NHCNH-pyrimidine(OCH$_3$)(OCH$_2$CF$_3$) | 165–168 |
| 12 | phenyl(OCH$_2$CH$_2$CH$_3$)-SO$_2$NHCNH-pyrimidine(OCH$_3$)(OCH$_2$CF$_3$) | 168–170 |
| 13 | phenyl(SO$_2$N(CH$_3$)$_2$)-SO$_2$NHCNH-pyrimidine(OCH$_3$)(OCH$_2$CH$_2$F) | 152–156 |

TEST A

Seeds of crabgrass (Digitaria spp.), barnyardgrass (Echinochloa crusgalli), wild oats (Avena fatua), sicklepod (Cassia obtusifolia), morningglory (Ipomoea spp.), cocklebur (Xanthium pensylvanicum), sorghum, corn, soybean, cotton, sugar beet, rice, wheat, and purple nutsedge (Cyperus rotundus) tubers were planted and treated preemergence with the test chemicals dissolved in a nonphytotoxic solvent. At the same time, these crop and weed species were treated with a soil/foliage application. At the time of treatment, the plants ranged in height from 2-18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete control. The accompanying descriptive symbols have the following meanings:
C=chlorosis/necrosis
E=emergence inhibition
G=growth retardation
H=formative effect The herbicidal properties of the subject compounds were discovered in a number of greenhouse tests. The test procedures and results follow:

TABLE A

| Rate kg/ha | Cmpd. 1 0.05 | Cmpd. 2 0.05 | Cmpd. 3 0.05 | Cmpd. 4 0.05 | Cmpd. 5 0.05 | Cmpd. 6 0.05 | Cmpd. 7 0.05 |
|---|---|---|---|---|---|---|---|
| POSTEMERGENCE | | | | | | | |
| Morningglory | 9C | 9C | 5C,8H | 10C | 9C | 10C | 0 |
| Cocklebur | 10C | 10C | 10C | 10C | 6C,9G | 2C,9G | 2C,5G |
| Sicklepod | 5C,9G | 5C,9G | 4C,9G | 9C | 9C | 9C | 2C |
| Nutsedge | 4C,9G | 4C,8G | 5G | 4C,9G | 6C,9G | 9C | 0 |
| Crabgrass | 2C,5G | 2G | 0 | 5G | 5G | 5G | 2G |
| Barnyardgrass | 3C,8H | 0 | 2C,2H | 3C,9H | 5C,9H | 3C,9H | 3H |
| Wild Oats | 8G | 0 | 0 | 5G | 6G | 2C,9G | 0 |
| Wheat | 4G | 0 | 0 | 3G | 0 | 8G | 0 |
| Corn | 4G | 1C | 0 | 1H | 6G | 3G | 0 |
| Soybean | 4C,9G | 9C | 5C,9G | 9C | 5C,9G | 9C | 2C,3G |
| Rice | 5C,9G | 4C,7G | 3C,8G | 2C,9G | 9C | 9C | 2C |
| Sorghum | 2C,9G | 1C,3G | 3C,5G | 2C,9H | 2C,9H | 3C,9H | 2G |
| Sugar beet | 5C,9G | 9C | 9C | 9C | 10C | 10C | 3C,6G |
| Cotton | 9C | 9C | 5C,9G | 5C,9G | 9C | 9C | 0 |
| PREEMERGENCE | | | | | | | |
| Morningglory | 4C,9G | 9G | 9G | 9C | 9G | 9G | 0 |
| Cocklebur | 9H | 9H | — | — | 8H | 8H | 4G |
| Sicklepod | 9G | 6G | 9G | 10C | 9G | 9C | — |
| Nutsedge | 10E | 8G | 4C,9G | 3C,8G | 2C,8G | 3C,9G | 0 |
| Crabgrass | 0 | 3G | 3G | 5G | 2G | 1C | 3G |
| Barnyardgrass | 3C,6G | 1G,3G | 2G | 5G | 7H | 9H | 3G |
| Wild Oats | 2C,8G | 0 | 2C,6G | 2C,6G | 5G | 6C,9G | 0 |
| Wheat | 0 | 0 | 0 | 0 | 0 | 6G | 5C |
| Corn | 1C,5G | 2C | 5G | 5G | 7G | 5G | 3G |
| Soybean | 9H | 8H | 9H | 9H | 8H | 9H | 0 |
| Rice | 10E | 6G | 3C,8H | 3C,9H | 9H | 10E | 2C,5G |
| Sorghum | 4C,9H | 5G | 2C,8G | 3C,9G | 3C,8H | 5C,9H | 2C,6G |
| Sugar beet | 10E | 10E | 10E | 10E | 9C | 9C | 6G |
| Cotton | 9G | 9G | 9G | 9G | 9G | 9G | 2G |

| Rate kg/ha | Cmpd. 8 0.05 | Cmpd. 9 0.05 | Cmpd. 10 0.05 | Cmpd. 11 0.05 | Cmpd. 12 0.05 | Cmpd. 13 0.05 |
|---|---|---|---|---|---|---|
| POSTEMERGENCE | | | | | | |
| Morningglory | 5C,9G | 2C,7H | 2C,4G | 2C,8G | 3C,7H | 10C |
| Cocklebur | 9C | 3G | 2C,2G | 1C | 3G | 10C |
| Sicklepod | 2C,3G | 4C,9H | 2C,4G | 2C,3H | 2C,6G | 5C,9G |
| Nutsedge | 2C,8G | 3C,8G | 5G | 4C,8G | 2C,4G | 5C,9G |
| Crabgrass | 3C,5G | 2C,8G | 3G | 2G | 0 | 4C,8G |
| Barnyardgrass | 2C,3H | 4C,9H | 3C,9H | 1H | 0 | 9C |
| Wild Oats | 0 | 4C,7G | 2C,3G | 0 | 0 | 5C,9G |
| Wheat | 0 | 2C,8G | 2C,3G | 0 | 0 | 9C |
| Corn | 0 | 3C,9H | 1G | 1H | 0 | 5U,9C |
| Soybean | 4C,9G | 3C,9H | 4C,9G | 2C,5H | 3C,6H | 5C,9G |
| Rice | 1G | 5C,9G | 8G | 6G | 0 | 6C,9G |
| Sorghum | 1G | 3C,9G | 2C,9G | 5G | 2G | 4U,9G |
| Sugar beet | 5C,9G | 4C,9G | 3C,5G | 2C,6G | 8G | 9C |
| Cotton | 4C,8H | 9C | 3C,8G | 8G | 4C,9G | 9C |
| PREEMERGENCE | | | | | | |
| Morningglory | 8G | 7G | 2G | 9G | 7G | 9G |
| Cocklebur | 8H | — | 8H | 7H | 0 | 9H |
| Sicklepod | 2C,8G | 5C,9G | 2C | 8G | 2H | 3C,9G |
| Nutsedge | 3C,5G | 3C,7G | 4G | 5G | 0 | 4G |
| Crabgrass | 1C | 6G | 2G | 3G | 0 | 2C,5G |
| Barnyardgrass | 2C,2H | 5C,9H | 2C,8H | 3C,9H | 6G | 3C,9H |
| Wild Oats | 2C,2G | 6C,9G | 8G | 2C,5G | 0 | 3C,8H |
| Wheat | 4G | 4C,9H | 9H | 5G | 0 | 7C,9H |
| Corn | 3C,6G | 3C,9H | 1C,6G | 5G | 3G | 3C,9H |
| Soybean | 1C | 3C,7G | 2C,2H | 2C,2H | 2G | 9H |
| Rice | 3C,7G | 3C,8H | 2C,8G | 5G | 0 | 10E |
| Sorghum | 3C,6G | 3C,9H | 2C,9G | 2C,8G | 7G | 5C,9H |
| Sugar beet | 9C | 4C,9G | 8G | 8G | 7H | 5C,9G |
| Cotton | 7G | 2C,9G | 8G | 8G | 2G | 2C,9G |

TEST B
Postemergence

Two round pans (25 cm diameter by 12.5 cm deep) were filled with Woodstown sandy loam soil. One pan was planted with blackgrass (*Alopecurus myosuroides*), sugar beets, nutsedge (*Cyperus rotundus*) tubers, crabgrass (*Digitaria sanguinalis*), sicklepod (*Cassia obtusifolia*), teaweed (*Sida spinosa*), jimsonweed (*Datura stramonium*), velvetleaf (*Abutilon theophrasti*), and giant foxtail (*Setaria faberii*). The other pan was planted with wheat, cotton, rice, corn, soybean, wild oats (*Avena fatua*), cocklebur (*Xanthium pensylvanicum*), morningglory (*Ipomoea hederacea*), johnsongrass (*Sorghum halepense*) and barnyard grass (*Echinochloa crusgalli*). The plants were grown for approximately fourteen days, then sprayed postemergence with the chemicals dissolved in a nonphytotoxic solvent.

Preemergence

Two round pans (25 cm diameter by 12.5 cm deep) were filled with Woodstown sandy loam soil. One pan was planted with blackgrass (*Alopecurus myosuroides*), sugar beets, nutsedge, crabgrass, sicklepod, teaweed, jimsonweed, velvetleaf, and giant foxtail. The other pan was planted with wheat, cotton, rice, corn, soybeans, wild oats, cocklebur, morningglory, johnsongrass and barnyardgrass. The two pans were sprayed preemergence with the chemicals dissolved in a nonphytotoxic solvent.

Treated plants and controls were maintained in the greenhouse for 28 days, then all treated plants were compared to controls and visually rated for plant response as described for Test A.

Response ratings are contained in Table B. The data show that both test compounds have utility for selective pre- and postemergence weed control in corn.

Three 25-cm diameter plastic pots were filled with a light soil. One pot was planted to short rows of corn, soybeans and cotton, planting depth 2.5 cm. The other two pots were plants to the following weed species, 8 or 9 species per pot: crabgrass (Digitaria sp.), johnsongrass (*Sorghum halepense*), barnyardgrass (*Echinochloa crusgalli*), nutsedge (*Cyperus rotundus*), giant foxtail (*Setaria faberi*), green foxtail (*Setaria viridis*), cocklebur (*Xanthium pensylvanicum*), morningglory (*Ipomoea hederacea*), teaweed (*Sida spinosa*), sicklepod (*Cassia obtusifolia*), jimsonweed (*Datura stramonium*), velvetleaf (*Abutilon theophrasti*), bindweed (*Convolvulus arvensis*), coffeeweed (*Sesbania exaltata*), lambsquarters (*Chenopodium album*), pigweed (*Amaranthus retroflexus*) and purslane (*Portulaca oleracea*). All of the foregoing weed species were planted at a depth of 0.5-1.0 cm except for cocklebur and nutsedge which were planted at a depth of 2.5 cm. The plantings were treated preemergence with the test chemicals dissolved in a nonphytotoxic solvent. At the same time, the same crops and weed species, from plantings made 10-21 days previously, were treated with soil/foliage applications. Treated plants and controls were maintained in a greenhouse for 3-4 weeks after which all species were compared to controls and visually rated for response to treatment utilizing the same rating system as described for Test A. The data for three tests for Compound 1 and two tests for Compound 2 are summarized in Table C.

It will be seen that both compounds can be used for selective weed control in corn, either applied pre- or postemergence.

TABLE B

| | Compound 1 | | | | Compound 2 | | | | Compound 8 | | | Compound 10 | | Compound 13 | | | |
|---|---|---|---|---|---|---|---|---|---|---|---|---|---|---|---|---|---|
| Rate g/ha | 62 | 16 | 4 | 1 | 62 | 16 | 4 | 1 | 250 | 62 | 16 | 250 | 62 | 62 | 16 | 4 | 1 |
| | | | | | | POSTEMERGENCE | | | | | | | | | | | |
| Corn | 3G | 0 | 0 | 0 | 0 | 0 | 0 | 0 | 0 | 0 | 0 | 4G | 0 | 10G | 10C | 9G | 5G |
| Wheat | 3G | 0 | 0 | 0 | 0 | 0 | 0 | 0 | 0 | 0 | 0 | 4G | 0 | 10C | 7G | 0 | 0 |
| Rice | 10G | 9G | 3G | 0 | 2G | 0 | 0 | 0 | 4G | 2G | 0 | 4G | 3G | 10C | 10G | 8G | 4G |
| Soybean | 10G | 10G | 9G | 8G | 9G | 9G | 6G | 2G | 10G | 9G | 7G | 8G | 5G | 10G | 10G | 9G | 6G |
| Cotton | 10C | 8G | 4G | 2G | 9G | 5G | 2G | 0 | 4G | 3G | 0 | 7G | 3G | 10G | 8G | 6G | 3G |
| Sugar beet | 10C | 10C | 10C | 8G | 9G | 9G | 7G | 4G | 10G | 10G | 4G | 5G | 3G | 10C | 8G | 5G | 4G |
| Crabgrass | 0 | 0 | 0 | 0 | 3G | 0 | 0 | 0 | 3G | 0 | 0 | 0 | 0 | 5G | 3G | 0 | 0 |
| Johnsongrass | 10G | 5G | 3G | 0 | 0 | 0 | 0 | 0 | 0 | 0 | 0 | 6G | 0 | 10C | 9G | 4G | 3G |
| Blackgrass | 10C | 9G | 3G | 0 | 0 | 0 | 0 | 0 | 4G | 0 | 0 | 7G | 0 | 10C | 6G | 0 | 0 |
| Barnyardgrass | 5G | 2G | 0 | 0 | 0 | 0 | 0 | 0 | 0 | 0 | 0 | 7G | 4G | 10C | 9G | 5G | 0 |
| Nutsedge | 10C | 10C | 4G | 0 | 0 | 0 | 0 | 0 | 7G | 4G | 0 | 0 | 0 | 3G | 0 | 0 | 0 |
| Giant foxtail | 3G | 0 | 0 | 0 | 0 | 0 | 0 | 0 | 0 | 0 | 0 | 4G | 0 | 10C | 3G | 0 | 0 |
| Wild Oats | 5G | 0 | 0 | 0 | 0 | 0 | 0 | 0 | 0 | 0 | 0 | 3G | 0 | 10C | 5G | 0 | 0 |
| Cocklebur | 10C | 10G | 7G | 3G | 10C | 8G | 6G | 3G | 10G | 9G | 7G | 0 | 0 | 10G | 7G | 4G | 0 |
| Morningglory | 10G | 10G | 9G | 5G | 9G | 7G | 2G | 0 | 10G | 8G | 6G | 3G | 0 | 10G | 7G | 3G | 0 |
| Teaweed | 9G | 5G | 0 | 0 | 4G | 0 | 0 | 0 | 0 | 0 | 0 | 4G | 0 | 6G | 2G | 0 | 0 |
| Sicklepod | 10G | 9G | 4G | 0 | 4G | 2G | 0 | 0 | 4G | 0 | 0 | 3G | 0 | 6G | 4G | 0 | 0 |
| Jimsonweed | 10C | 7G | 5G | 0 | 7G | 7G | 0 | 0 | 4G | 0 | 0 | 7G | 5G | 6G | 5G | 0 | 0 |
| Velvetleaf | 10C | 10C | 8G | 2G | 9G | 7G | 4G | 0 | 9G | 7G | 3G | 9G | 7G | 10G | 5G | 0 | 0 |
| Rate g/ha | 250 | 62 | 16 | 4 | 250 | 62 | 16 | 4 | 250 | 62 | 16 | 250 | 62 | 250 | 62 | 16 | 4 |
| | | | | | | PREEMERGENCE | | | | | | | | | | | |
| Corn | 2G | 0 | 0 | 0 | 2G | 0 | 0 | 0 | 2G | 0 | 0 | 4G | 2G | 10E | 10G | 6G | 0 |
| Wheat | 0 | 0 | 0 | 0 | 2G | 0 | 0 | 0 | 0 | 0 | 0 | 7G | 4G | 7G | 2G | 0 | 0 |
| Rice | 10E | 10E | 9G | 5G | 9G | 5G | 2G | 0 | 7G | 5G | 2G | 10G | 6G | 10E | 10E | 10G | 6G |
| Soybean | 10G | 9G | 7G | 2G | 8G | 4G | 0 | 0 | 2G | 0 | 0 | 5G | 2G | 10G | 9G | 4G | 0 |
| Cotton | 10G | 10G | 6G | 0 | 9G | 4G | 0 | 0 | 3G | 0 | 0 | 7G | 0 | 8G | 6G | 0 | 0 |
| Sugar beet | 10G | 10E | 9G | 5G | 10G | 8G | 3G | 0 | 10G | 7G | 4G | 9G | 7G | 10G | 10G | 10G | 3G |
| Crabgrass | 0 | 0 | 0 | 0 | 0 | 0 | 0 | 0 | 3G | 0 | 0 | 2G | 0 | 10G | 7G | 4G | 2G |
| Johnsongrass | 10G | 9G | 4G | 0 | 7G | 3G | 2G | 0 | 2G | 0 | 0 | 7G | 0 | 10C | 10C | 9G | 4G |
| Blackgrass | 10G | 9G | 8G | 2G | 9G | 5G | 4G | 0 | 7G | 5G | 2G | 10G | 7G | 10E | 9G | 7G | 2G |
| Barnyardgrass | 6G | 6G | 2G | 0 | 3G | 0 | 0 | 0 | 4G | 0 | 0 | 6G | 0 | 10G | 10G | 7G | 3G |
| Nutsedge | 10E | 10E | 7G | 3G | 9G | 5G | 3G | 2G | 9G | 3G | 0 | 4G | 0 | 10E | 3G | 0 | 0 |
| Giant foxtail | — | — | — | — | — | — | — | — | — | — | 0 | 8G | 5G | 10E | 10G | 9G | 4G |
| Wild Oats | 7G | 5G | 0 | 0 | 3G | 0 | 0 | 0 | 0 | 0 | 0 | 7G | 6G | 8G | 4G | 2G | 0 |
| Cocklebur | 10G | 10G | 8G | 3G | 10G | 9G | 6G | 2G | 8G | 0 | 0 | 0 | 0 | 10G | 7G | 3G | 0 |
| Morningglory | 10G | 10G | 7G | 3G | 9G | 6G | 4G | 2G | 6G | 0 | 0 | 0 | 0 | 10G | 7G | 2G | 0 |
| Teaweed | 10G | 9G | 6G | 3G | 9G | 4G | 0 | 0 | 9G | 5G | 3G | 3G | 0 | 8G | 3G | 0 | 0 |
| Sicklepod | 10E | 10G | 6G | 4G | 9G | 4G | 0 | 0 | 5G | 0 | 0 | 8G | 0 | 7G | 3G | 0 | 0 |
| Jimsonweed | 10G | 10G | 9G | 3G | 9G | 4G | 0 | 0 | 7G | 3G | 0 | 8G | 4G | 9G | 8G | 4G | 0 |
| Velvetleaf | 10G | 10G | 9G | 3G | 9G | 5G | 0 | 0 | 7G | 2G | 0 | 6G | 2G | 10G | 5G | 2G | 0 |

TEST C

TABLE C

Compound 1

POSTEMERGENCE

| Rate g/ha | 16 | 31 | 62 | 125 | 250 | 4 | 16 | 62 | 250 | 1000 | 16 | 31 | 62 | 125 | 250 |
|---|---|---|---|---|---|---|---|---|---|---|---|---|---|---|---|
| Corn | 0 | 0 | 0 | 0 | 0 | 0 | 0 | 0 | 3G | 5G | 0 | 0 | 0 | 0 | 0 |
| Cotton | 10C | 10C | 10C | 10C | 10C | 5G | 10C | 10C | 10C | 10C | 9G | 10C | 10C | 10C | 10C |
| Soybean | 10C | 10C | 10C | 10C | 10C | 10C | 10C | 10C | 10C | 10C | 10C | 10C | 10C | 10C | 10C |
| Green foxtail | 0 | 0 | 0 | 0 | 0 | 0 | 0 | 0 | 2G | 5G | 0 | 0 | 0 | 0 | 3G |
| Giant foxtail | 0 | 0 | 0 | 2G | 3G | 0 | 0 | 0 | 3G | 7G | 0 | 0 | 0 | 0 | 3G |
| Barnyardgrass | 0 | 0 | 0 | 0 | 4G | 0 | 0 | 0 | 3G | 10C | 0 | 0 | 0 | 0 | 6G |
| Johnsongrass | 0 | 3G | 6G | 8G | 10C | 0 | 2G | 5G | 8G | 10C | 0 | 0 | 0 | 3G | 9G |
| Crabgrass | 0 | 0 | 0 | 0 | 0 | 0 | 0 | 0 | 0 | 7G | 0 | 0 | 0 | 0 | 0 |
| Nutsedge | — | 7G | 8G | 9G | 10C | 5G | 10C | 10C | 10C | 10C | — | — | — | — | — |
| Velvetleaf | 10C | 10C | 10C | 10C | 10C | 5G | 9G | 10C | 10C | 10C | 10C | 10C | 10C | 10C | 10C |
| Sicklepod | 6G | 9G | 8G | 10G | 10C | 0 | 6G | 9G | 9G | 10C | 8G | 9G | 9G | 9G | 9G |
| Lambsquarter | 10C | 10C | 5G | 8G | 10C | 4G | 8G | 9G | 9G | 10C | 10C | 10C | — | 10C | 10C |
| Pigweed | 10C | 10C | 10C | 10C | 10C | 5G | 8G | 9G | 8G | 10C | 10C | 10C | 10C | 10C | 10C |
| Bindweed | 9G | 10C | 10C | 10C | 10C | 5G | 7G | 8G | 10C | 10C | 8G | 9G | 9G | 10C | 10C |
| Jimsonweed | 8G | 8G | 9G | 10C | 10C | 6G | 8G | 10C | 8G | 9G | 8G | 10C | 10C | 10C | 10C |
| Prickly sida | 6G | 10C | 9G | 10C | 10C | 4G | 7G | 9G | 10C | 10C | 8G | 10C | 10C | 10C | 10C |
| Sesbania | 10C | 10C | 10C | 10C | 10C | 9G | 8G | 10C | 10C | 10C | 7G | 10C | 10C | 10C | 10C |
| Purslane | 10G | 10G | 10C | 10C | 10C | 8G | 9G | 10G | 10C | 10C | 8G | 10C | 10C | 10C | 10C |
| Morningglory | 10C | 10C | 10C | 10C | 10C | 8G | 9G | 10C | 10C | 10C | 8G | 10C | 10C | 10C | 10C |
| Cocklebur | 10C | 10C | 10C | 10C | 10C | 9G | 8G | 10C | 10C | 10C | 10C | 10C | 10C | 10C | 10C |

Compound 2

POSTEMERGENCE

| Rate g/ha | 62 | 125 | 250 | 500 | 1000 |
|---|---|---|---|---|---|
| Corn | 7G | 9G | 10C | 10C | 10C |
| Cotton | 8G | 9G | 10C | 10C | 10C |
| Soybean | 10C | 10C | 10C | 10C | 10C |
| Green foxtail | 0 | 0 | 0 | 0 | 2G |
| Giant foxtail | 0 | 0 | 0 | 3G | 6G |
| Barnyardgrass | 0 | 3G | 6G | 2G | 6G |
| Johnsongrass | 0 | 3G | 9G | 7G | 7G |
| Crabgrass | 0 | 0 | 0 | 0 | 0 |
| Nutsedge | 9G | 9G | 9G | 7G | 9G |
| Velvetleaf | 7G | 8G | 10C | 10C | 10C |
| Sicklepod | — | — | — | — | — |
| Lambsquarter | 8G | 10C | 10C | 10C | 10C |
| Pigweed | 8G | 9G | 9G | 9G | 10C |
| Bindweed | 8G | 8G | 8G | 10C | 10C |
| Jimsonweed | 7G | 8G | 9G | 10C | 10C |
| Prickly sida | 8G | 10C | 10C | 10C | 10C |
| Sesbania | 10C | 10C | 10C | 10C | 10C |
| Purslane | 10C | 10C | 10C | 10C | 10C |
| Morningglory | 8G | 10C | 10C | 10C | 10C |
| Cocklebur | 10C | 10C | 10C | 10C | 10C |

Compound 1

PREEMERGENCE

| Rate g/ha | 8 | 16 | 31 | 62 | 125 | 250 |
|---|---|---|---|---|---|---|
| Corn | 0 | 0 | 0 | 0 | 3G | 5G |
| Cotton | 2G | 5G | 6G | 9G | 10G | 10G |
| Soybean | 2G | 5G | 5G | 10G | 8G | 10G |
| Green foxtail | 0 | 0 | 0 | 0 | 2G | 6G |
| Giant foxtail | 0 | 0 | 0 | 2G | 6G | 6G |
| Barnyardgrass | 0 | 0 | 0 | 0 | 5G | 9G |
| Johnsongrass | 0 | 0 | 3G | 6G | 9G | 10G |
| Crabgrass | 0 | 0 | 0 | 0 | 2G | 6G |
| Nutsedge | 0 | 7G | 9G | 10G | 10E | 10E |
| Velvetleaf | 8G | 8G | 10G | 10G | 10G | 10G |
| Sicklepod | 7G | 8G | 8G | 10G | 10G | 10G |
| Lambsquarter | 5G | 8G | 8G | 10G | 10E | 10E |
| Pigweed | 7G | 8G | 10G | 10G | 10G | 10G |
| Bindweed | 7G | 10G | 10G | 10G | 10G | 10G |
| Jimsonweed | 5G | 9G | 9G | 9G | 10G | 10G |
| Prickly sida | 6G | 9G | 7G | 7G | 9G | 10G |
| Sesbania | 0 | 2G | 4G | 9G | 10G | 8G |
| Purslane | 4G | 3G | 9G | 9G | 9G | 10G |
| Morningglory | 3G | 7G | 9G | 9G | 10G | 10G |
| Cocklebur | 2G | 4G | 9G | 9G | 10G | 10G |

Compound 2

PREEMERGENCE

| Rate g/ha | 31 | 62 | 125 | 250 | 500 |
|---|---|---|---|---|---|
| Corn | 0 | 0 | 3G | 6G | 7G |
| Cotton | 0 | 3G | 10G | 10G | 9G |
| Soybean | 3G | 0 | 6G | 8G | 9G |
| Green foxtail | 0 | 0 | 0 | 0 | 0 |
| Giant foxtail | 0 | 0 | 0 | 0 | 2G |
| Barnyardgrass | 0 | 0 | 5G | 5G | 4G |
| Johnsongrass | 0 | 6G | 6G | 8G | 7G |
| Crabgrass | 2G | 0 | 4G | 0 | 0 |
| Nutsedge | 0 | 10E | 9G | 10E | 10E |
| Velvetleaf | 0 | 10E | 6G | 8G | 9G |
| Sicklepod | 0 | 10E | 3G | 7G | 9G |
| Lambsquarter | 0 | 10G | 5G | 5G | 9G |
| Pigweed | 0 | 10G | 8G | 8G | 10G |
| Bindweed | 0 | 10G | 8G | 10G | 10G |
| Jimsonweed | 4G | 10E | 2G | 7G | 9G |
| Prickly sida | 0 | 10G | 2G | 6G | 9G |
| Sesbania | 0 | 10G | 0 | 4G | 7G |
| Purslane | 5G | 10G | 8G | 10G | 10G |
| Morningglory | 0 | 10G | 4G | 8G | 9G |
| Cocklebur | 5G | 10G | 9G | 10G | 10G |

TEST D

This test was conducted utilizing 25 cm and 12.5 cm diameter pots filled with a light soil. The large size pots were planted to either corn or soybeans, 5-8 plants per pot. The small pots were planted to the following weed species, one species per pot: morningglory (*Ipomoea hederacea* var. *hederacea*), velvetleaf (*Abutilon theophrasti*), cocklebur (*Xanthium pensylvanicum*), pigweed (*Amaranthus retroflexus*), giant foxtail (Setaria faberi), johnsongrass (*Sorghum halepense*), crabgrass (Digitaria sp.) and barnyardgrass (*Echinochloa crusgalli*). The plants were treated preemergence with the test chemical dissolved in a nonphytotoxic solvent. At the same time, the same crops and weed species, from plantings made 10-22 days previously, were treated with soil/foliage applications. There were three replications of each treatment. Response data were collected approximately 17 days after treatment for the postemergence phase of the test and approximately 27 days after treatment for the preemergence phase. The weed species were visually rated for injury. The crop plantings contained an equal number of plants per pot for each crop. At the time of rating, total fresh weights per pot were determined of the above-ground portions of the crop plants. Growth since treatment was then calculated and expressed as a percentage of untreated controls. The response data were averaged for the three replications and are shown in Table D.

Compound No. 1 controlled several weed species at rates of application which were noninjurious to corn.

TABLE D

| | Compound 1 % injury/% control | | | | | |
|---|---|---|---|---|---|---|
| Rate g/ha | 250 | 125 | 62 | 31 | 16 | 8 |
| POSTEMERGENCE | | | | | | |
| Corn | 23 | 22 | 11 | 6 | — | — |
| Soybean | 80 | 78 | 79 | 77 | — | — |
| Velvetleaf | — | — | 98 | 97 | 95 | 93 |
| Pigweed | — | — | 88 | 95 | 88 | 60 |
| Ivyleaf morningglory | — | — | 96 | 96 | 93 | 90 |
| Cocklebur | — | — | 99 | 98 | 97 | 91 |
| Crabgrass | — | — | 0 | 0 | 0 | 0 |
| Giant foxtail | — | — | 21 | 13 | 0 | 0 |
| Johnsongrass | — | — | 80 | 50 | 0 | 0 |
| Barnyardgrass | — | — | 0 | 0 | 0 | 0 |
| PREEMERGENCE | | | | | | |
| Corn | 54 | 38 | 25 | 23 | — | — |
| Soybean | 81 | 79 | 74 | 66 | — | — |
| Velvetleaf | — | — | 98 | 85 | 75 | 36 |
| Pigweed | — | — | 97 | 95 | 86 | 78 |
| Ivyleaf morningglory | — | — | 95 | 78 | 46 | 11 |
| Cocklebur | — | — | 85 | 90 | 75 | 46 |
| Crabgrass | — | — | 0 | 0 | 0 | 0 |
| Giant foxtail | — | — | 10 | 6 | 0 | 0 |
| Johnsongrass | — | — | 71 | 33 | 50 | 0 |
| Barnyardgrass | — | — | 18 | 6 | 0 | 0 |
| Rate g/ha | 125 | 62 | 31 | 16 | 8 | 4 | 2 |
| POSTEMERGENCE | | | | | | | |
| Corn | 30 | 22 | 12 | 15 | — | — | — |
| Soybean | — | — | 79 | 75 | 70 | 67 | — |
| Velvetleaf | — | — | — | 95 | 95 | 81 | 31 |
| Pigweed | — | — | — | 86 | 91 | 78 | 46 |
| Ivyleaf morningglory | — | — | — | 96 | 96 | 91 | 81 |
| Cocklebur | — | — | — | 98 | 98 | 94 | 76 |
| Crabgrass | — | 0 | 0 | 0 | 0 | — | — |
| Giant foxtail | — | 6 | 0 | 0 | 0 | — | — |
| Johnsongrass | — | 60 | 30 | 13 | 0 | — | — |

TABLE D-continued

| | Compound 1 % injury/% control | | | | | |
|---|---|---|---|---|---|---|
| Barnyardgrass | — | 0 | 0 | 0 | 0 | — | — |
| Corn | 33 | 23 | 8 | 9 | — | — | — |
| Soybean | — | — | 53 | 36 | 28 | 5 | — |
| Velvetleaf | — | — | — | 86 | 50 | 43 | 0 |
| Pigweed | — | — | — | 89 | 73 | 56 | 0 |
| Ivyleaf morningglory | — | — | — | 63 | 13 | 0 | 0 |
| Cocklebur | — | — | — | 83 | 56 | 16 | 0 |
| Crabgrass | — | 0 | 0 | 0 | 0 | — | — |
| Giant foxtail | — | 40 | 33 | 20 | 0 | — | — |
| Johnsongrass | — | 86 | 46 | 13 | 0 | — | — |
| Barnyardgrass | — | 16 | 0 | 0 | 0 | — | — |

What is claimed is:

1. A compound of the formula

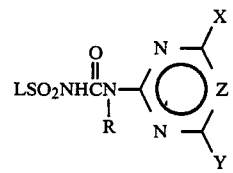

wherein
R is H or CH₃;
X is CH₃ or OCH₃;
Y is OCH₂CH₂F, OCH₂CHF₂ or OCH₂CF₃;
Z is CH

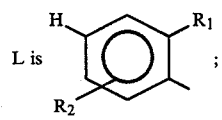

$R_1$ is $C_2$-$C_4$ alkyl, $C_2$-$C_4$ alkoxy, $SO_2NR_8R_9$, $SO_2N(OCH_3)CH_3$ or 2-tetrahydrofuranyl;
$R_2$ is H, F, Cl, Br, CF₃, CH₃, OCH₃ or SCH₃;
$R_8$ is $C_1$-$C_3$ alkyl; and
$R_9$ is $C_1$-$C_3$ alkyl; and their agriculturally suitable salts; provided that
(1) the total number of carbon atoms of $R_8$ and $R_9$ is less than or equal to four; and
(2) when $R_1$ is $SO_2NR_8R_9$, $SO_2N(OCH_3)CH_3$ or 2-tetrahydrofuranyl, then Y is OCH₂CH₂F or OCH₂CHF₂.

2. A compound of claim 1 wherein R is H; $R_1$ is $C_2$-$C_3$ alkoxy and $R_2$ is H.

3. A composition suitable for controlling the growth of undesired vegetation which comprises an effective amount of a compound of claim 1 and at least one of the following: surfactant, solid or liquid diluent.

4. A composition suitable for controlling the growth of undesired vegetation which comprises an effective amount of a compound of claim 2 and at least one of the following: surfactant, solid or liquid diluent.

5. A method for controlling the growth of undesired vegetation which comprises applying to the locus to be protected an effective amount of a compound of claim 1.

6. A method for controlling the growth of undesired vegetation which comprises applying to the locus to be protected an effective amount of a compound of claim 2.

* * * * *